(12) United States Patent
Guidotti et al.

(10) Patent No.: US 12,426,887 B2
(45) Date of Patent: *Sep. 30, 2025

(54) LEFT ATRIAL APPENDAGE OCCLUSION DEVICES

(71) Applicant: UNIVERSITÄT ZÜRICH, Zürich (CH)

(72) Inventors: Andrea Guidotti, Schwerzenbach (CH); Boaz Harari, Ganey Tikva (IL); Pietro Gozzoli, Zürich (CH); Luca Vicentini, Opfikon (CH)

(73) Assignee: UNIVERSITÄT ZÜRICH, Zurich (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/619,777

(22) Filed: Mar. 28, 2024

(65) Prior Publication Data

US 2024/0237987 A1 Jul. 18, 2024

Related U.S. Application Data

(63) Continuation of application No. 17/763,485, filed as application No. PCT/IL2020/051041 on Sep. 24, 2020, now Pat. No. 11,944,315.

(Continued)

(51) Int. Cl.
*A61B 17/12* (2006.01)
*A61B 17/00* (2006.01)

(52) U.S. Cl.
CPC .. *A61B 17/12122* (2013.01); *A61B 17/12136* (2013.01); *A61B 2017/00619* (2013.01);
(Continued)

(58) Field of Classification Search
CPC ........ A61B 17/12136; A61B 17/12172; A61B 17/12122; A61B 17/0057;
(Continued)

(56) References Cited

U.S. PATENT DOCUMENTS 3,834,394 A  9/1974 Hunter et al.
4,686,962 A  8/1987 Haber
(Continued)

FOREIGN PATENT DOCUMENTS

CN  104905890 A  9/2015
CN  204971415 U  1/2016
(Continued)

OTHER PUBLICATIONS

Notice of Allowance issued in United States Office Action issued Jun. 24, 2022 in U.S. Appl. No. 16/649,777.
(Continued)

*Primary Examiner* — Katherine H Schwiker
*Assistant Examiner* — Lauren Dubose
(74) *Attorney, Agent, or Firm* — Sughrue Mion, PLLC

(57) ABSTRACT

An occlusion device is provided for occluding a left atrial appendage (LAA), including a compliant balloon defining a fluid-tight balloon chamber. An actuating shaft is disposed at least partially within the balloon chamber, and configured to set a distance between distal and proximal end portions of the balloon. A locking mechanism is configured to assume locked and unlocked states, and is configured, when in the locked state, to maintain, between the distal and the proximal end portions of the balloon, the distance set using the actuating shaft. The occlusion device is shaped so as to define a fluid flow path along a portion of the actuating shaft. A valve is configured to selectively allow or block fluid flow between the fluid flow path and the balloon chamber when the valve is in open and closed states, respectively. Other embodiments are also described.

21 Claims, 21 Drawing Sheets

Related U.S. Application Data

(60) Provisional application No. 62/906,393, filed on Sep. 26, 2019.

(52) U.S. Cl.
CPC ............... *A61B 2017/00632* (2013.01); *A61B 2017/00853* (2013.01); *A61B 2017/12095* (2013.01)

(58) Field of Classification Search
CPC ........ A61B 17/12022; A61B 17/12031; A61B 17/12099; A61B 17/1213; A61B 2017/00632; A61B 2017/12095; A61B 2017/12054; A61B 2017/00619; A61B 2017/00243; A61B 2017/00557; A61B 2017/00575; A61B 2017/22067; A61B 2017/1205; A61B 2018/0022; A61M 25/10; A61M 25/1025; A61M 2025/1052; A61M 2025/1054; A61M 2210/125
See application file for complete search history.

(56) References Cited

U.S. PATENT DOCUMENTS

| | | | |
|---|---|---|---|
| 4,802,479 A | 2/1989 | Haber et al. |
| 5,181,921 A | 1/1993 | Makita et al. |
| 5,411,475 A | 5/1995 | Atala et al. |
| 5,499,995 A | 3/1996 | Teirstein |
| 5,795,325 A | 8/1998 | Valley et al. |
| 5,830,228 A | 11/1998 | Knapp et al. |
| 5,853,422 A | 12/1998 | Huebsch et al. |
| 6,117,159 A | 9/2000 | Huebsch et al. |
| 6,174,322 B1 | 1/2001 | Schneidt |
| 6,231,561 B1 | 5/2001 | Frazier et al. |
| 6,267,747 B1 | 7/2001 | Samson et al. |
| 6,273,907 B1 | 8/2001 | Laufer |
| 6,290,674 B1 | 9/2001 | Roue et al. |
| 6,328,727 B1 | 12/2001 | Frazier et al. |
| 6,334,864 B1 | 1/2002 | Amplatz et al. |
| 6,419,669 B1 | 7/2002 | Frazier et al. |
| 6,440,097 B1 | 8/2002 | Kupiecki |
| 6,468,301 B1 | 10/2002 | Amplatz et al. |
| 6,468,303 B1 | 10/2002 | Amplatz et al. |
| 6,488,689 B1 | 12/2002 | Kaplan et al. |
| 6,537,300 B2 | 3/2003 | Girton |
| 6,544,268 B1 | 4/2003 | Lazarus |
| 6,551,303 B1 | 4/2003 | Van Tassel et al. |
| 6,638,257 B2 | 10/2003 | Amplatz |
| 6,652,555 B1 | 11/2003 | VanTassel et al. |
| 6,652,556 B1 | 11/2003 | VanTassel et al. |
| 6,656,488 B2 | 12/2003 | Yi et al. |
| 6,692,491 B1 | 2/2004 | Phan |
| 6,926,712 B2 | 8/2005 | Phan |
| 6,932,816 B2 | 8/2005 | Phan |
| 6,941,169 B2 | 9/2005 | Pappu |
| 6,942,661 B2 | 9/2005 | Swanson |
| 6,942,681 B2 | 9/2005 | Johnson |
| 6,964,669 B1 | 11/2005 | Knapp et al. |
| 6,970,742 B2 | 11/2005 | Mann et al. |
| 6,994,092 B2 | 2/2006 | Van Der et al. |
| 7,011,671 B2 | 3/2006 | Welch |
| 7,044,134 B2 | 5/2006 | Khairkhahan et al. |
| 7,056,294 B2 | 6/2006 | Khairkhahan et al. |
| 7,169,164 B2 | 1/2007 | Borillo et al. |
| 7,211,048 B1 | 5/2007 | Najafi et al. |
| 7,293,562 B2 | 11/2007 | Malecki et al. |
| 7,338,514 B2 | 3/2008 | Wahr et al. |
| 7,374,560 B2 | 5/2008 | Ressemann et al. |
| 7,470,282 B2 | 12/2008 | Shelso |
| 7,473,271 B2 | 1/2009 | Gunderson |
| 7,483,743 B2 | 1/2009 | Mann et al. |
| 7,549,988 B2 | 6/2009 | Eberl et al. |
| 7,597,704 B2 | 10/2009 | Frazier et al. |
| 7,604,612 B2 | 10/2009 | Ressemann et al. |
| 7,615,010 B1 | 11/2009 | Najafi et al. |
| 7,654,978 B2 | 2/2010 | Wahr et al. |
| 7,713,282 B2 | 5/2010 | Frazier et al. |
| 7,722,641 B2 | 5/2010 | Van Der Burg et al. |
| 7,735,493 B2 | 6/2010 | Van Der Burg et al. |
| 7,740,627 B2 | 6/2010 | Gammie et al. |
| 7,749,157 B2 | 7/2010 | Bertolero |
| 7,824,341 B2 | 11/2010 | Krishnan |
| 7,828,818 B2 | 11/2010 | Zang et al. |
| 7,837,619 B2 | 11/2010 | Sogard et al. |
| 7,846,168 B2 | 12/2010 | Liddicoat et al. |
| 7,846,175 B2 | 12/2010 | Bonnette et al. |
| 7,857,811 B2 | 12/2010 | Vaska et al. |
| 7,892,228 B2 | 2/2011 | Landis et al. |
| 7,918,865 B2 | 4/2011 | Liddicoat et al. |
| 7,972,359 B2 | 7/2011 | Kreidler |
| 7,976,564 B2 | 7/2011 | Blaeser et al. |
| 7,998,095 B2 | 8/2011 | McAuley |
| 7,998,138 B2 | 8/2011 | McAuley |
| 8,002,771 B2 | 8/2011 | Cox et al. |
| 8,034,061 B2 | 10/2011 | Amplatz et al. |
| 8,043,258 B2 | 10/2011 | Ostroot |
| 8,048,147 B2 | 11/2011 | Adams |
| 8,052,715 B2 | 11/2011 | Quinn et al. |
| 8,057,530 B2 | 11/2011 | Kusleika et al. |
| 8,080,032 B2 | 12/2011 | Van Der Burg et al. |
| 8,097,015 B2 | 1/2012 | Devellian |
| 8,100,938 B2 | 1/2012 | Figulla et al. |
| 8,108,069 B2 | 1/2012 | Stahler et al. |
| 8,114,123 B2 | 2/2012 | Brenzel et al. |
| 8,133,221 B2 | 3/2012 | Malecki et al. |
| 8,142,470 B2 | 3/2012 | Quinn et al. |
| 8,148,470 B1 | 4/2012 | Holtcamp et al. |
| 8,162,974 B2 | 4/2012 | Eskuri et al. |
| 8,163,004 B2 | 4/2012 | Amplatz et al. |
| 8,167,894 B2 | 5/2012 | Miles et al. |
| 8,167,905 B2 | 5/2012 | Michler et al. |
| 8,197,527 B2 | 6/2012 | Borillo et al. |
| 8,204,605 B2 | 6/2012 | Hastings et al. |
| 8,211,096 B2 | 7/2012 | Pless et al. |
| 8,221,348 B2 | 7/2012 | Hackett et al. |
| 8,221,405 B2 | 7/2012 | Whisenant et al. |
| 8,235,885 B2 | 8/2012 | Whisenant et al. |
| 8,235,988 B2 | 8/2012 | Davis et al. |
| 8,252,051 B2 | 8/2012 | Chau et al. |
| 8,257,724 B2 | 9/2012 | Cromack et al. |
| 8,257,725 B2 | 9/2012 | Cromack et al. |
| 8,308,798 B2 | 11/2012 | Pintor et al. |
| 8,313,505 B2 | 11/2012 | Amplatz et al. |
| 8,361,138 B2 | 1/2013 | Adams |
| 8,366,743 B2 | 2/2013 | Zeng et al. |
| 8,372,112 B2 | 2/2013 | Christianson et al. |
| 8,398,670 B2 | 3/2013 | Amplatz et al. |
| 8,402,974 B2 | 3/2013 | Davis et al. |
| 8,408,214 B2 | 4/2013 | Spenser |
| 8,409,219 B2 | 4/2013 | Kelley et al. |
| 8,463,359 B2 | 6/2013 | Saadat et al. |
| 8,480,708 B2 | 7/2013 | Kassab et al. |
| 8,491,649 B2 | 7/2013 | Mach |
| 8,511,214 B2 | 8/2013 | Gries |
| 8,523,897 B2 | 9/2013 | Van Der Burg et al. |
| 8,523,940 B2 | 9/2013 | Richardson et al. |
| 8,529,597 B2 | 9/2013 | Linder et al. |
| 8,540,616 B2 | 9/2013 | Whisenant et al. |
| 8,545,491 B2 | 10/2013 | Abboud et al. |
| 8,550,982 B2 | 10/2013 | Eby |
| 8,568,474 B2 | 10/2013 | Yeung et al. |
| 8,574,264 B2 | 11/2013 | Blaeser et al. |
| 8,613,765 B2 | 12/2013 | Bonhoeffer et al. |
| 8,617,145 B2 | 12/2013 | Longoria |
| 8,621,975 B2 | 1/2014 | Russo et al. |
| 8,636,764 B2 | 1/2014 | Miles et al. |
| 8,647,361 B2 | 2/2014 | Borillo et al. |
| 8,647,367 B2 | 2/2014 | Kassab et al. |
| 8,652,201 B2 | 2/2014 | Oberti et al. |
| 8,663,245 B2 | 3/2014 | Francischelli et al. |
| 8,673,001 B2 | 3/2014 | Cartledge et al. |
| 8,690,911 B2 | 4/2014 | Miles et al. |
| 8,696,742 B2 | 4/2014 | Pintor et al. |

(56) References Cited

U.S. PATENT DOCUMENTS

| | | |
|---|---|---|
| 8,709,007 B2 | 4/2014 | Vaska |
| 8,715,270 B2 | 5/2014 | Weitzner et al. |
| 8,721,636 B2 | 5/2014 | Vaska et al. |
| 8,740,934 B2 | 6/2014 | McGuckin, Jr. |
| 8,747,297 B2 | 6/2014 | Miyoshi et al. |
| 8,747,453 B2 | 6/2014 | Amplatz et al. |
| 8,747,462 B2 | 6/2014 | Hill et al. |
| 8,758,294 B2 | 6/2014 | Kim et al. |
| 8,758,372 B2 | 6/2014 | Cartledge et al. |
| 8,758,389 B2 | 6/2014 | Glimsdale |
| 8,764,787 B2 | 7/2014 | Ren |
| 8,764,793 B2 | 7/2014 | Lee |
| 8,771,297 B2 | 7/2014 | Miller et al. |
| 8,777,974 B2 | 7/2014 | Amplatz et al. |
| 8,778,008 B2 | 7/2014 | Amplatz et al. |
| 8,784,469 B2 | 7/2014 | Kassab |
| 8,795,310 B2 | 8/2014 | Fung et al. |
| 8,795,328 B2 | 8/2014 | Miles et al. |
| 8,801,706 B2 | 8/2014 | Rothstein et al. |
| 8,801,746 B1 | 8/2014 | Kreidler et al. |
| 8,808,371 B2 | 8/2014 | Cartledge |
| 8,814,778 B2 | 8/2014 | Kiser et al. |
| D713,527 S | 9/2014 | Heipl |
| 8,821,529 B2 | 9/2014 | Kariniemi et al. |
| 8,834,519 B2 | 9/2014 | Van Der Burg et al. |
| 8,840,641 B2 | 9/2014 | Miles et al. |
| 8,840,655 B2 | 9/2014 | Edmiston et al. |
| 8,845,711 B2 | 9/2014 | Miles et al. |
| 8,864,809 B2 | 10/2014 | Miles et al. |
| 8,864,823 B2 | 10/2014 | Cartledge et al. |
| 8,876,776 B2 | 11/2014 | Kassab et al. |
| 8,880,185 B2 | 11/2014 | Hastings et al. |
| 8,882,830 B2 | 11/2014 | Cartledge et al. |
| 8,900,287 B2 | 12/2014 | Amplatz et al. |
| 8,915,958 B2 | 12/2014 | Braido |
| 8,940,015 B2 | 1/2015 | Kariniemi |
| 8,951,251 B2 | 2/2015 | Willard |
| 8,956,304 B2 | 2/2015 | Schecter |
| 8,974,451 B2 | 3/2015 | Smith |
| 8,979,941 B2 | 3/2015 | Davis et al. |
| 8,986,375 B2 | 3/2015 | Garde et al. |
| D727,500 S | 4/2015 | Heipl |
| D727,501 S | 4/2015 | Heipl |
| D728,102 S | 4/2015 | Heipl |
| 9,011,551 B2 | 4/2015 | Oral et al. |
| 9,017,375 B2 | 4/2015 | Thommen |
| 9,023,034 B2 | 5/2015 | Jenson et al. |
| 9,028,485 B2 | 5/2015 | Edmunds et al. |
| 9,034,006 B2 | 5/2015 | Quinn et al. |
| 9,039,724 B2 | 5/2015 | Amplatz et al. |
| 9,039,752 B2 | 5/2015 | Russo et al. |
| 9,050,106 B2 | 6/2015 | Hill et al. |
| 9,055,933 B2 | 6/2015 | Escobar et al. |
| 9,055,959 B2 | 6/2015 | Vaska et al. |
| 9,060,761 B2 | 6/2015 | Hastings et al. |
| 9,066,710 B2 | 6/2015 | Dale et al. |
| 9,066,826 B2 | 6/2015 | Heidner et al. |
| 9,072,602 B2 | 7/2015 | Glozman et al. |
| 9,072,604 B1 | 7/2015 | Melnick et al. |
| 9,079,000 B2 | 7/2015 | Hanson et al. |
| 9,084,589 B2 | 7/2015 | Moszner |
| 9,084,609 B2 | 7/2015 | Smith |
| 9,084,621 B2 | 7/2015 | Weitzner et al. |
| 9,089,350 B2 | 7/2015 | Willard |
| 9,089,414 B2 | 7/2015 | Zimmerman et al. |
| 9,107,750 B2 | 8/2015 | Cartledge et al. |
| 9,113,890 B2 | 8/2015 | Dasnurkar et al. |
| 9,119,600 B2 | 9/2015 | Richardson et al. |
| 9,119,632 B2 | 9/2015 | Jenson et al. |
| 9,125,653 B2 | 9/2015 | Kovach |
| 9,131,932 B2 | 9/2015 | Tegels |
| 9,132,007 B2 | 9/2015 | Menk et al. |
| 9,138,208 B2 | 9/2015 | Linder et al. |
| 9,144,431 B2 | 9/2015 | Friedman et al. |
| 9,144,663 B2 | 9/2015 | Ahlberg et al. |
| 9,155,589 B2 | 10/2015 | Jenson |
| 9,161,758 B2 | 10/2015 | Figulla et al. |
| 9,162,046 B2 | 10/2015 | Hill et al. |
| 9,173,696 B2 | 11/2015 | Schauer et al. |
| 9,186,174 B2 | 11/2015 | Krishnan |
| 9,186,209 B2 | 11/2015 | Weber et al. |
| 9,186,210 B2 | 11/2015 | Jenson |
| 9,186,211 B2 | 11/2015 | Mathur |
| 9,192,435 B2 | 11/2015 | Jenson |
| 9,192,790 B2 | 11/2015 | Hastings et al. |
| 9,198,683 B2 | 12/2015 | Friedman et al. |
| 9,216,014 B2 | 12/2015 | Devellian et al. |
| 9,220,402 B2 | 12/2015 | Rothe et al. |
| 9,220,487 B2 | 12/2015 | Davis et al. |
| 9,220,558 B2 | 12/2015 | Willard |
| 9,220,561 B2 | 12/2015 | Crow et al. |
| 9,226,838 B2 | 1/2016 | Wang et al. |
| 9,232,992 B2 | 1/2016 | Heidner et al. |
| 9,241,792 B2 | 1/2016 | Benichou et al. |
| 9,254,141 B2 | 2/2016 | Morris et al. |
| 9,254,192 B2 | 2/2016 | Lutter et al. |
| 9,271,736 B2 | 3/2016 | Heipl |
| 9,277,905 B2 | 3/2016 | Cully et al. |
| 9,277,915 B2 | 3/2016 | Belson et al. |
| 9,289,266 B2 | 3/2016 | Weitzner et al. |
| 9,290,612 B2 | 3/2016 | Martin et al. |
| 9,295,472 B2 | 3/2016 | Ottma |
| 9,295,484 B2 | 3/2016 | Solem |
| 9,297,845 B2 | 3/2016 | Mathur |
| 9,301,838 B2 | 4/2016 | Kapadia |
| 9,307,999 B2 | 4/2016 | Li et al. |
| 9,320,525 B2 | 4/2016 | Khieu et al. |
| 9,326,751 B2 | 5/2016 | Hastings |
| 9,326,852 B2 | 5/2016 | Spenser |
| 9,333,073 B2 | 5/2016 | Quadri et al. |
| 9,339,274 B2 | 5/2016 | Dakin |
| 9,345,462 B2 | 5/2016 | Weitzner et al. |
| 9,351,716 B2 | 5/2016 | Miles et al. |
| 9,358,365 B2 | 6/2016 | Smith et al. |
| 9,364,284 B2 | 6/2016 | Groff et al. |
| 9,370,418 B2 | 6/2016 | Pintor et al. |
| 9,375,209 B2 | 6/2016 | Akpinar |
| 9,375,218 B2 | 6/2016 | Wheeler et al. |
| 9,398,951 B2 | 7/2016 | Alkhatib et al. |
| 9,408,608 B2 | 8/2016 | Clark, III et al. |
| 9,408,661 B2 | 8/2016 | Haverkost |
| 9,408,951 B2 | 8/2016 | Larsen et al. |
| 9,414,842 B2 | 8/2016 | Glimsdale et al. |
| 9,420,955 B2 | 8/2016 | Weber |
| 9,421,071 B2 | 8/2016 | Smith et al. |
| 9,427,215 B2 | 8/2016 | Cartledge et al. |
| 9,427,235 B2 | 8/2016 | Krishnan |
| 9,427,550 B2 | 8/2016 | Dakin et al. |
| 9,433,760 B2 | 9/2016 | Subramaniam et al. |
| 9,445,798 B2 | 9/2016 | Amplatz et al. |
| 9,445,799 B2 | 9/2016 | Amplatz et al. |
| 9,456,877 B2 | 10/2016 | Weitzner et al. |
| 9,456,897 B2 | 10/2016 | Krivoruchko et al. |
| 9,463,024 B2 | 10/2016 | Kiser et al. |
| 9,463,062 B2 | 10/2016 | Smith et al. |
| 9,468,437 B2 | 10/2016 | Michler et al. |
| 9,474,516 B2 | 10/2016 | Clark et al. |
| 9,474,598 B2 | 10/2016 | Gregg et al. |
| 9,474,599 B2 | 10/2016 | Keränen |
| 9,492,156 B2 | 11/2016 | Tegels |
| 9,492,276 B2 | 11/2016 | Lee et al. |
| 9,492,623 B2 | 11/2016 | Kapadia et al. |
| 9,498,206 B2 | 11/2016 | Fung et al. |
| 9,498,228 B2 | 11/2016 | Dale et al. |
| 9,510,811 B2 | 12/2016 | Akpinar |
| 9,532,772 B2 | 1/2017 | Moszner et al. |
| 9,545,306 B2 | 1/2017 | Tabor |
| 9,572,583 B2 | 2/2017 | Kauphusman et al. |
| 9,579,030 B2 | 2/2017 | Scheuermann et al. |
| 9,579,194 B2 | 2/2017 | Elizondo et al. |
| 9,585,643 B2 | 3/2017 | Terwey |
| 9,585,644 B2 | 3/2017 | Linder et al. |
| 9,610,082 B2 | 4/2017 | Morris et al. |
| 9,622,133 B1 | 4/2017 | Guvenc |

(56) References Cited

U.S. PATENT DOCUMENTS

| | | | |
|---|---|---|---|
| 9,636,222 B2 | 5/2017 | Oslund |
| 9,642,706 B2 | 5/2017 | Eidenschink |
| 9,649,115 B2 | 5/2017 | Edmiston et al. |
| 9,649,156 B2 | 5/2017 | Jenson et al. |
| 9,650,730 B2 | 5/2017 | Heipl et al. |
| 9,655,606 B2 | 5/2017 | Le |
| 9,662,205 B2 | 5/2017 | Eidenschink |
| 9,668,811 B2 | 6/2017 | Sogard et al. |
| 9,668,856 B2 | 6/2017 | Para |
| 9,668,857 B2 | 6/2017 | Braido et al. |
| 9,668,858 B2 | 6/2017 | Morin et al. |
| 9,675,451 B2 | 6/2017 | Garde et al. |
| 9,681,861 B2 | 6/2017 | Heisel et al. |
| 9,687,166 B2 | 6/2017 | Subramaniam et al. |
| 9,687,341 B2 | 6/2017 | Alkhatib et al. |
| 9,687,585 B2 | 6/2017 | Bernasconi et al. |
| 9,693,781 B2 | 7/2017 | Miles et al. |
| 9,693,821 B2 | 7/2017 | Hanson et al. |
| 9,694,115 B2 | 7/2017 | Zhang et al. |
| 9,700,323 B2 | 7/2017 | Clark |
| 9,707,036 B2 | 7/2017 | Anderson et al. |
| 9,713,730 B2 | 7/2017 | Mathur et al. |
| 9,717,501 B2 | 8/2017 | Kauphusman et al. |
| 9,730,701 B2 | 8/2017 | Tischler et al. |
| 9,737,309 B1 | 8/2017 | Ad |
| 9,750,605 B2 | 9/2017 | Ganesan et al. |
| 9,757,230 B2 | 9/2017 | Fahim et al. |
| 9,770,606 B2 | 9/2017 | Pikus et al. |
| 9,775,533 B2 | 10/2017 | Ong et al. |
| 9,789,232 B2 | 10/2017 | Liu et al. |
| 9,795,387 B2 | 10/2017 | Miles et al. |
| 9,795,481 B2 | 10/2017 | Callas et al. |
| 9,795,765 B2 | 10/2017 | Romoscanu |
| 9,808,253 B2 | 11/2017 | Li et al. |
| 9,808,300 B2 | 11/2017 | Hastings et al. |
| 9,808,311 B2 | 11/2017 | Wang et al. |
| 9,820,851 B2 | 11/2017 | Braido |
| 9,820,852 B2 | 11/2017 | Braido et al. |
| 9,827,039 B2 | 11/2017 | Dandler et al. |
| 9,833,283 B2 | 12/2017 | Hanson et al. |
| 9,839,430 B2 | 12/2017 | Willems et al. |
| 9,839,431 B2 | 12/2017 | Meyer et al. |
| 9,844,453 B2 | 12/2017 | Stack et al. |
| 9,848,898 B2 | 12/2017 | Friedman et al. |
| 9,848,976 B2 | 12/2017 | Angel et al. |
| 9,848,981 B2 | 12/2017 | Suri et al. |
| 9,863,031 B2 | 1/2018 | Zhang et al. |
| 9,867,697 B2 | 1/2018 | Alkhatib et al. |
| 9,877,710 B2 | 1/2018 | Amplatz et al. |
| 9,877,726 B2 | 1/2018 | Liu et al. |
| 9,878,072 B2 | 1/2018 | Zhang et al. |
| 9,883,855 B2 | 2/2018 | Tegels et al. |
| 9,883,936 B2 | 2/2018 | Sutton et al. |
| 9,888,926 B2 | 2/2018 | Phan et al. |
| 9,889,004 B2 | 2/2018 | Braido |
| 9,895,194 B2 | 2/2018 | Anderson et al. |
| 9,901,443 B2 | 2/2018 | Morriss et al. |
| 9,907,609 B2 | 3/2018 | Cao et al. |
| 9,913,652 B2 | 3/2018 | Bridgeman et al. |
| 9,913,715 B2 | 3/2018 | Braido et al. |
| 9,918,707 B2 | 3/2018 | Zhuang |
| 9,919,080 B1 | 3/2018 | Chen et al. |
| 9,925,001 B2 | 3/2018 | Willard et al. |
| 9,931,204 B2 | 4/2018 | Rothstein et al. |
| 9,936,956 B2 | 4/2018 | Fung et al. |
| 9,943,315 B2 | 4/2018 | Kaplan et al. |
| 9,943,365 B2 | 4/2018 | Haverkost et al. |
| 9,949,825 B2 | 4/2018 | Braido et al. |
| 9,955,971 B2 | 5/2018 | Xu et al. |
| 9,956,033 B2 | 5/2018 | Squire et al. |
| 9,962,223 B2 | 5/2018 | Lindquist et al. |
| 9,974,649 B2 | 5/2018 | Racchini et al. |
| 9,980,818 B2 | 5/2018 | Chau et al. |
| 9,993,234 B2 | 6/2018 | Maslanka et al. |
| 10,010,402 B2 | 7/2018 | Wang et al. |
| 10,013,082 B2 | 7/2018 | Schecter |
| 10,016,200 B2 | 7/2018 | Tegels |
| 10,022,182 B2 | 7/2018 | Willard et al. |
| 10,028,746 B2 | 7/2018 | Prom |
| 10,034,748 B2 | 7/2018 | Tseng et al. |
| 10,045,784 B2 | 8/2018 | Friedman et al. |
| 10,052,168 B2 | 8/2018 | Krishnan |
| 10,058,348 B2 | 8/2018 | Morris et al. |
| 10,058,636 B2 | 8/2018 | Xie et al. |
| 10,058,639 B2 | 8/2018 | Zhang et al. |
| 10,064,612 B2 | 9/2018 | Malakan Rad et al. |
| 10,064,628 B2 | 9/2018 | Edmiston et al. |
| 10,076,330 B2 | 9/2018 | Sander et al. |
| 10,076,335 B2 | 9/2018 | Zaver et al. |
| 10,085,799 B2 | 10/2018 | Smith |
| 10,098,640 B2 | 10/2018 | Bertolero et al. |
| 10,105,219 B2 | 10/2018 | Kovach |
| 10,117,743 B2 | 11/2018 | Kumar et al. |
| 10,130,369 B2 | 11/2018 | Fung et al. |
| 10,130,467 B2 | 11/2018 | Braido et al. |
| 10,143,478 B2 | 12/2018 | Forbes |
| 10,143,551 B2 | 12/2018 | Braido et al. |
| 10,271,949 B2 | 4/2019 | Dakin et al. |
| 2003/0139819 A1 | 7/2003 | Beer et al. |
| 2003/0191516 A1 | 10/2003 | Weldon et al. |
| 2003/0220667 A1 | 11/2003 | Van Der Burg et al. |
| 2004/0044361 A1 | 3/2004 | Frazier et al. |
| 2004/0098017 A1 | 5/2004 | Saab et al. |
| 2004/0254594 A1 | 12/2004 | Alfaro |
| 2005/0043759 A1 | 2/2005 | Chanduszko |
| 2005/0288706 A1 | 12/2005 | Widomski et al. |
| 2006/0004442 A1 | 1/2006 | Spenser et al. |
| 2006/0200191 A1 | 9/2006 | Zadno-azizi et al. |
| 2007/0135831 A1 | 6/2007 | Burnett |
| 2007/0225756 A1 | 9/2007 | Preinitz et al. |
| 2008/0071310 A1 | 3/2008 | Hoffman et al. |
| 2008/0103479 A1 | 5/2008 | Cheng et al. |
| 2010/0100107 A1* | 4/2010 | Duggal ............ A61B 17/12172 606/198 |
| 2010/0125244 A1 | 5/2010 | McAndrew |
| 2010/0185233 A1* | 7/2010 | Thommen .......... A61B 17/0057 606/213 |
| 2011/0172697 A1 | 7/2011 | Jönsson |
| 2012/0078295 A1 | 3/2012 | Steiner et al. |
| 2012/0323270 A1 | 12/2012 | Lee |
| 2013/0030519 A1 | 1/2013 | Tran et al. |
| 2013/0211495 A1 | 8/2013 | Halden et al. |
| 2014/0100596 A1 | 4/2014 | Rudman et al. |
| 2014/0257457 A1 | 9/2014 | Glazier et al. |
| 2014/0277426 A1 | 9/2014 | Dakin et al. |
| 2016/0045165 A1 | 2/2016 | Braido et al. |
| 2018/0008248 A1 | 1/2018 | Rafiee et al. |
| 2018/0161039 A1 | 6/2018 | Harks |
| 2018/0193027 A1 | 7/2018 | Wang et al. |
| 2018/0206850 A1 | 7/2018 | Wang et al. |
| 2019/0223883 A1 | 7/2019 | Anderson et al. |
| 2020/0054343 A1 | 2/2020 | Min et al. |
| 2020/0085445 A1 | 3/2020 | Wang et al. |
| 2020/0100797 A1 | 4/2020 | Wang et al. |
| 2020/0107836 A1 | 4/2020 | O'halloran et al. |
| 2020/0121891 A1 | 4/2020 | Zhang et al. |
| 2020/0275935 A1 | 9/2020 | Maisano et al. |
| 2020/0305887 A1 | 10/2020 | Lashinski et al. |
| 2021/0298728 A1 | 9/2021 | Lashinski et al. |
| 2021/0386429 A1 | 12/2021 | Franano et al. |
| 2022/0022854 A1 | 1/2022 | Lashinski et al. |
| 2022/0087741 A1 | 3/2022 | Lashinski et al. |
| 2022/0346803 A1 | 11/2022 | Wang et al. |
| 2023/0139430 A1 | 5/2023 | Zhao et al. |

FOREIGN PATENT DOCUMENTS

| | | |
|---|---|---|
| CN | 106344082 A | 1/2017 |
| CN | 207928350 U | 10/2018 |
| CN | 207928351 U | 10/2018 |
| CN | 109199468 A | 1/2019 |
| CN | 208709959 U | 4/2019 |
| CN | 209107426 U | 7/2019 |
| CN | 209107470 U | 7/2019 |

(56) References Cited

FOREIGN PATENT DOCUMENTS

| | | |
|---|---|---|
| CN | 209611296 U | 11/2019 |
| CN | 209611297 U | 11/2019 |
| CN | 110720958 A | 1/2020 |
| CN | 209884221 U | 1/2020 |
| CN | 210408510 U | 4/2020 |
| CN | 210408511 U | 4/2020 |
| CN | 111166461 A | 5/2020 |
| CN | 111166462 A | 5/2020 |
| CN | 111166463 A | 5/2020 |
| CN | 211723305 U | 10/2020 |
| CN | 217723411 U | 10/2020 |
| CN | 211934281 U | 11/2020 |
| CN | 211934282 U | 11/2020 |
| CN | 212015753 U | 11/2020 |
| CN | 112120780 A | 12/2020 |
| CN | 212165820 U | 12/2020 |
| CN | 212165887 U | 12/2020 |
| CN | 212346701 U | 1/2021 |
| CN | 212346702 U | 1/2021 |
| CN | 212346703 U | 1/2021 |
| CN | 212490124 U | 2/2021 |
| CN | 212490130 U | 2/2021 |
| CN | 112568955 A | 3/2021 |
| CN | 212996551 U | 4/2021 |
| CN | 112754650 A | 5/2021 |
| CN | 112754651 A | 5/2021 |
| CN | 112998769 A | 6/2021 |
| CN | 112998839 A | 6/2021 |
| CN | 113116500 A | 7/2021 |
| CN | 113116501 A | 7/2021 |
| CN | 116440245 A | 9/2021 |
| CN | 113576647 A | 11/2021 |
| CN | 113876369 A | 1/2022 |
| CN | 113876370 A | 1/2022 |
| CN | 114052889 A | 2/2022 |
| CN | 106473791 B | 10/2023 |
| CN | 106466196 B | 11/2023 |
| CN | 108926371 B | 4/2024 |
| EP | 1651117 | 1/2007 |
| EP | 1113751 | 3/2007 |
| EP | 1154723 | 12/2007 |
| EP | 1891902 | 2/2008 |
| EP | 1788957 | 3/2008 |
| EP | 1 974 685 A1 | 10/2008 |
| EP | 1881804 | 9/2009 |
| EP | 1313406 | 6/2010 |
| EP | 1123130 | 7/2010 |
| EP | 1948030 | 7/2010 |
| EP | 1441649 | 8/2011 |
| EP | 1993621 | 8/2011 |
| EP | 1842490 | 9/2011 |
| EP | 2074953 | 6/2012 |
| EP | 2019633 | 8/2012 |
| EP | 2248471 | 10/2012 |
| EP | 1575421 | 10/2013 |
| EP | 2327429 | 9/2014 |
| EP | 1761296 | 11/2014 |
| EP | 1765225 | 9/2015 |
| EP | 2630919 | 9/2015 |
| EP | 2822656 | 10/2016 |
| EP | 2872051 | 3/2017 |
| EP | 2970572 | 4/2017 |
| EP | 2779910 | 5/2017 |
| EP | 2967852 | 6/2017 |
| EP | 3037043 | 9/2017 |
| EP | 2617386 | 10/2017 |
| EP | 2819585 | 11/2017 |
| EP | 3043746 | 11/2017 |
| EP | 3183012 | 12/2017 |
| EP | 1768604 | 1/2018 |
| EP | 2967869 | 1/2018 |
| EP | 3125780 | 1/2018 |
| EP | 3044221 | 2/2018 |
| EP | 2575678 | 5/2018 |
| EP | 2833836 | 5/2018 |
| EP | 2908744 | 8/2018 |
| EP | 2918251 | 8/2018 |
| EP | 3193791 | 8/2018 |
| EP | 2753246 | 11/2018 |
| EP | 3010446 | 12/2018 |
| EP | 3459469 | 3/2019 |
| EP | 3 620 134 A1 | 3/2020 |
| WO | 95/032018 | 11/1995 |
| WO | 1999/018886 | 4/1999 |
| WO | 2000/012169 | 3/2000 |
| WO | 03/039624 A2 | 5/2003 |
| WO | 2005/092204 A2 | 10/2005 |
| WO | 2011/011765 A2 | 1/2011 |
| WO | 2013/068466 | 5/2013 |
| WO | 2014/085590 A1 | 6/2014 |
| WO | 2016/149653 A2 | 9/2016 |
| WO | 2017/079234 | 5/2017 |
| WO | 2017/161283 | 9/2017 |
| WO | 2021/218549 A1 | 11/2021 |
| WO | 2022/042717 A1 | 3/2022 |
| WO | 2022/042718 A1 | 3/2022 |
| WO | 2022/063137 A1 | 3/2022 |
| WO | 2022/063184 A1 | 3/2022 |

OTHER PUBLICATIONS

Japanese Office Action issued Sep. 27, 2022 in Application No. 516870/2020.
Extended European Search Report issued Dec. 15, 2022 in Application No. 19862977.6.
Indian First Examination Report issued Feb. 3, 2023 in Application No. 202117016867.
Japanese Office Action issued Feb. 14, 2023 in Application No. 516654/2021.
Chinese Office Action issued Feb. 23, 2023 in Application No. 201880061656.0.
Japanese Decision of Refusal issued Jul. 11, 2023 in Application No. 516870/2020.
Chinese Office Action issued Oct. 18, 2023 in Application No. 201880061656.0.
United States Notice of Allowance issued Dec. 5, 2023 in U.S. Appl. No. 17/763,485.
Chinese Office Action issued Jan. 31, 2024 in Application No. 201980072797.7.
Japanese Office Action issued Mar. 12, 2024 in Application No. 2022-519406.
United States Non-Final Rejection issued May 22, 2023 in U.S. Appl. No. 17/763,485.
An International Search Report and a Written Opinion both dated Dec. 4, 2018, which issued during the prosecution of Applicant's PCT/EP2018/075716.
An International Search Report and a Written Opinion both dated Jun. 18, 2019, which issued during the prosecution of Applicant's PCT/US2019/024065.
An International Search Report and a Written Opinion both dated Jul. 6, 2021, which issued during the prosecution of Applicant's PCT/IB2021/052474.
An International Search Report and a Written Opinion both dated Mar. 29, 2021, which issued during the prosecution of Applicant's PCT/IL2020/051041.
European Search Report dated Mar. 12, 2018 which issued during the prosecution of Applicant's European App No. 17192792.4.
An Office Action dated Mar. 7, 2022, which issued during the prosecution of Indian Patent Application No. 202017015683.
An Office Action dated Dec. 22, 2021, which issued during the prosecution of U.S. Appl. No. 16/649,777.
Office Action issued Oct. 1, 2024 in Chinese Patent Application No. 201980072797.7.
Office Action issued Oct. 8, 2024 in Chinese Patent Application No. 202080076880.4.
Office Action issued Apr. 14, 2025 in Chinese Patent Application No. 202080076880.4.

(56) References Cited

OTHER PUBLICATIONS

Office Action dated Oct. 24, 2024 issued in U.S. Appl. No. 17/207,074.

* cited by examiner

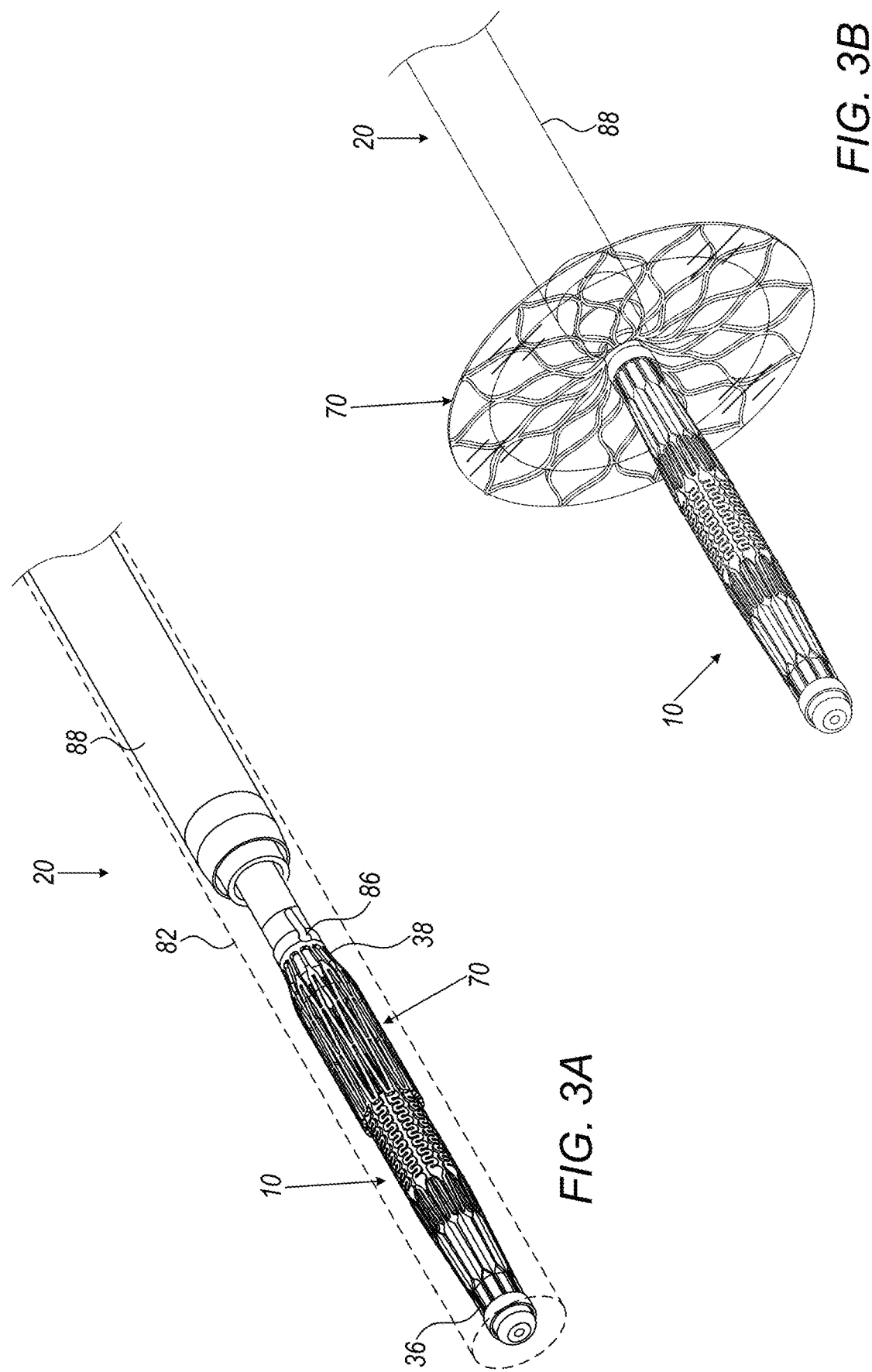

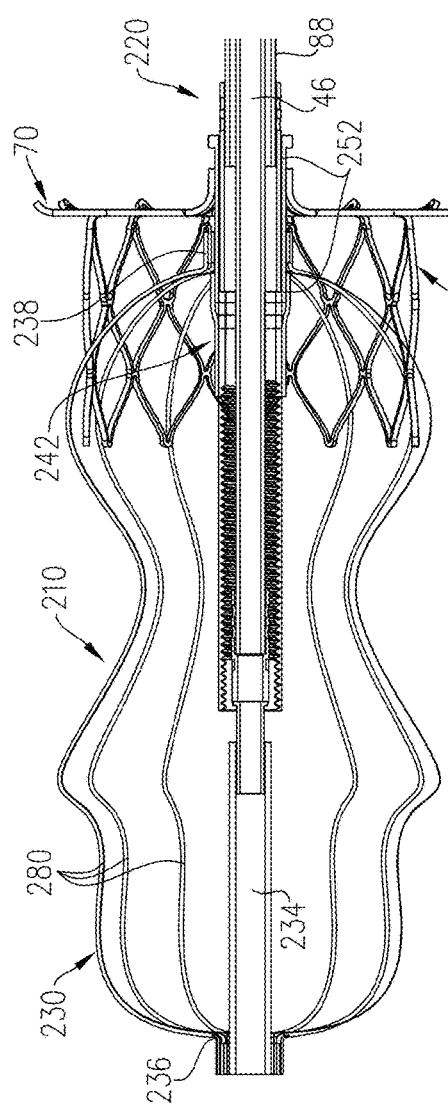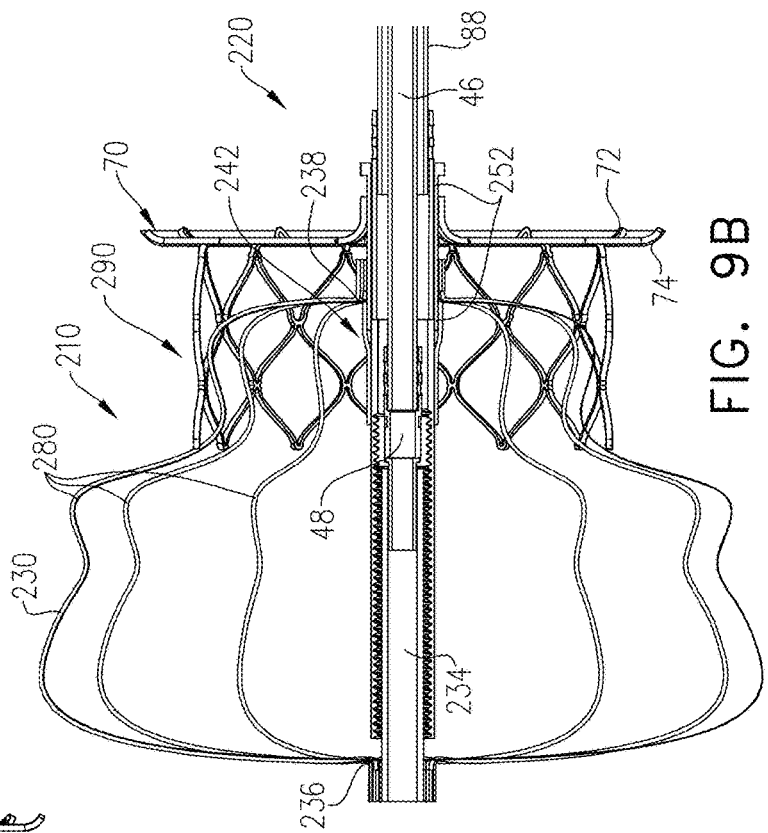

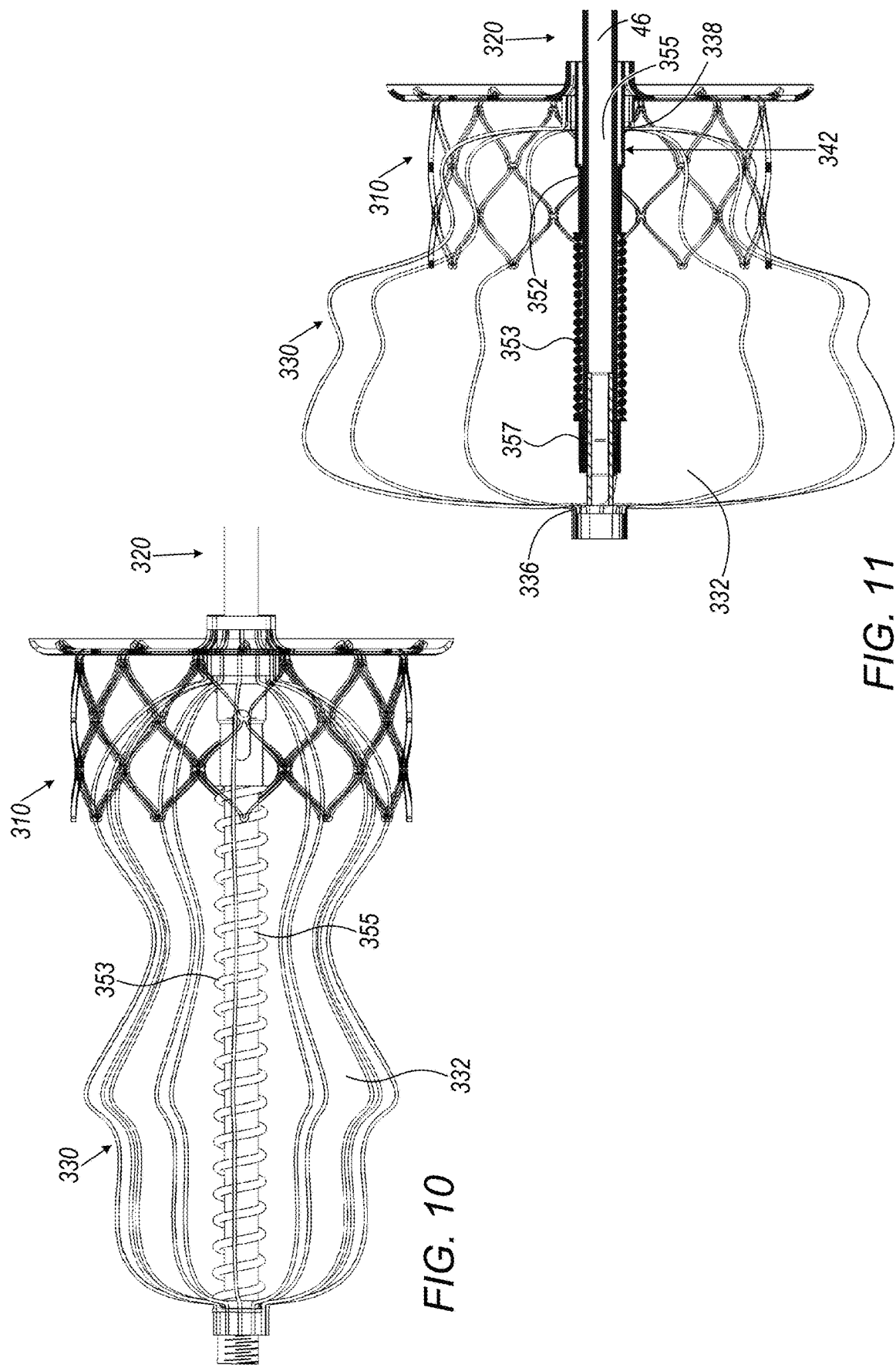

LEFT ATRIAL APPENDAGE OCCLUSION DEVICES

CROSS-REFERENCES TO RELATED APPLICATIONS

The present application is a continuation of U.S. application Ser. No. 17/763,485, filed Mar. 24, 2022, now U.S. Pat. No. 11,944,315, which published as US Patent Application Publication 2022/0370079, and which is the U.S. national stage of International Application PCT/IL2020/051041, filed Sep. 24, 2020, which published as PCT Publication WO 2021/059273 and which claims priority from U.S. Provisional Application 62/906,393, filed Sep. 26, 2019. Each of the above-mentioned applications is assigned to the assignee of the present application and incorporated herein by reference.

FIELD OF THE APPLICATION

The present invention generally relates to an occlusion device for occluding a left atrial appendage.

BACKGROUND OF THE APPLICATION

The left atrial appendage (LAA) is a cavity that presents in the left atrium of the heart. In patients with atrial fibrillation, the passage and steadiness of blood within this cavity can cause thrombus formation, which increases the risk of stroke. Percutaneous LAA occlusion is a therapy for the prevention of stroke in patients with atrial fibrillation. LAA occlusion is used as an alternative to, or in combination with, oral anticoagulant therapy. LAA occlusion has favorable clinical outcomes, but commercially-available devices are typically self-expandable, and not designed to adapt to the LAA anatomy, and thus sometimes result in complications or suboptimal outcomes. In these environments, some of the currently available occlusion devices are limited by the poor adaptability of the device to the defect (lack of conformability) and by a lack of intra-device sealing (due to the high-flow environment).

PCT Publication WO 2019/057950 to Maisano et al. describes an occluder device for occluding a cardiovascular defect or a gap between a medical device and adjacent body tissue, including a compliant balloon defining a fluid-tight balloon chamber and provided with a balloon channel forming a longitudinal passage from a proximal side to a distal side of the balloon; a tip element disposed at the distal side of the balloon, a base element disposed at the proximal side of the balloon, and connecting means comprising at least one connecting strut attached to the tip element and to the base element, the tip element and the base element each having a guide opening substantially coaxial to the balloon channel for slidingly receiving therein a guidewire for the device; elongated actuating means disposed longitudinally slidable in the balloon channel, releasably connectable to the tip element, and longitudinally slidable with respect to the base element; locking means for maintaining a predetermined distance between the tip element and the base element; and proximal connector means for releasably connecting the occluder device to correspondingly configured distal connector means of a catheter device. The balloon includes a fluid port for filling and unfilling a fluid into and from the balloon chamber. An occluder system comprises an occluder device and a catheter device cooperating therewith.

U.S. Pat. No. 6,652,556 to VanTassel et al. describes apparatus for permanent placement across an ostium of a left atrial appendage in a patient, which includes a filtering membrane configured to extend across the ostium of the left atrial appendage. The filtering membrane has a permeable structure which allows blood to flow through but substantially inhibits thrombus from passing therethrough. The apparatus also includes a support structure comprising a plurality of fingers which are radially outwardly expandable with respect to a longitudinal axis to permanently engage the interior wall of the left atrial appendage. The filtering membrane is attached to the support structure extending across the ostium of the left atrial appendage.

SUMMARY OF THE APPLICATION

Some embodiments of the present invention provide occlusion devices for mechanically occluding a left atrial appendage (LAA). The occlusion devices comprise a compliant balloon defining a fluid-tight balloon chamber, and an actuating shaft, which is (a) disposed at least partially within the balloon chamber, (b) connected to a distal end portion of the balloon, and (c) longitudinally moveable with respect to a proximal end portion of the balloon so as to set a distance between the distal and the proximal end portions of the balloon. The occlusion devices also comprise a valve, which can be closed after inflation of the balloon chamber.

The shape and compliancy of the occlusion devices, optionally including plastic deformation of struts thereof, enable anchoring of the occlusion devices and sealing of the LAA while allowing for conformation and adaptation to the geometrical attributes of the LAA, thereby filling the space of the LAA at least to a certain extent, regardless of the particular morphological type of the LAA.

In addition, delivery systems are provided that enable over-the-wire engagement to the LAA, the adjustment of the length and orientation of the occlusion devices during deployment, and the inflation of the balloon chamber with saline or another filling liquid.

The occlusion devices described herein are designed to be delivered into the LAA while longitudinally extended, and either entirely or partially compressed. After delivery, the occlusion devices are adapted to the landing zone anatomy by inflating the balloon chamber and shortening the longitudinal dimension of struts arranged between proximal and distal end portions of the balloon. Under the influence of internal pressure from inflation, the balloon chamber assumes a certain volume which, for a given longitudinal balloon dimension, results in a certain lateral or radial dimension, which provides a good seal between the balloon and the adjacent anatomy of the LAA. Changing the longitudinal balloon dimension, by selecting a different distance between the distal and proximal end portions of the balloon, results in a corresponding change in the radial or lateral extension of the balloon. In other words, shortening the distance between the distal and proximal end portions of the balloon results in a corresponding increase in radial or lateral extension under otherwise constant conditions, which improves the seal with the adjacent tissue of the LAA and inhibits unwanted blood passage. The lateral extension of the balloon is not necessarily symmetric, either because the balloon is not necessarily symmetric and/or because the anatomy against which the balloon is laterally expanded may cause asymmetric balloon expansion. The radial or lateral expansion together include within their scope one or more directions generally perpendicular to the longitudinal axis of the balloon.

In the context of the present disclosure, the terms "distal" and "proximal" are used accordingly to their standard meaning in the field of percutaneous cardiovascular devices. The term "proximal" refers to those components of the device assembly which, when following a delivery catheter during percutaneous delivery, are closer to the end of the catheter that is configured for manipulation by the user (e.g., a catheter handle manipulated by a physician). The term "distal" is used to refer to those components of the device assembly that are more distant from the end of the catheter that is configured for manipulation by the user and/or that are inserted farther into the body of a patient.

The term "compliant" used herein in relation with balloons or with structural components implies a deformability that substantially follows an applied force. Accordingly, a "compliant balloon" means a balloon which progressively expands under the effect of increasing radial pressure as long as a certain burst pressure is not exceeded.

As used herein, the term "strut" means an elongate structural element which can be formed, e.g., a thin wire, rod, or thick-walled tube, all of which do not necessarily have a circular cross section.

There is therefore provided, in accordance with an Inventive Concept 1 of the present invention, an occlusion device for occluding a left atrial appendage (LAA), the occlusion device for use with a delivery system, the occlusion device including:

a compliant balloon defining a fluid-tight balloon chamber;

an actuating shaft, which is (a) disposed at least partially within the balloon chamber, (b) connected to a distal end portion of the balloon, and (c) longitudinally moveable with respect to a proximal end portion of the balloon so as to set a distance between the distal and the proximal end portions of the balloon;

a proximal LAA-orifice cover, which (a) is configured to assume a radially-compressed state and a radially-expanded state, (b) includes a frame and a covering fixed to the frame, and (c) when in the radially-expanded state, is generally orthogonal to the actuating shaft and has a greatest dimension, measured perpendicular to the actuating shaft, of between 10 and 50 mm; and an orifice-support stent, which (a) is fixed to and extends distally from the proximal LAA-orifice cover, (b) is configured to assume a radially-compressed state and a radially-expanded state, and (c) is generally cylindrical when in the radially-expanded state.

Inventive Concept 2. The occlusion device according to Inventive Concept 1, wherein the orifice-support stent, when in the radially-expanded state, has (i) a greatest dimension, measured perpendicular to the actuating shaft, of between 8 and 50 mm, and (ii) an axial length of between 4 and 30 mm.

Inventive Concept 3. The occlusion device according to Inventive Concept 1, wherein the occlusion device further includes a distal tip disposed at the distal end portion of the balloon, wherein the actuating shaft is connected to the distal tip.

Inventive Concept 4. The occlusion device according to Inventive Concept 1, wherein the actuating shaft is shaped so as to define, at least in part, a distal tip disposed at the distal end portion of the balloon.

Inventive Concept 5. The occlusion device according to Inventive Concept 1, wherein the occlusion device further includes a proximal base disposed at the proximal end portion of the balloon, wherein the actuating shaft is moveable with respect to the proximal base.

Inventive Concept 6. The occlusion device according to Inventive Concept 1, for use with a guidewire, wherein the actuating shaft is shaped so as to define a guidewire lumen for slidingly receiving therein the guidewire.

Inventive Concept 7. The occlusion device according to Inventive Concept 1, wherein the compliant balloon includes a compliant material selected from the group consisting of: polycaprolactone (PCL), polyglycolic acid (PGA), polylactic acid (PLA), and polydioxanone (PDO or PDS), silicone, polyurethane, polytetrafluoroethylene (PTFE), polymethylmethacrylate, polyether ether ketone (PEEK), polyvinyl chloride, polyethylene terephthalate, nylon, polyamide, polyamide, and polyether block amide (PEBA).

Inventive Concept 8. The occlusion device according to any one of Inventive Concepts 1-7, wherein the orifice-support stent is not fixed to the balloon, such that a shape of the balloon can change independently of a shape of the orifice-support stent.

Inventive Concept 9. The occlusion device according to any one of Inventive Concepts 1-7, wherein the occlusion device is configured such that inflation of the balloon chamber transitions the orifice-support stent from its radially-compressed state to its radially-expanded state.

Inventive Concept 10. The occlusion device according to any one of Inventive Concepts 1-7, wherein the occlusion device further includes a proximal tube, which is axially fixed with respect to the proximal end portion of the balloon, and wherein the proximal LAA-orifice cover is fixed to the proximal tube radially surrounding the proximal tube, and is indirectly connected to the balloon via the proximal tube and is not directly connected to the balloon.

Inventive Concept 11. The occlusion device according to Inventive Concept 10, wherein the actuating shaft is slidably disposed partially within the proximal tube.

Inventive Concept 12. The occlusion device according to any one of Inventive Concepts 1-7, wherein the occlusion device further includes connecting struts fixed to the distal end portion of the balloon and to the proximal end portion of the balloon.

Inventive Concept 13. The occlusion device according to Inventive Concept 12, wherein the occlusion device is configured such that inflation of the balloon chamber plastically deforms the connecting struts.

Inventive Concept 14. The occlusion device according to Inventive Concept 12, wherein the occlusion device is configured such that shortening of the balloon plastically deforms the connecting struts.

Inventive Concept 15. The occlusion device according to any one of Inventive Concepts 1-7, wherein the balloon has an average wall thickness of between 100 and 5000 microns.

Inventive Concept 16. The occlusion device according to any one of Inventive Concepts 1-7, wherein the balloon has, at a thinnest portion of a wall of the balloon, a thinnest wall thickness of between 20 and 500 microns.

Inventive Concept 17. An occlusion system including the occlusion device according to any one of Inventive Concepts 1-7, the occlusion system further including an implant catheter, in which the occlusion device is releasably disposed in a radially-compressed state, in which a greatest distance between the proximal end portion of the balloon and the distal end portion of the balloon is between 8 and 80 mm.

Inventive Concept 18. The occlusion device according to any one of Inventive Concepts 1-7, further including a valve.

Inventive Concept 19. The occlusion device according to Inventive Concept 18, wherein the occlusion device is shaped so as to define a fluid flow path, and wherein the valve is configured to selectively allow or block fluid flow between the fluid flow path and the balloon chamber when the valve is in open and closed states, respectively.

Inventive Concept 20. The occlusion device according to Inventive Concept 19, wherein the occlusion device is shaped so as to define the fluid flow path along a portion of the actuating shaft, wherein the occlusion device further includes a locking mechanism, which is configured to assume locked and unlocked states, and which is configured, when in the locked state, to maintain, between the distal end portion of the balloon and the proximal end portion of the balloon, the distance set using the actuating shaft, and wherein the occlusion device is configured such that reduction of the distance, by proximal longitudinal movement of the actuating shaft:
  (a) to a first predetermined distance between the distal and the proximal end portions of the balloon automatically transitions the valve from the open state to the closed state, and
  (b) to a second predetermined distance between the distal and the proximal end portions of the balloon automatically transitions the locking mechanism from the unlocked state to the locked state.

Inventive Concept 21. The occlusion device according to Inventive Concept 20, wherein the occlusion device is configured to be releasably connected to the delivery system, and wherein the occlusion device is configured such that the fluid flow path is coupled in fluid communication with the delivery system when the occlusion device is releasably connected to the delivery system.

Inventive Concept 22. The occlusion device according to Inventive Concept 1, wherein the occlusion device further includes a proximal connector that is configured to releasably connect the occlusion device to a correspondingly configured distal connector of the delivery system.

Inventive Concept 23. The occlusion device according to Inventive Concept 22, wherein the proximal connector is shaped so as to define a thread.

Inventive Concept 24. An occlusion system including the occlusion device according to any one of Inventive Concepts 22-23, the occlusion system for use with a guidewire and further including the delivery system cooperating therewith, the delivery system including an implant catheter connected to an operating handle, the implant catheter including a longitudinal passageway for the guidewire, a distal connector for releasably connecting the implant catheter to the correspondingly configured proximal connector of the occlusion device, and an inflation tube channel releasably connectable to the fluid flow path of the occlusion device.

There is further provided, in accordance with an Inventive Concept 25 of the present invention, an occlusion device for occluding a left atrial appendage (LAA), the occlusion device for use with a delivery system, the occlusion device including:
  a compliant balloon defining a fluid-tight balloon chamber;
  an actuating shaft, which is (a) disposed at least partially within the balloon chamber, (b) connected to a distal end portion of the balloon, and (c) longitudinally moveable with respect to a proximal end portion of the balloon so as to set a distance between the distal and the proximal end portions of the balloon;
  a locking mechanism, which is configured to assume locked and unlocked states, and which is configured, when in the locked state, to maintain, between the distal end portion of the balloon and the proximal end portion of the balloon, the distance set using the actuating shaft; and
  a valve,
  wherein the occlusion device is shaped so as to define a fluid flow path along a portion of the actuating shaft,
  wherein the valve is configured to selectively allow or block fluid flow between the fluid flow path and the balloon chamber when the valve is in open and closed states, respectively, and
  wherein the occlusion device is configured such that reduction of the distance, by proximal longitudinal movement of the actuating shaft:
    (a) to a first predetermined distance between the distal and the proximal end portions of the balloon automatically transitions the valve from the open state to the closed state, and
    (b) to a second predetermined distance between the distal and the proximal end portions of the balloon automatically transitions the locking mechanism from the unlocked state to the locked state.

Inventive Concept 26. The occlusion device according to Inventive Concept 25, wherein the first predetermined distance does not equal the second predetermined distance.

Inventive Concept 27. The occlusion device according to Inventive Concept 26, wherein the first predetermined distance is less than the second predetermined distance.

Inventive Concept 28. The occlusion device according to Inventive Concept 25, wherein the first predetermined distance equals the second predetermined distance.

Inventive Concept 29. The occlusion device according to Inventive Concept 25, wherein the occlusion device is configured to be releasably connected to the delivery system, and wherein the occlusion device is configured such that the fluid flow path is coupled in fluid communication with the delivery system when the occlusion device is releasably connected to the delivery system.

Inventive Concept 30. The occlusion device according to Inventive Concept 25, wherein the occlusion device further includes a distal tip disposed at the distal end portion of the balloon, wherein the actuating shaft is connected to the distal tip.

Inventive Concept 31. The occlusion device according to Inventive Concept 25, wherein the actuating shaft is shaped so as to define, at least in part, a distal tip disposed at the distal end portion of the balloon.

Inventive Concept 32. The occlusion device according to Inventive Concept 25, wherein the occlusion device further includes a proximal base disposed at the proximal end portion of the balloon, wherein the actuating shaft is moveable with respect to the proximal base.

Inventive Concept 33. The occlusion device according to Inventive Concept 25, for use with a guidewire, wherein the actuating shaft is shaped so as to define a guidewire lumen for slidingly receiving therein the guidewire.

Inventive Concept 34. The occlusion device according to Inventive Concept 25, wherein the compliant balloon includes a compliant material selected from the group consisting of: polycaprolactone (PCL), polyglycolic acid (PGA), polylactic acid (PLA), and polydioxanone (PDO or PDS), silicone, polyurethane, polytetrafluoroethylene (PTFE), polymethylmethacrylate, polyether ether ketone (PEEK), polyvinyl chloride, polyethylene terephthalate, nylon, polyamide, polyamide, and polyether block amide (PEBA).

Inventive Concept 35. The occlusion device according to any one of Inventive Concepts 25-34, wherein the occlusion device is shaped so as to define the fluid flow path alongside the portion of the actuating shaft.

Inventive Concept 36. The occlusion device according to any one of Inventive Concepts 25-34, wherein the valve is disposed along the actuating shaft.

Inventive Concept 37. The occlusion device according to any one of Inventive Concepts 25-34, wherein the occlusion device further includes a proximal tube, which is axially fixed with respect to the proximal end portion of the balloon, wherein the actuating shaft is slidably disposed partially within the proximal tube.

Inventive Concept 38. The occlusion device according to Inventive Concept 37, wherein the occlusion device is shaped so as to define the fluid flow path along the portion of the actuating shaft radially between an external surface of the actuating shaft and an internal surface of the proximal tube.

Inventive Concept 39. The occlusion device according to Inventive Concept 38, wherein the valve is disposed along the actuating shaft.

Inventive Concept 40. The occlusion device according to Inventive Concept 39, wherein the valve includes a seal around at least a portion of the external surface of the actuating shaft, and wherein the valve is configured to assume the open state when the seal is disposed at one or more first axial positions with respect to the proximal tube, and the closed state when the seal is disposed at one or more second axial positions with respect to the proximal tube, the one or more second axial positions proximal to the one or more first axial positions.

Inventive Concept 41. The occlusion device according to Inventive Concept 40, wherein the seal, the actuating shaft, and the proximal tube are arranged such that the seal blocks fluid flow out of a distal end of the proximal tube at least when the seal is disposed at the one or more first axial positions with respect to the proximal tube.

Inventive Concept 42. The occlusion device according to Inventive Concept 38, wherein a wall of the proximal tube is shaped so as to define one or more tabs through the wall, wherein the one or more tabs are biased to flex radially inward, and wherein, when the valve is in the open state, the fluid flow path passes through the wall between respective proximal ends of the one or more tabs and a non-tabbed portion of the wall axially adjacent the one or more tabs.

Inventive Concept 43. The occlusion device according to Inventive Concept 42, wherein the non-tabbed portion of the wall is disposed proximal to the one or more tabs.

Inventive Concept 44. The occlusion device according to Inventive Concept 42, wherein the external surface of the actuating shaft is shaped so as to define one or more protrusions around at least a portion of the actuating shaft, and wherein the proximal ends of the one or more tabs are shaped so as to prevent distal movement of the one or more protrusions when the one or more protrusions are disposed proximal to the proximal ends of the one or more tabs, thereby causing the locking mechanism to assume the locked state.

Inventive Concept 45. The occlusion device according to Inventive Concept 37, wherein the occlusion device further includes a proximal LAA-orifice cover, which (a) is fixed to the proximal tube radially surrounding the proximal tube, (b) is configured to assume a radially-compressed state and a radially-expanded state, (c) includes a frame and a covering fixed to the frame, (d) when in the radially-expanded state, is generally orthogonal to the proximal tube and has a greatest dimension, measured perpendicular to the proximal tube, of between 10 and 50 mm, and (e) is indirectly connected to the balloon via the proximal tube and is not directly connected to the balloon.

Inventive Concept 46. The occlusion device according to Inventive Concept 45, wherein the occlusion device further includes an orifice-support stent, which (a) is fixed to and extends distally from the proximal LAA-orifice cover, (b) is configured to assume a radially-compressed state and a radially-expanded state, and (c) is generally cylindrical when in the radially-expanded state.

Inventive Concept 47. The occlusion device according to Inventive Concept 46, wherein the orifice-support stent, when in the radially-expanded state, has (i) a greatest dimension, measured perpendicular to the actuating shaft, of between 8 and 50 mm, and (ii) an axial length of between 4 and 30 mm.

Inventive Concept 48. The occlusion device according to any one of Inventive Concepts 25-34, wherein the occlusion device further includes connecting struts fixed to the distal end portion of the balloon and to the proximal end portion of the balloon.

Inventive Concept 49. The occlusion device according to Inventive Concept 48, wherein the occlusion device is configured such that inflation of the balloon chamber plastically deforms the connecting struts.

Inventive Concept 50. The occlusion device according to Inventive Concept 48, wherein the occlusion device is configured such that shortening of the balloon plastically deforms the connecting struts.

Inventive Concept 51. The occlusion device according to any one of Inventive Concepts 25-34, wherein the balloon has an average wall thickness of between 100 and 5000 microns.

Inventive Concept 52. The occlusion device according to any one of Inventive Concepts 25-34, wherein the balloon has, at a thinnest portion of a wall of the balloon, a thinnest wall thickness of between 20 and 500 microns.

Inventive Concept 53. An occlusion system including the occlusion device according to any one of Inventive Concepts 25-34, the occlusion system further including an implant catheter, in which the occlusion device is releasably disposed in a radially-compressed state, in which a greatest distance between the proximal end portion of the balloon and the distal end portion of the balloon is between 8 and 80 mm.

Inventive Concept 54. The occlusion device according to any one of Inventive Concepts 25-34, wherein the occlusion device further includes a proximal connector that is configured to releasably connect the occlusion device to a correspondingly configured distal connector of the delivery system.

Inventive Concept 55. The occlusion device according to Inventive Concept 54, wherein the proximal connector is shaped so as to define a thread.

Inventive Concept 56. An occlusion system including the occlusion device according to any one of Inventive Concepts 25-34, the occlusion system for use with a guidewire and further including the delivery system cooperating therewith, the delivery system including an implant catheter connected to an operating handle, the implant catheter including a longitudinal passageway for the guidewire, a distal connector for releasably connecting the implant catheter to the correspondingly configured proximal connector of the occlusion device, and an inflation tube channel releasably connectable to the fluid flow path of the occlusion device.

There is still further provided, in accordance with an Inventive Concept 57 of the present invention, an occlusion device for occluding a left atrial appendage (LAA), the occlusion device for use with a delivery system, the occlusion device including:
a compliant balloon defining a fluid-tight balloon chamber;
an actuating shaft, which is (a) disposed at least partially within the balloon chamber, (b) connected to a distal end portion of the balloon, and (c) longitudinally moveable with respect to a proximal end portion of the balloon so as to set a distance between the distal and the proximal end portions of the balloon; and
connecting struts fixed to the distal end portion of the balloon and to the proximal end portion of the balloon, wherein the connecting struts include:
first lateral portions arranged along a lateral surface of the balloon,
second distal-end portions arranged on a distal surface of the balloon,
third proximal-end portions arranged on a proximal surface of the balloon, and
distal end portions that join the second distal-end portions of the struts to the distal end portion of the balloon, respectively, and have a serpentine shape, wherein the occlusion device is configured such that upon inflation of the balloon chamber, the distal end portions are curved.

Inventive Concept 58. The occlusion device according to Inventive Concept 57, wherein the connecting struts include proximal end portions that join the third proximal-end portions of the struts to the proximal end portion of the balloon, respectively, and have a serpentine shape, and wherein the occlusion device is configured such that upon inflation of the balloon chamber, the proximal end portions are curved.

Inventive Concept 59. The occlusion device according to Inventive Concept 57, wherein the connecting struts include distal interface portions that join the first lateral portions and the second distal-end portions, respectively, and have a serpentine shape, and wherein the occlusion device is configured such that upon inflation of the balloon chamber, the distal interface portions are curved.

Inventive Concept 60. The occlusion device according to Inventive Concept 57, wherein the connecting struts include proximal interface portions that join the first lateral portions and the third proximal-end portions, respectively, and have a serpentine shape, and wherein the occlusion device is configured such that upon inflation of the balloon chamber, the proximal interface portions are curved.

Inventive Concept 61. The occlusion device according to Inventive Concept 57, wherein the first lateral portions of the struts are generally straight.

Inventive Concept 62. The occlusion device according to Inventive Concept 57, wherein the second distal-end portions and the third proximal-end portions are generally straight.

Inventive Concept 63. The occlusion device according to Inventive Concept 57, wherein the first lateral portions of the struts are generally straight, and the second distal-end portions and the third proximal-end portions are generally straight.

Inventive Concept 64. The occlusion device according to Inventive Concept 57, wherein the occlusion device is configured such that inflation of the balloon chamber plastically deforms the connecting struts.

Inventive Concept 65. The occlusion device according to Inventive Concept 57, wherein the occlusion device is configured such that shortening of the balloon plastically deforms the connecting struts.

Inventive Concept 66. The occlusion device according to any one of Inventive Concepts 57-65,
wherein the distal interface portions are shaped so as to define respective pairs of parallel serpentine struts that define respective narrow elongate gaps therebetween, and
wherein the struts are shaped so as to define a plurality of spikes, which:
extend from outer ends of the second distal-end portions, respectively,
are disposed in the respective narrow elongate gaps, generally axially oriented, when the balloon is in a non-inflated, elongate configuration, and
are configured to extend more radially upon inflation of the balloon chamber to serve as tissue-engaging barbs.

Inventive Concept 67. The occlusion device according to any one of Inventive Concepts 57-65, wherein the connecting struts further include closed stent cells that connect adjacent pairs of the first lateral portions.

Inventive Concept 68. The occlusion device according to Inventive Concept 67, wherein two or more of the closed stent cells arranged in series connect the adjacent pairs of the first lateral portions.

Inventive Concept 69. The occlusion device according to Inventive Concept 67, wherein the closed stent cells are shaped as respective rhombuses.

Inventive Concept 70. The occlusion device according to Inventive Concept 67, wherein the first lateral portions are oriented parallel to a central longitudinal axis of the occlusion device.

Inventive Concept 71. The occlusion device according to Inventive Concept 67, wherein an average width of the struts of first lateral portions equals at least 200% of an average width of the struts of the closed stent cells.

There is additionally provided, in accordance with an Inventive Concept 72 of the present invention, an occlusion device for occluding a left atrial appendage (LAA), the occlusion device for use with a delivery system, the occlusion device including:
a compliant balloon defining a fluid-tight balloon chamber;
an actuating shaft, which is (a) disposed at least partially within the balloon chamber, (b) connected to a distal end portion of the balloon, and (c) longitudinally moveable with respect to a proximal end portion of the balloon so as to set a distance between the distal and the proximal end portions of the balloon; and
connecting struts fixed to the distal end portion of the balloon and to the proximal end portion of the balloon, wherein the connecting struts include:
first lateral portions arranged along a lateral surface of the balloon,
second distal-end portions arranged on a distal surface of the balloon,
third proximal-end portions arranged on a proximal surface of the balloon, and
distal interface portions that join the first lateral portions and the second distal-end portions, respectively, and have a serpentine shape, wherein the occlusion device is configured such that upon inflation of the balloon chamber, the distal interface portions are curved.

Inventive Concept 73. The occlusion device according to Inventive Concept 72, wherein the connecting struts include proximal interface portions that join the first lateral portions and the third proximal-end portions, respectively, and have a serpentine shape, and wherein the occlusion device is configured such that upon inflation of the balloon chamber, the proximal interface portions are curved.

Inventive Concept 74. The occlusion device according to Inventive Concept 72, wherein the first lateral portions of the struts are generally straight.

Inventive Concept 75. The occlusion device according to Inventive Concept 72, wherein the second distal-end portions and the third proximal-end portions are generally straight.

Inventive Concept 76. The occlusion device according to Inventive Concept 72, wherein the first lateral portions of the struts are generally straight, and the second distal-end portions and the third proximal-end portions are generally straight.

Inventive Concept 77. The occlusion device according to Inventive Concept 72, wherein the occlusion device is configured such that inflation of the balloon chamber plastically deforms the connecting struts.

Inventive Concept 78. The occlusion device according to Inventive Concept 72, wherein the occlusion device is configured such that shortening of the balloon plastically deforms the connecting struts.

Inventive Concept 79. The occlusion device according to Inventive Concept 72, wherein the connecting struts include distal end portions that join the second distal-end portions of the struts to the distal end portion of the balloon, respectively, and have a serpentine shape, and wherein the occlusion device is configured such that upon inflation of the balloon chamber, the distal end portions are curved.

Inventive Concept 80. The occlusion device according to Inventive Concept 72, wherein the connecting struts include proximal end portions that join the third proximal-end portions of the struts to the proximal end portion of the balloon, respectively, and have a serpentine shape, and wherein the occlusion device is configured such that upon inflation of the balloon chamber, the proximal end portions are curved.

Inventive Concept 81. The occlusion device according to any one of Inventive Concepts 72-80,
wherein the distal interface portions are shaped so as to define respective pairs of parallel serpentine struts that define respective narrow elongate gaps therebetween, and
wherein the struts are shaped so as to define a plurality of spikes, which:
extend from outer ends of the second distal-end portions, respectively,
are disposed in the respective narrow elongate gaps, generally axially oriented, when the balloon is in a non-inflated, elongate configuration, and
are configured to extend more radially upon inflation of the balloon chamber to serve as tissue-engaging barbs.

Inventive Concept 82. The occlusion device according to any one of Inventive Concepts 72-80, wherein the connecting struts further include closed stent cells that connect adjacent pairs of the first lateral portions.

Inventive Concept 83. The occlusion device according to Inventive Concept 82, wherein two or more of the closed stent cells arranged in series connect the adjacent pairs of the first lateral portions.

Inventive Concept 84. The occlusion device according to Inventive Concept 82, wherein the closed stent cells are shaped as respective rhombuses.

Inventive Concept 85. The occlusion device according to Inventive Concept 82, wherein the first lateral portions are oriented parallel to a central longitudinal axis of the occlusion device.

Inventive Concept 86. The occlusion device according to Inventive Concept 82, wherein an average width of the struts of first lateral portions equals at least 200% of an average width of the struts of the closed stent cells.

There is yet additionally provided, in accordance with an Inventive Concept 87 of the present invention, an occlusion device for occluding a left atrial appendage (LAA), the occlusion device for use with a delivery system, the occlusion device including:
a compliant balloon defining a fluid-tight balloon chamber;
an actuating shaft, which is (a) disposed at least partially within the balloon chamber, (b) connected to a distal end portion of the balloon, and (c) longitudinally moveable with respect to a proximal end portion of the balloon so as to set a distance between the distal and the proximal end portions of the balloon; and
connecting struts fixed to the distal end portion of the balloon and to the proximal end portion of the balloon, wherein the connecting struts include:
first lateral portions arranged along a lateral surface of the balloon, and
closed stent cells that connect adjacent pairs of the first lateral portions.

Inventive Concept 88. The occlusion device according to Inventive Concept 87, wherein two or more of the closed stent cells arranged in series connect the adjacent pairs of the first lateral portions.

Inventive Concept 89. The occlusion device according to Inventive Concept 87, wherein the closed stent cells are shaped as respective rhombuses.

Inventive Concept 90. The occlusion device according to Inventive Concept 87, wherein the first lateral portions are oriented parallel to a central longitudinal axis of the occlusion device.

Inventive Concept 91. The occlusion device according to Inventive Concept 87, wherein an average width of the struts of first lateral portions equals at least 200% of an average width of the struts of the closed stent cells.

There is also provided, in accordance with an Inventive Concept 92 of the present invention, a method for occluding a left atrial appendage (LAA) of a patient, the method including:
using a delivery system, positioning:
a compliant balloon of an occlusion device in a longitudinally extended form thereof in the LAA,
an actuating shaft of the occlusion device in the LAA, wherein the actuating shaft is (a) disposed at least partially within the balloon chamber, (b) connected to a distal end portion of the balloon, and (c) longitudinally moveable with respect to a proximal end portion of the balloon so as to set a distance between the distal and the proximal end portions of the balloon,
a proximal LAA-orifice cover in a left atrium outside the LAA, against an atrial wall surrounding an orifice of the LAA, wherein the proximal LAA-orifice cover is (a) configured to assume a radially-compressed state and a radially-expanded state, (b) includes a frame and a covering fixed to the frame, and (c) when in the radially-expanded state, is generally orthogonal to the actuating shaft and has a greatest dimension, measured perpendicular to the actuating shaft, of between 10 and 50 mm, and an orifice-support stent at least partially in the LAA, wherein the orifice-support stent is (a) fixed to and extending distally from the proximal LAA-orifice cover, (b) configured to assume a radially-compressed state and a radially-expanded state, and (c) generally cylindrical when in the radially-expanded state;

inflating the compliant balloon by filling, via a fluid flow path along a portion of the actuating shaft, a fluid into the balloon chamber;

expanding the balloon in a radial or a lateral direction by shortening the distance between the distal and the proximal end portions of the balloon to a desired distance; and releasing the occlusion device from the delivery system.

Inventive Concept 93. The method according to Inventive Concept 92, wherein the orifice-support stent is not fixed to the balloon, such that a shape of the balloon can change independently of a shape of the orifice-support stent.

Inventive Concept 94. The method according to Inventive Concept 92, wherein inflating the compliant balloon transitions the orifice-support stent from its radially-compressed state to its radially-expanded state.

There is further provided, in accordance with an Inventive Concept 95 of the present invention, a method for occluding a left atrial appendage (LAA) of a patient, the method including:

using a delivery system, positioning a compliant balloon of an occlusion device in a longitudinally extended form thereof in the LAA;

inflating the compliant balloon by filling, via a fluid flow path along a portion of an actuating shaft of the occlusion device, a fluid into a fluid-tight balloon chamber defined by the balloon, while a valve of the occlusion device in an open state in which the valve allows fluid flow between the fluid flow path and the balloon chamber, wherein the actuating shaft is (a) disposed at least partially within the balloon chamber, (b) connected to a distal end portion of the balloon, and (c) longitudinally moveable with respect to a proximal end portion of the balloon so as to set a distance between the distal and the proximal end portions of the balloon;

expanding the balloon in a radial or a lateral direction by shortening the distance between the distal and the proximal end portions of the balloon to a desired distance, by proximally longitudinally moving the actuating shaft:

(a) to a first predetermined distance between the distal and the proximal end portions of the balloon, which automatically transitions the valve from the open state to a closed state in which the valve blocks fluid flow between the fluid flow path and the balloon chamber, and (b) to a second predetermined distance between the distal and the proximal end portions of the balloon, which automatically transitions a locking mechanism from an unlocked state to a locked state, in which the locking mechanism maintains, between the distal end portion of the balloon and the proximal end portion of the balloon, the distance set using the actuating shaft; and releasing the occlusion device from the delivery system.

Inventive Concept 96. The method according to Inventive Concept 95, wherein positioning the balloon in the LAA includes:

advancing a guidewire into a body of the patient using the delivery system; and advancing the occlusion device over the guidewire.

Inventive Concept 97. The method according to Inventive Concept 95, wherein the first predetermined distance does not equal the second predetermined distance.

Inventive Concept 98. The method according to Inventive Concept 97, wherein the first predetermined distance is less than the second predetermined distance.

Inventive Concept 99. The method according to Inventive Concept 95, wherein the first predetermined distance equals the second predetermined distance.

Inventive Concept 100. The method according to Inventive Concept 95, wherein the occlusion device is shaped so as to define the fluid flow path alongside the portion of the actuating shaft.

Inventive Concept 101. The method according to Inventive Concept 95, wherein the valve is disposed along the actuating shaft.

Inventive Concept 102. The method according to Inventive Concept 95, wherein the occlusion device further includes a proximal tube, which is axially fixed with respect to the proximal end portion of the balloon, wherein the actuating shaft is slidably disposed partially within the proximal tube.

Inventive Concept 103. The method according to Inventive Concept 102, wherein the occlusion device is shaped so as to define the fluid flow path along the portion of the actuating shaft radially between an external surface of the actuating shaft and an internal surface of the proximal tube.

Inventive Concept 104. The method according to Inventive Concept 103, wherein the valve is disposed along the actuating shaft.

Inventive Concept 105. The method according to Inventive Concept 104, wherein the valve includes a seal around at least a portion of the external surface of the actuating shaft, and wherein the valve is configured to assume the open state when the seal is disposed at one or more first axial positions with respect to the proximal tube, and the closed state when the seal is disposed at one or more second axial positions with respect to the proximal tube, the one or more second axial positions proximal to the one or more first axial positions.

Inventive Concept 106. The method according to Inventive Concept 105, wherein the seal, the actuating shaft, and the proximal tube are arranged such that the seal blocks fluid flow out of a distal end of the proximal tube at least when the seal is disposed at the one or more first axial positions with respect to the proximal tube.

Inventive Concept 107. The method according to Inventive Concept 103, wherein a wall of the proximal tube is shaped so as to define one or more tabs through the wall, wherein the one or more tabs are biased to flex radially inward, and wherein, when the valve is in the open state, the fluid flow path passes through the wall between respective proximal ends of the one or more tabs and a non-tabbed portion of the wall axially adjacent the one or more tabs.

Inventive Concept 108. The method according to Inventive Concept 107, wherein the non-tabbed portion of the wall is disposed proximal to the one or more tabs.

Inventive Concept 109. The method according to Inventive Concept 107, wherein the external surface of the actuating shaft is shaped so as to define one or more protrusions around at least a portion of the actuating shaft, and wherein the proximal ends of the one or more tabs are shaped so as to prevent distal movement of the one or more protrusions when the one or more protrusions are disposed proximal to the proximal ends of the one or more tabs, thereby causing the locking mechanism to assume the locked state.

Inventive Concept 110. The method according to Inventive Concept 102, wherein the occlusion device further includes a proximal LAA-orifice cover, which (a) is fixed to the proximal tube radially surrounding the proximal tube, (b) is configured to assume a radially-compressed state and a radially-expanded state, (c) includes a frame and a covering fixed to the frame, (d) when in the radially-expanded state, is generally orthogonal to the proximal tube and has a greatest dimension, measured perpendicular to the proximal tube, of between 10 and 50 mm, and (e) is indirectly connected to the balloon via the proximal tube and is not directly connected to the balloon.

Inventive Concept 111. The method according to Inventive Concept 110, wherein the occlusion device further includes an orifice-support stent, which (a) is fixed to and extends distally from the proximal LAA-orifice cover, (b) is configured to assume a radially-compressed state and a radially-expanded state, and (c) is generally cylindrical when in the radially-expanded state.

Inventive Concept 112. The method according to Inventive Concept 111, wherein the orifice-support stent, when in the radially-expanded state, has (i) a greatest dimension, measured perpendicular to the actuating shaft, of between 8 and 50 mm, and (ii) an axial length of between 4 and 30 mm.

Inventive Concept 113. The method according to Inventive Concept 95, wherein the occlusion device further includes connecting struts fixed to the distal end portion of the balloon and to the proximal end portion of the balloon.

Inventive Concept 114. The method according to Inventive Concept 113, wherein the occlusion device is configured such that inflation of the balloon chamber plastically deforms the connecting struts.

Inventive Concept 115. The method according to Inventive Concept 113, wherein the occlusion device is configured such that shortening of the balloon plastically deforms the connecting struts.

There is still further provided, in accordance with an Inventive Concept 116 of the present invention, apparatus for occluding a left atrial appendage (LAA), the apparatus including:

(i) an occlusion device, including:
a compliant balloon defining a fluid-tight balloon chamber;
an actuating shaft, which is (a) disposed at least partially within the balloon chamber, (b) connected to a distal end portion of the balloon, and (c) longitudinally moveable with respect to a proximal end portion of the balloon so as to set a distance between the distal and the proximal end portions of the balloon; and
a valve, including an elastomer sleeve that surrounds a portion of the actuating shaft,
wherein the occlusion device is shaped so as to define a fluid flow path having one or more fluid-flow-path openings to the balloon chamber, and
wherein the elastomer sleeve is configured to have a resting state in which the sleeve covers and seals the one or more fluid-flow-path openings, such that the valve is in a closed state; and (ii) a delivery system, which is configured to be releasably connected to the occlusion device, and which includes a valve-opening prop, which is configured:
(a) when in a propping position, to prop open and deform the elastomer sleeve such that the elastomer sleeve does not seal the one or more fluid-flow-path openings and the valve is in an open state, and
(b) when in a non-propping position, not to prop open the elastomer sleeve, such that elastomer sleeve assumes the resting state and the valve is in the closed state.

Inventive Concept 117. The apparatus according to Inventive Concept 116, wherein the valve-opening prop includes one or more tabs that extend radially outward from an axis of the elastomer sleeve, so as to prop open the elastomer sleeve.

Inventive Concept 118. The apparatus according to Inventive Concept 116, wherein the valve-opening prop is configured such that axial sliding thereof with respect to the elastomer sleeve transitions the valve-opening prop from the propping position to the non-propping position.

Inventive Concept 119. The apparatus according to Inventive Concept 116, wherein the occlusion device further includes a locking mechanism, which is configured to assume locked and unlocked states, and which is configured, when in the locked state, to maintain, between the distal end portion of the balloon and the proximal end portion of the balloon, the distance set using the actuating shaft.

Inventive Concept 120. The apparatus according to Inventive Concept 116, wherein the occlusion device is configured to be releasably connected to the delivery system, and wherein the occlusion device is configured such that the fluid flow path is coupled in fluid communication with the delivery system when the occlusion device is releasably connected to the delivery system.

Inventive Concept 121. The apparatus according to Inventive Concept 116, wherein the occlusion device further includes a distal tip disposed at the distal end portion of the balloon, wherein the actuating shaft is connected to the distal tip.

Inventive Concept 122. The apparatus according to Inventive Concept 116, wherein the actuating shaft is shaped so as to define, at least in part, a distal tip disposed at the distal end portion of the balloon.

Inventive Concept 123. The apparatus according to Inventive Concept 116, wherein the occlusion device further includes a proximal base disposed at the proximal end portion of the balloon, wherein the actuating shaft is longitudinally moveable with respect to the proximal base.

Inventive Concept 124. The apparatus according to Inventive Concept 116, for use with a guidewire, wherein the actuating shaft is shaped so as to define a guidewire lumen for slidingly receiving therein the guidewire.

Inventive Concept 125. The apparatus according to Inventive Concept 116, wherein the compliant balloon includes a compliant material selected from the group consisting of: polycaprolactone (PCL), polyglycolic acid (PGA), polylactic acid (PLA), and polydioxanone (PDO or PDS), silicone, polyurethane, polytetrafluoroethylene (PTFE), polymethylmethacrylate, polyether ether ketone (PEEK), polyvinyl chloride, polyethylene terephthalate, nylon, polyamide, polyamide, and polyether block amide (PEBA).

Inventive Concept 126. The apparatus according to any one of Inventive Concepts 116-125, wherein the occlusion device further includes a proximal tube, which is axially fixed with respect to the proximal end portion of the balloon.

Inventive Concept 127. The apparatus according to Inventive Concept 126, wherein the actuating shaft is slidably disposed partially within the proximal tube.

Inventive Concept 128. The apparatus according to Inventive Concept 118, wherein the valve-opening prop includes a tubular portion, which is disposed at least partially within the proximal tube.

Inventive Concept 129. The apparatus according to Inventive Concept 128, wherein the valve-opening prop includes one or more tabs that extend (a) axially away from the tubular portion and (b) radially outward from the proximal tube, so as to prop open the elastomer sleeve.

Inventive Concept 130. The apparatus according to Inventive Concept 129, wherein the one or more tabs pass through at least a portion of the one or more fluid-flow-path openings when the valve-opening prop is in the propping position.

Inventive Concept 131. The apparatus according to Inventive Concept 129, wherein the proximal tube is shaped so as to define one or more access openings through a wall of the proximal tube, and wherein the one or more tabs pass through the one or more access openings at least when the valve-opening prop is in the propping position.

Inventive Concept 132. The apparatus according to Inventive Concept 126, wherein the occlusion device further includes a proximal LAA-orifice cover, which (a) is fixed to the proximal tube radially surrounding the proximal tube, (b) is configured to assume a radially-compressed state and a radially-expanded state, (c) includes a frame and a covering fixed to the frame, (d) when in the radially-expanded state, is generally orthogonal to the proximal tube and has a greatest dimension, measured perpendicular to the proximal tube, of between 10 and 50 mm, and (e) is indirectly connected to the balloon via the proximal tube and is not directly connected to the balloon.

Inventive Concept 133. The apparatus according to Inventive Concept 132, wherein the occlusion device further includes an orifice-support stent, which (a) is fixed to and extends distally from the proximal LAA-orifice cover, (b) is configured to assume a radially-compressed state and a radially-expanded state, and (c) is generally cylindrical when in the radially-expanded state.

Inventive Concept 134. The apparatus according to Inventive Concept 133, wherein the orifice-support stent, when in the radially-expanded state, has (i) a greatest dimension, measured perpendicular to the actuating shaft, of between 8 and 50 mm, and (ii) an axial length of between 4 and 30 mm.

Inventive Concept 135. The apparatus according to any one of Inventive Concepts 116-125, wherein the occlusion device further includes connecting struts fixed to the distal end portion of the balloon and to the proximal end portion of the balloon.

Inventive Concept 136. The apparatus according to Inventive Concept 135, wherein the occlusion device is configured such that inflation of the balloon chamber plastically deforms the connecting struts.

Inventive Concept 137. The apparatus according to Inventive Concept 135, wherein the occlusion device is configured such that shortening of the balloon plastically deforms the connecting struts.

Inventive Concept 138. The apparatus according to any one of Inventive Concepts 116-125, wherein the balloon has an average wall thickness of between 100 and 5000 microns.

Inventive Concept 139. The apparatus according to any one of Inventive Concepts 116-125, wherein the balloon has, at a thinnest portion of a wall of the balloon, a thinnest wall thickness of between 20 and 500 microns.

Inventive Concept 140. The apparatus according to any one of Inventive Concepts 116-125, wherein the delivery system further including an implant catheter, in which the occlusion device is releasably disposed in a radially-compressed state, in which a greatest distance between the proximal end portion of the balloon and the distal end portion of the balloon is between 8 and 80 mm.

Inventive Concept 141. The apparatus according to any one of Inventive Concepts 116-125, wherein the occlusion device further includes a proximal connector that is configured to releasably connect the occlusion device to a correspondingly configured distal connector of the delivery system.

Inventive Concept 142. The apparatus according to Inventive Concept 141, wherein the proximal connector is shaped so as to define a thread.

Inventive Concept 143. The apparatus according to any one of Inventive Concepts 116-125, for use with a guidewire, wherein the delivery system includes an implant catheter connected to an operating handle, the implant catheter including a longitudinal passageway for the guidewire, a distal connector for releasably connecting the implant catheter to the correspondingly configured proximal connector of the occlusion device, and an inflation tube channel releasably connectable to the fluid flow path of the occlusion device.

There is additionally provided, in accordance with an Inventive Concept 144 of the present invention, apparatus for occluding a left atrial appendage (LAA), the apparatus including:
  (i) an occlusion device, including:
    a compliant balloon defining a fluid-tight balloon chamber;
    an actuating shaft, which is (a) disposed at least partially within the balloon chamber, (b) connected to a distal end portion of the balloon, and (c) longitudinally moveable with respect to a proximal end portion of the balloon so as to set a distance between the distal and the proximal end portions of the balloon; and
    a valve, including an elastomer sleeve that surrounds a portion of the actuating shaft,
    wherein the occlusion device is shaped so as to define a fluid flow path having one or more fluid-flow-path openings to the balloon chamber, and
    wherein the elastomer sleeve is configured to have a resting state in which the sleeve covers and seals the one or more fluid-flow-path openings, such that the valve is in a closed state; and
  (ii) a delivery system, which is configured to be releasably connected to the occlusion device, and which includes one or more guidewires, which:
    (a) when in a propping position, prop open and deform the elastomer sleeve such that the elastomer sleeve does not seal the one or more fluid-flow-path openings and the valve is in an open state, and
    (b) when in a non-propping position, do not prop open the elastomer sleeve, such that elastomer sleeve assumes the resting state and the valve is in the closed state.

Inventive Concept 145. The apparatus according to Inventive Concept 144, wherein the one or more guidewires pass through at least a portion of the one or more fluid-flow-path openings when the one or more guidewires are in the propping position.

Inventive Concept 146. The apparatus according to any one of Inventive Concepts 144-145, wherein the occlusion device further includes a proximal tube, which is axially fixed with respect to the proximal end portion of the balloon.

Inventive Concept 147. The apparatus according to Inventive Concept 146, wherein the actuating shaft is slidably disposed partially within the proximal tube.

Inventive Concept 148. The apparatus according to Inventive Concept 146, wherein the occlusion device further includes a proximal LAA-orifice cover, which (a) is fixed to the proximal tube radially surrounding the proximal tube, (b) is configured to assume a radially-compressed state and a radially-expanded state, (c) includes a frame and a covering fixed to the frame, (d) when in the radially-expanded state, is generally orthogonal to the proximal tube and has a greatest dimension, measured perpendicular to the proximal tube, of between 10 and 50 mm, and (e) is indirectly connected to the balloon via the proximal tube and is not directly connected to the balloon.

Inventive Concept 149. The apparatus according to Inventive Concept 148, wherein the occlusion device further includes an orifice-support stent, which (a) is fixed to and extends distally from the proximal LAA-orifice cover, (b) is configured to assume a radially-compressed state and a radially-expanded state, and (c) is generally cylindrical when in the radially-expanded state.

Inventive Concept 150. The apparatus according to Inventive Concept 149, wherein the orifice-support stent, when in the radially-expanded state, has (i) a greatest dimension, measured perpendicular to the actuating shaft, of between 8 and 50 mm, and (ii) an axial length of between 4 and 30 mm.

There is yet additionally provided, in accordance with an Inventive Concept 151 of the present invention, apparatus for occluding a left atrial appendage (LAA), the apparatus including:

(i) an occlusion device, including:
a compliant balloon defining a fluid-tight balloon chamber;
a proximal tube, which is axially fixed with respect to a proximal end portion of the balloon; and
a spring, which is (a) disposed at least partially within the balloon chamber, (b) connected to a distal end portion of the balloon and the proximal tube, and (c) has a relaxed length, wherein when the spring has the relaxed length, the distal end portion of the balloon is at a relaxed distance from the proximal end portion of the balloon; and (ii) a delivery system, which is configured to be releasably connected to the occlusion device, and which includes a stylet, which is removably disposed through the proximal tube and within the spring, wherein the occlusion device is configured such that a degree of distal advancement of the stylet within the spring sets a tensed length of the spring, which in turn sets a tensed distance between the distal and the proximal end portions of the balloon, the tensed distance greater than the relaxed distance.

Inventive Concept 152. The apparatus according to Inventive Concept 151, wherein the occlusion device further includes a valve.

Inventive Concept 153. The apparatus according to Inventive Concept 152,
wherein the occlusion device is shaped so as to define a fluid flow path, and
wherein the valve is configured to selectively allow or block fluid flow between the fluid flow path and the balloon chamber when the valve is in open and closed states, respectively.

Inventive Concept 154. The apparatus according to Inventive Concept 151, wherein the occlusion device further includes a distal tip disposed at the distal end portion of the balloon, wherein the spring is connected to the distal tip.

Inventive Concept 155. The apparatus according to Inventive Concept 151, wherein the compliant balloon includes a compliant material selected from the group consisting of: polycaprolactone (PCL), polyglycolic acid (PGA), polylactic acid (PLA), and polydioxanone (PDO or PDS), silicone, polyurethane, polytetrafluoroethylene (PTFE), polymethylmethacrylate, polyether ether ketone (PEEK), polyvinyl chloride, polyethylene terephthalate, nylon, polyamide, polyamide, and polyether block amide (PEBA).

Inventive Concept 156. The apparatus according to any one of Inventive Concepts 151-155,
wherein the occlusion device includes an occlusion-device connector, which is connected to the distal end portion of the balloon and is shaped so as to define an occlusion-device connection interface, and
wherein the stylet includes a stylet connector, which is disposed at a distal end of the stylet and is shaped so as to define a stylet connection interface that is reversibly couplable to the occlusion-device connection interface.

Inventive Concept 157. The apparatus according to Inventive Concept 156, wherein the occlusion-device connection interface and the stylet connection interface are shaped so as to define respective threads.

Inventive Concept 158. The apparatus according to any one of Inventive Concepts 151-155, wherein the occlusion device further includes a proximal LAA-orifice cover, which (a) is fixed to the proximal tube radially surrounding the proximal tube, (b) is configured to assume a radially-compressed state and a radially-expanded state, (c) includes a frame and a covering fixed to the frame, (d) when in the radially-expanded state, is generally orthogonal to the proximal tube and has a greatest dimension, measured perpendicular to the proximal tube, of between 10 and 50 mm, and (e) is indirectly connected to the balloon via the proximal tube and is not directly connected to the balloon.

Inventive Concept 159. The apparatus according to Inventive Concept 158, wherein the occlusion device further includes an orifice-support stent, which (a) is fixed to and extends distally from the proximal LAA-orifice cover, (b) is configured to assume a radially-compressed state and a radially-expanded state, and (c) is generally cylindrical when in the radially-expanded state.

Inventive Concept 160. The apparatus according to Inventive Concept 159, wherein the orifice-support stent, when in the radially-expanded state, has (i) a greatest dimension, measured perpendicular to the proximal tube, of between 8 and 50 mm, and (ii) an axial length of between 4 and 30 mm.

Inventive Concept 161. The apparatus according to any one of Inventive Concepts 151-155, wherein the occlusion device further includes connecting struts fixed to the distal end portion of the balloon and to the proximal end portion of the balloon.

Inventive Concept 162. The apparatus according to Inventive Concept 161, wherein the occlusion device is configured such that inflation of the balloon chamber plastically deforms the connecting struts.

Inventive Concept 163. The apparatus according to Inventive Concept 161, wherein the occlusion device is configured such that shortening of the balloon plastically deforms the connecting struts.

Inventive Concept 164. The apparatus according to any one of Inventive Concepts 151-155, wherein the balloon has an average wall thickness of between 100 and 5000 microns.

Inventive Concept 165. The apparatus according to any one of Inventive Concepts 151-155, wherein the balloon has, at a thinnest portion of a wall of the balloon, a thinnest wall thickness of between 20 and 500 microns.

Inventive Concept 166. The apparatus according to any one of Inventive Concepts 151-155, wherein the delivery system further includes an implant catheter, in which the occlusion device is releasably disposed in a radially-compressed state, in which a greatest distance between the proximal end portion of the balloon and the distal end portion of the balloon is between 8 and 80 mm.

Inventive Concept 167. The apparatus according to Inventive Concept 151, wherein the occlusion device further includes a proximal connector that is configured to releasably connect the occlusion device to a correspondingly configured distal connector of the delivery system.

Inventive Concept 168. The apparatus according to Inventive Concept 167, wherein the proximal connector is shaped so as to define a thread.

Inventive Concept 169. The apparatus according to any one of Inventive Concepts 167-168, for use with a guidewire, wherein the delivery system further includes an implant catheter connected to an operating handle, the implant catheter including a longitudinal passageway for the guidewire, a distal connector for releasably connecting the implant catheter to the correspondingly configured proximal connector of the occlusion device, and an inflation tube channel releasably connectable to the fluid flow path of the occlusion device.

There is also provided, in accordance with an Inventive Concept 170 of the present invention, a method for occluding a left atrial appendage (LAA) of a patient, the method including:

using a delivery system, positioning a compliant balloon of an occlusion device in a longitudinally extended form thereof in the LAA;

inflating the compliant balloon by filling a fluid into a fluid-tight balloon chamber defined by the balloon, via a fluid flow path having one or more fluid-flow-path openings to the balloon chamber, while a valve-opening prop of the delivery system is in a propping position in which the valve-opening prop props open and deforms an elastomer sleeve of a valve of the occlusion device, such that the elastomer sleeve does not seal the one or more fluid-flow-path openings and the valve is in an open state, wherein the elastomer sleeve surrounds a portion of an actuating shaft of the occlusion device, the actuating shaft (a) disposed at least partially within the balloon chamber, (b) connected to a distal end portion of the balloon, and (c) longitudinally moveable with respect to a proximal end portion of the balloon so as to set a distance between the distal and the proximal end portions of the balloon;

transitioning the valve-opening prop to a non-propping position, in which the valve-opening prop does not prop open the elastomer sleeve, such that elastomer sleeve assumes a resting state in which the sleeve covers and seals the one or more fluid-flow-path openings, such that the valve is in a closed state; and releasing the occlusion device from the delivery system.

There is further provided, in accordance with an Inventive Concept 171 of the present invention, a method for occluding a left atrial appendage (LAA) of a patient, the method including:

using a delivery system, positioning a compliant balloon of an occlusion device in a longitudinally extended form thereof in the LAA;

inflating the compliant balloon by filling a fluid into a fluid-tight balloon chamber defined by the balloon, via a fluid flow path having one or more fluid-flow-path openings to the balloon chamber, while one or more guidewires of the delivery system are in a propping position, in which the one or more guidewires prop open and deform an elastomer sleeve of a valve of the occlusion device such that the elastomer sleeve does not seal the one or more fluid-flow-path openings and the valve is in an open state, wherein the elastomer sleeve surrounds a portion of an actuating shaft that is (a) disposed at least partially within the balloon chamber, (b) connected to a distal end portion of the balloon, and (c) longitudinally moveable with respect to a proximal end portion of the balloon so as to set a distance between the distal and the proximal end portions of the balloon;

transitioning the one or more guidewires to a non-propping position, in which the one or more guidewires do not prop open the elastomer sleeve, such that elastomer sleeve assumes a resting state in which the sleeve covers and seals the one or more fluid-flow-path openings, such that the valve is in a closed state; and releasing the occlusion device from the delivery system.

The present invention will be more fully understood from the following detailed description of embodiments thereof, taken together with the drawings, in which:

BRIEF DESCRIPTION OF THE DRAWINGS

FIGS. 3A-F are schematic illustrations of steps of a method of deploying the occlusion device of FIG. 1 using the delivery system of FIG. 2, in accordance with an application of the present invention;

FIGS. 9A-B are schematic cross-sectional illustrations of the occlusion device of FIG. 8 and a distal portion of a delivery system, in accordance with an application of the present invention;

FIG. 10 is a schematic illustration of still another occlusion device for occluding an LAA, in accordance with an application of the present invention;

FIG. 11 is a schematic cross-sectional illustration of the occlusion device of FIG. 10 and a distal portion of a delivery system, in accordance with an application of the present invention;

DETAILED DESCRIPTION OF APPLICATIONS

Figure 1:
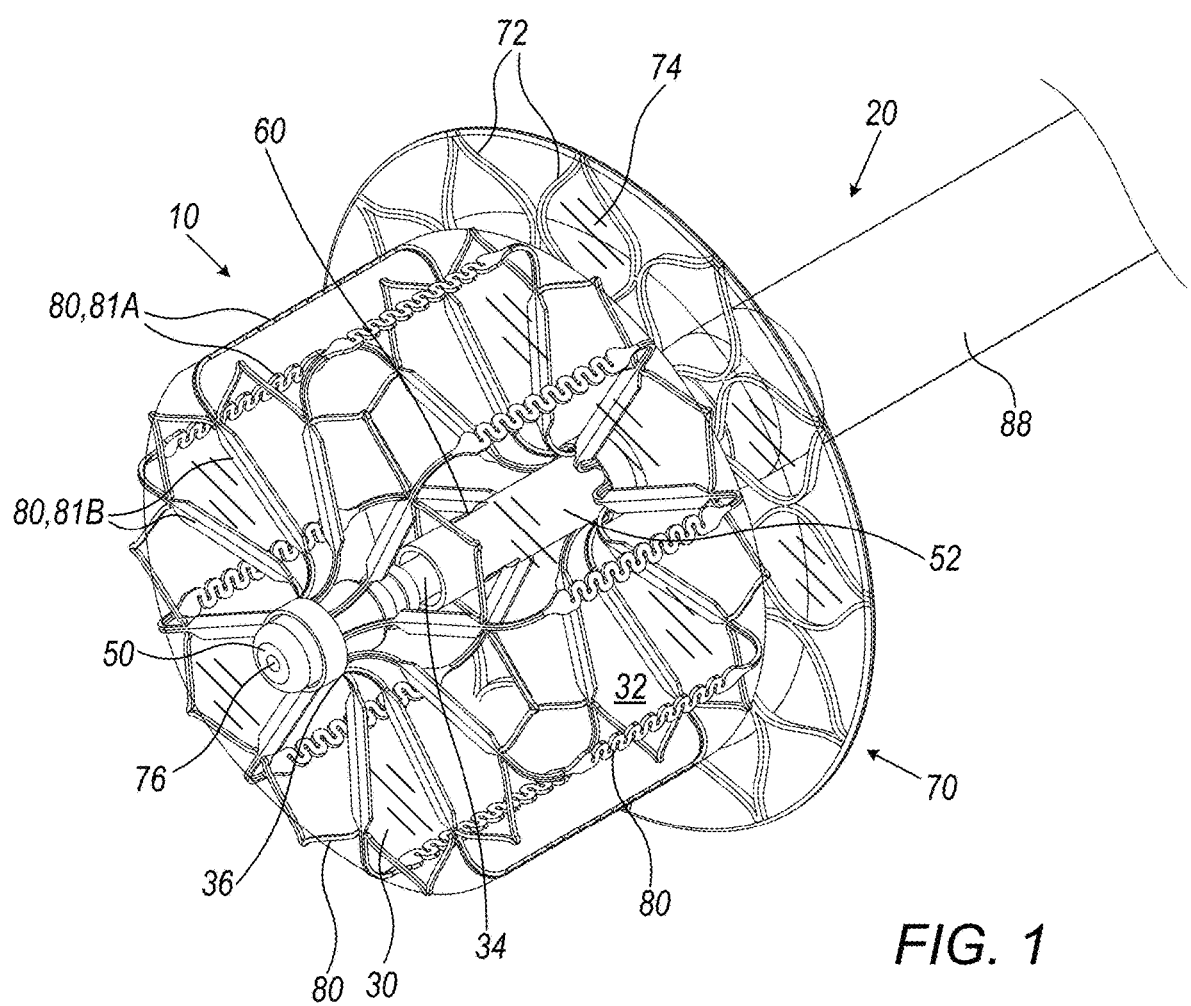
FIG. 1 is a schematic illustration of an occlusion device for occluding a left atrial appendage (LAA), in accordance with an application of the present invention.

FIG. 1 is a schematic illustration of an occlusion device 10 for occluding a left atrial appendage (LAA), in accordance with an application of the present invention. Occlusion device 10 is for use with a delivery system 20, which is described in more detail hereinbelow with reference to FIGS. 3A-F. Delivery system 20 and the other delivery systems described herein are typically transcatheter delivery systems that enable percutaneous deployment of the occlusion devices.

Figure 2A:
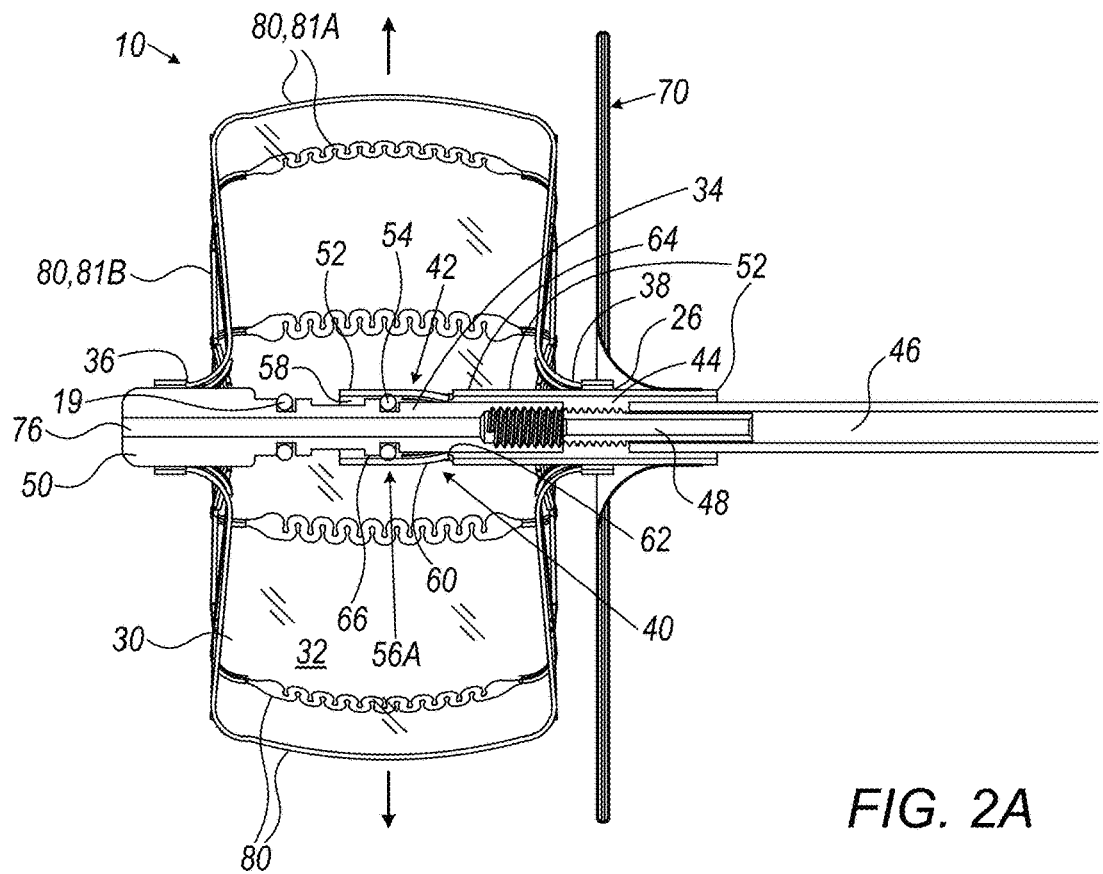
FIGS. 2A-B are schematic cross-sectional illustrations of the occlusion device of FIG. 1 and a distal portion of a delivery system, in accordance with an application of the present invention.
Figure 2B:
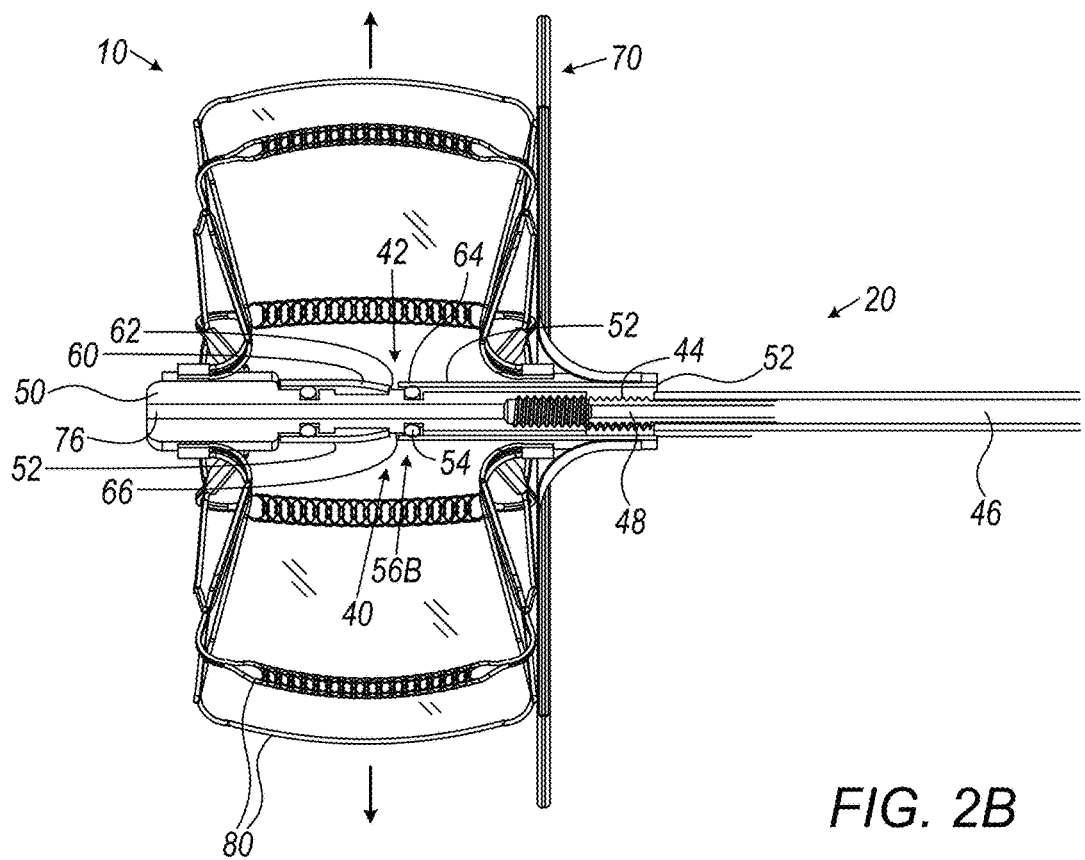

Reference is also made to FIGS. 2A-B, which are schematic cross-sectional illustrations of occlusion device 10 and a distal portion of delivery system 20, in accordance with an application of the present invention. FIG. 2A shows occlusion device 10 with a locking mechanism 40 thereof in an unlocked state and valve 42 thereof in an open state, as described hereinbelow. FIG. 2B shows occlusion device 10 with locking mechanism 40 in a locked state and valve 42 in a closed state, as described hereinbelow.

For some applications, occlusion device 10 comprises:
- a compliant balloon 30 defining a fluid-tight balloon chamber 32;
- an actuating shaft 34, which is (a) disposed at least partially within balloon chamber 32, (b) connected to a distal end portion 36 of balloon 30, and (c) longitudinally moveable with respect to a proximal end portion 38 of balloon 30 so as to set a distance between distal and proximal end portions 36 and 38 of balloon 30;
- locking mechanism 40, which is configured to assume locked and unlocked states, as shown in FIG. 2B and 2A, respectively; and
- a valve 42.

Occlusion device 10 is configured such that proximally longitudinally moving actuating shaft 34 expands balloon 30 in a radial or a lateral direction by shortening the distance between distal and proximal end portions 36 and 38 of balloon 30 to a desired distance.

Locking mechanism 40 is configured, when in the locked state, to maintain, between distal end portion 36 of balloon 30 and proximal end portion 38 of balloon 30, the distance set using actuating shaft 34.

For some applications, occlusion device 10 is shaped so as to define a fluid flow path 44 along (e.g., alongside, as shown) a portion of actuating shaft 34. Valve 42 is configured to selectively:
- allow fluid flow between fluid flow path 44 and balloon chamber 32 when valve 42 is in the open state, as shown in FIG. 2A, or
- block fluid flow between fluid flow path 44 and balloon chamber 32 when valve 42 is in the closed state, as shown in FIG. 2B.

For some applications, occlusion device 10 is configured such that reduction of the distance, by proximal longitudinal movement of actuating shaft 34:
- to a first predetermined distance between distal and proximal end portions 36 and 38 of balloon 30 automatically transitions valve 42 from the open state to the closed state, as shown in the transition from FIG. 2A to FIG. 2B, and
- to a second predetermined distance between distal and proximal end portions 36 and 38 of balloon 30 automatically transitions locking mechanism 40 from the unlocked state to the locked state, as also shown in the transition from FIG. 2A to FIG. 2B.

For some applications, the first predetermined distance does not equal the second predetermined distance. For example, the first predetermined distance may be less than the second predetermined distance, such that the proximal longitudinal movement of actuating shaft 34 first automatically transitions valve 42 from the open state to the closed state and subsequently automatically transitions locking mechanism 40 from the unlocked state to the locked state. Alternatively, the first predetermined distance may be greater than the second predetermined distance, such that this sequence is reversed.

Further alternatively, for some applications, the first predetermined distance equals the second predetermined distance, such that the proximal longitudinal movement of actuating shaft 34 simultaneously automatically transitions valve 42 from the open state to the closed state and automatically transitions locking mechanism 40 from the unlocked state to the locked state.

For some applications, in order to cause the above-mentioned proximal longitudinal movement of actuating shaft 34, delivery system 20 comprises a pull shaft 46, which is releasably coupled a proximal end portion of actuating shaft 34. For example, a distal portion of pull shaft 46 may comprise a pull-shaft coupling 48, which may for example, be shaped so as to define a thread that removably engages a corresponding thread defined by the proximal end portion of actuating shaft 34. Rotation of pull shaft 46 disengages shaft coupling 48 from the corresponding thread defined by the proximal end portion of actuating shaft 34.

Typically, occlusion device 10 is configured to be releasably connected to delivery system 20. For some applications, occlusion device 10 is configured such that fluid flow path 44 is coupled in fluid communication with delivery system 20 when occlusion device 10 is releasably connected to delivery system 20, such as shown in FIGS. 2A-B.

For some applications, actuating shaft 34 is shaped so as to define, at least in part, a distal tip 50 disposed at distal end portion 36 of balloon 30, as shown in FIGS. 1 and 2A-B.

For some other applications, occlusion device 10 further comprises a distal tip disposed at distal end portion 36 of balloon 30, and actuating shaft 34 is connected to the distal tip (configuration not shown).

Alternatively or additionally, for some applications, occlusion device 10 further comprises a proximal base disposed at proximal end portion 38 of balloon 30, and actuating shaft 34 is moveable (e.g., longitudinally or rotationally) with respect to the proximal base (configuration not shown).

For some applications, valve 42 is disposed along actuating shaft 34, such as shown in FIGS. 2A-B.

For some applications, occlusion device 10 further comprises a proximal tube 52, which is axially fixed with respect to proximal end portion 38 of balloon 30. Actuating shaft 34 is slidably disposed partially within proximal tube 52, e.g., so as to indirectly connect actuating shaft 34 to proximal end portion 38 via proximal tube 52. For some of these applications, occlusion device 10 is shaped so as to define fluid flow path 44 along the portion of actuating shaft 34, radially between an external surface of actuating shaft 34 and an internal surface of proximal tube 52, such as shown in FIGS. 2A-B. Optionally, valve 42 is disposed along actuating shaft 34.

For some applications, valve 42 comprises a seal 54 around at least a portion of (e.g., entirely around) the external surface of actuating shaft 34. Valve 42 is configured to assume (a) the open state when seal 54 is disposed at one or more first axial positions 56A with respect to proximal tube 52 (one such first axial position is shown in FIG. 2A), and (b) the closed state when seal 54 is disposed at one or more second axial positions 56B with respect to proximal tube 52 (one such second axial position is shown in FIG. 2B). The one or more second axial positions 56B are proximal to the one or more first axial positions 56A. For example, seal 54 may comprise an O-ring, as shown in FIGS. 2A-B, e.g., a single O-ring or a series of O-rings. Optionally, one or more additional seals 19, e.g., one or more O-rings, are provided to provide further stabilization an alignment of the distal tube inside the proximal tube by friction.

For some applications, seal 54, actuating shaft 34, and proximal tube 52 are arranged such that seal 54 blocks fluid flow out of a distal end 58 of proximal tube 52, at least when seal 54 is disposed at the one or more first axial positions 56A with respect to proximal tube 52, such as shown in FIG. 2A. Alternatively or additionally, friction between seal 54 and the inner surface of proximal tube 52 increases structural stability, and/or enables stepwise inflation/implantation.

For some applications, a wall of proximal tube 52 is shaped so as to define one or more tabs 60 through the wall. The one or more tabs 60 are biased to flex radially inward. When valve 42 is in the open state, as shown in FIG. 2A, fluid flow path 44 passes through the wall between respective proximal ends 62 of the one or more tabs 60 and a non-tabbed portion 64 of the wall axially adjacent the one or more tabs 60, such as proximal to the one or more tabs 60, as shown.

For some applications, the external surface of actuating shaft 34 is shaped so as to define one or more protrusions 66 around at least a portion of (e.g., entirely around) actuating shaft 34. Proximal ends 62 of the one or more tabs 60 are shaped so as to prevent distal movement of the one or more protrusions 66 when the one or more protrusions 66 are disposed proximal to the proximal ends 62 of the one or more tabs 60, such as shown in FIG. 2B, thereby causing locking mechanism 40 to assume the locked state.

For some applications, occlusion device 10 further comprises a proximal LAA-orifice cover 70, which:
 is fixed to proximal tube 52 radially surrounding proximal tube 52,
 is configured to assume a radially-compressed state, such as shown in FIG. 3A, described hereinbelow, and a radially-expanded state, such as shown in FIGS. 1 and 2A-B,
 comprises frame 72 and a covering 74 fixed to frame 72, when in the radially-expanded state, is generally orthogonal to proximal tube 52 and has a greatest dimension, measured perpendicular to proximal tube 52, of at least 10 mm (e.g., at least 20 mm), no more than 50 mm (e.g., no more than 30 mm), and/or between 10 and 50 mm (e.g., between 20 and 30 mm), and
 is typically indirectly connected to balloon 30 via proximal tube 52 and is not directly connected to balloon 30.

This indirect connection of proximal LAA-orifice cover 70 to balloon 30 generally prevents an anodic reaction between the typically super-elastic (e.g., Nitinol) material of frame 72 of proximal LAA-orifice cover 70 and the typically plastically deformable (e.g., stainless steel) material of struts 80, described hereinbelow. Such a reaction might have occurred if the two elements were instead welded or otherwise bonded together in contact with each other. (Connection of the elements via an independent and passive element, such as an internal tube or shaft, also does not cause such a reaction.) Alternatively, proximal LAA-orifice cover 70 is directly connected to balloon 30, such as if frame 72 comprises a different plastically-deformable material, such as titanium.

For some applications, occlusion device 10 further comprises orifice-support stent 290, described hereinbelow with reference to FIGS. 8 and 9A-B.

For some applications, actuating shaft 34 is shaped so as to define a guidewire lumen 76 for slidingly receiving therein a guidewire and/or passage of liquid injected under pressure, such as contrast media injected from the proximal handle of the delivery tool to the distal end of the occlusion device. Alternatively, for other applications, actuating shaft 34 is not shaped so as to define a guidewire lumen.

For some applications, compliant balloon 30 comprises a compliant material selected from the group consisting of: polycaprolactone (PCL), polyglycolic acid (PGA), polylactic acid (PLA), and polydioxanone (PDO or PDS), silicone, polyurethane, polytetrafluoroethylene (PTFE), polymethylmethacrylate, polyether ether ketone (PEEK), polyvinyl chloride, polyethylene terephthalate, nylon, polyamide, polyamide, and polyether block amide (PEBA).

For some applications, balloon 30 has an average wall thickness of between 100 and 5000 microns. Alternatively or additionally, for some applications, balloon 30 has, at a thinnest portion of a wall of balloon 30, a thinnest wall thickness of between 20 and 500 microns.

For some applications, occlusion device 10 further comprises connecting struts 80 fixed to distal end portion 36 of balloon 30 and to proximal end portion 38 of balloon 30. Struts 80 may be disposed inside balloon 30, outside balloon 30, or some inside and some outside balloon 30. For some applications, struts 80 are arranged as a frame. For some applications, struts 80 are arranged in a cage-like arrangement. Typically, struts 80 comprise a plastically-deformable material, such as stainless steel or titanium. Typically, struts 80 help shape balloon 30 as the balloon chamber is inflated and/or the balloon is shortened.

Typically, occlusion device 10 is configured such that inflation of balloon chamber 32 plastically deforms connecting struts 80. For some applications, occlusion device 10 is configured such that shortening of balloon 30 plastically deforms connecting struts 80.

For some applications, struts 80 are configured such that inflation of balloon chamber 32 primarily causes radial deformation of struts 80, rather than deformation of the struts in a distal or proximal direction. To this end, first lateral portions 81A of struts 80 arranged along a lateral surface of balloon 30 may be more compliant than second end portions 81B of struts 80 arranged on a distal surface of balloon 30 and/or on a proximal surface of balloon 30. For example, first lateral portions 81A may be thinner than second end portions 81B, as shown in FIG. 1, and/or first lateral portions 81A may be shaped to be more compliant, e.g., have a serpentine (e.g., sinusoidal) shape, as shown. Typically, first lateral portions 81A are oriented parallel to a central longitudinal axis of occlusion device 10.

Reference is now made to FIGS. 3A-F, which are schematic illustrations of steps of a method of deploying occlusion device 10 using delivery system 20, in accordance with an application of the present invention.

Figure 3C:
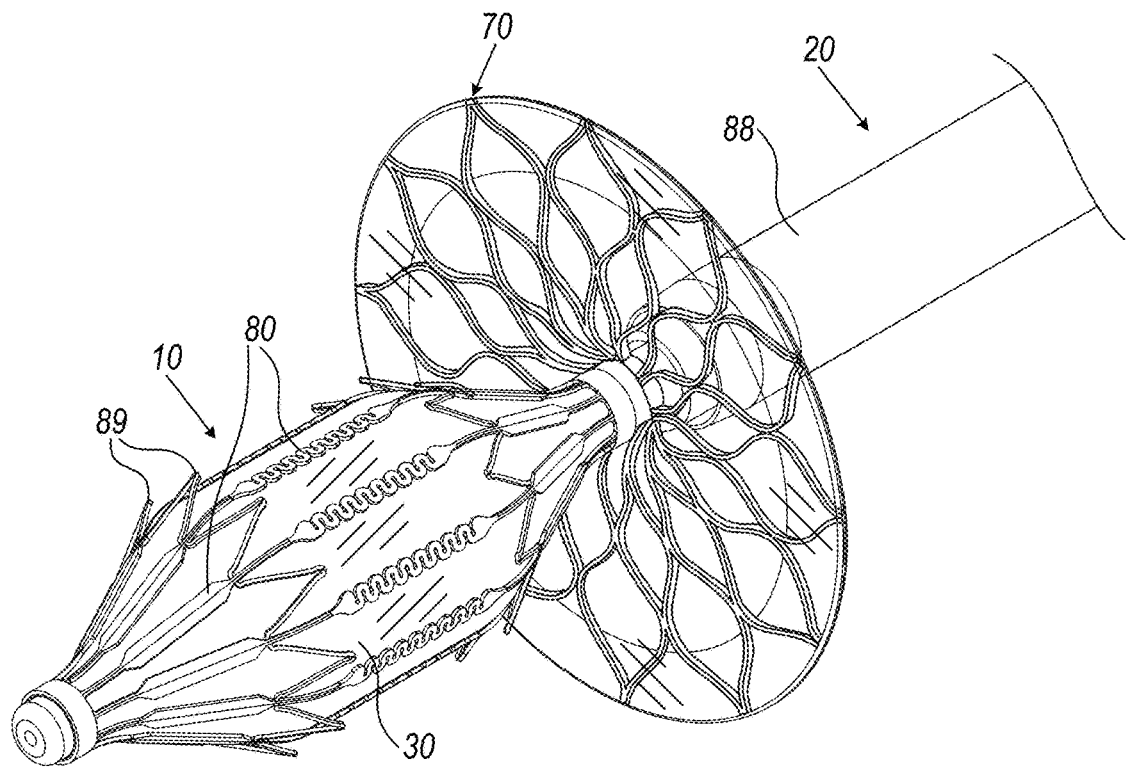
Figure 3D:
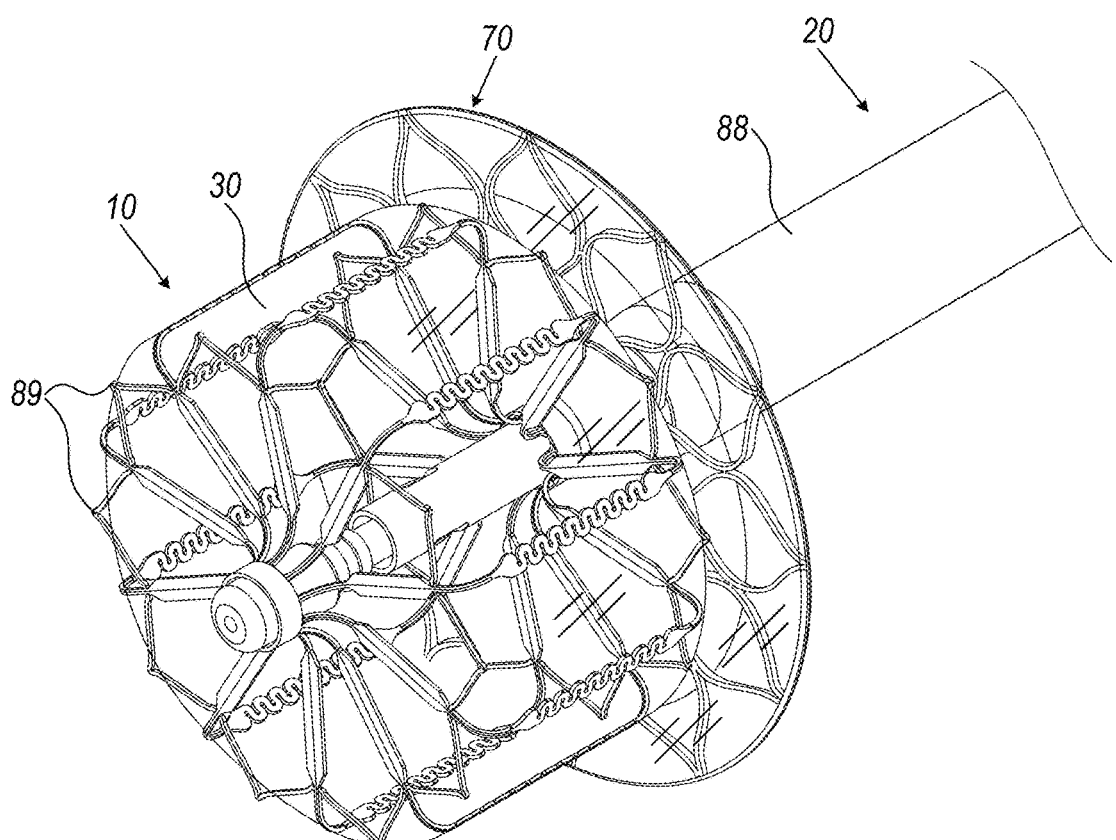
Figure 3E:
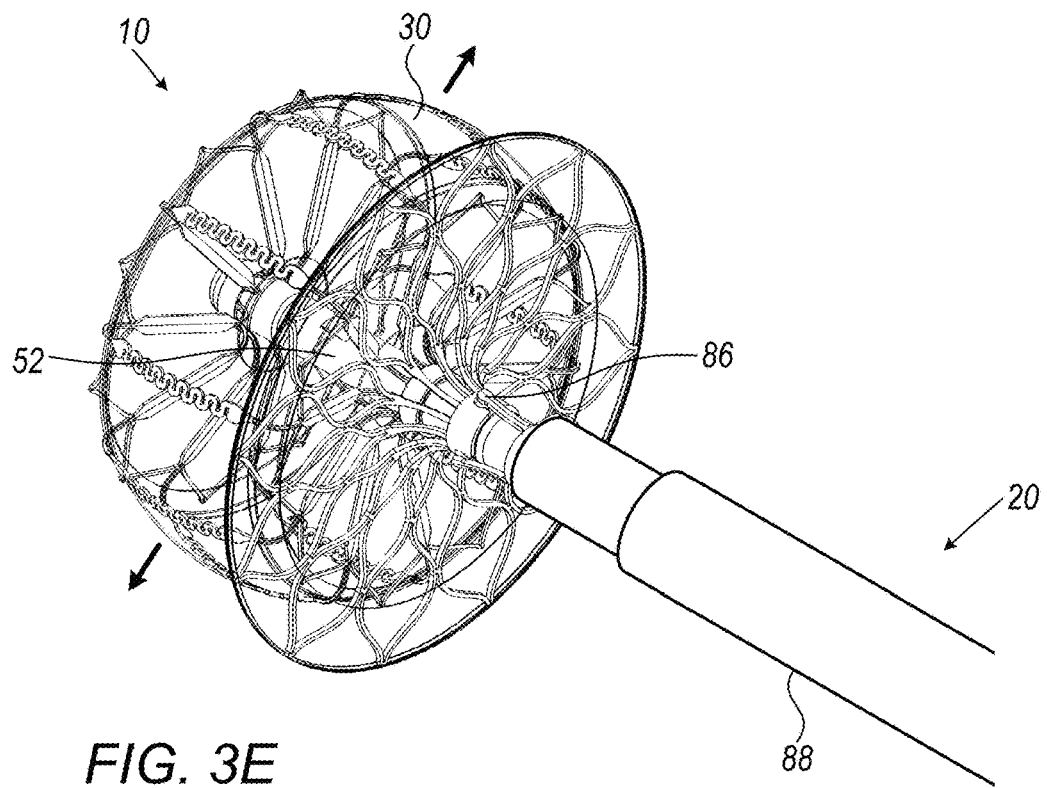
Figure 3F:
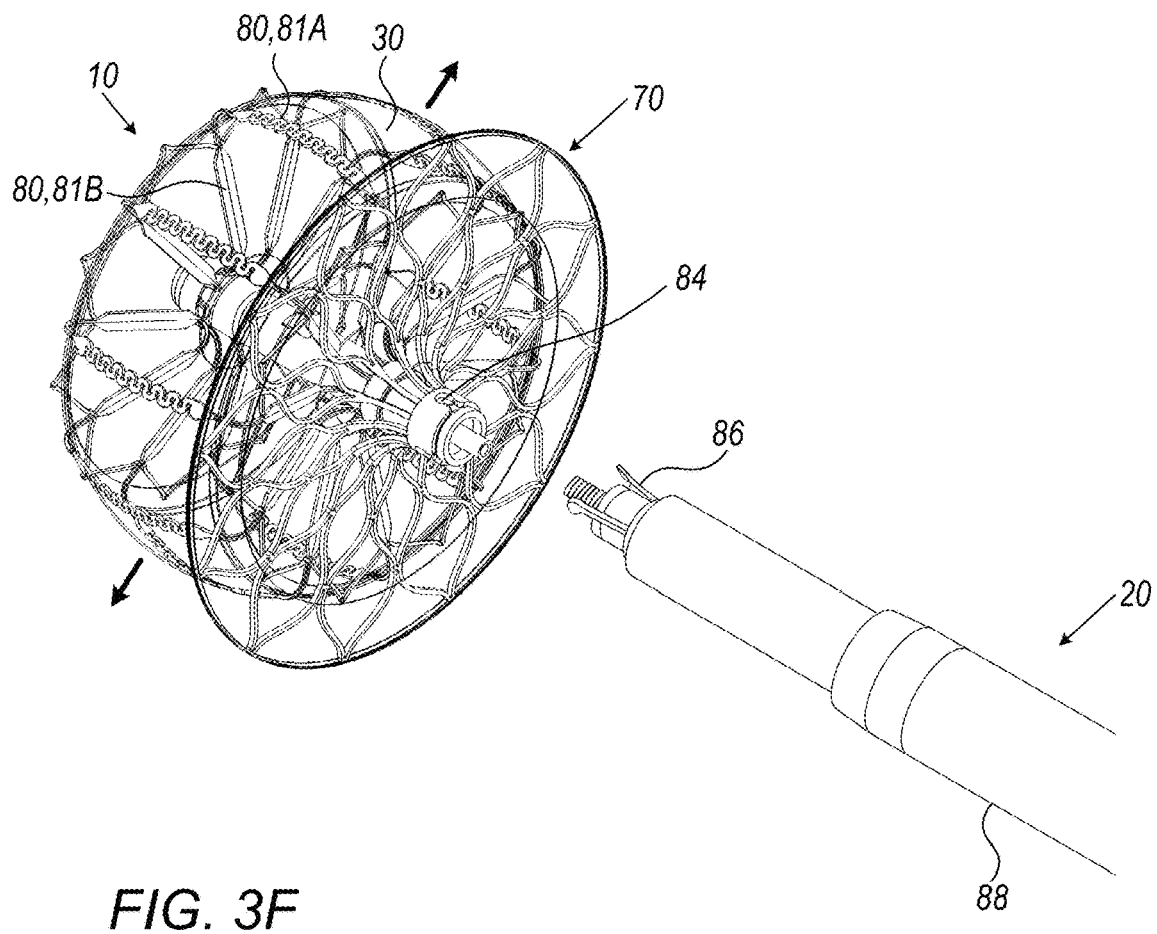
Figure 4A:
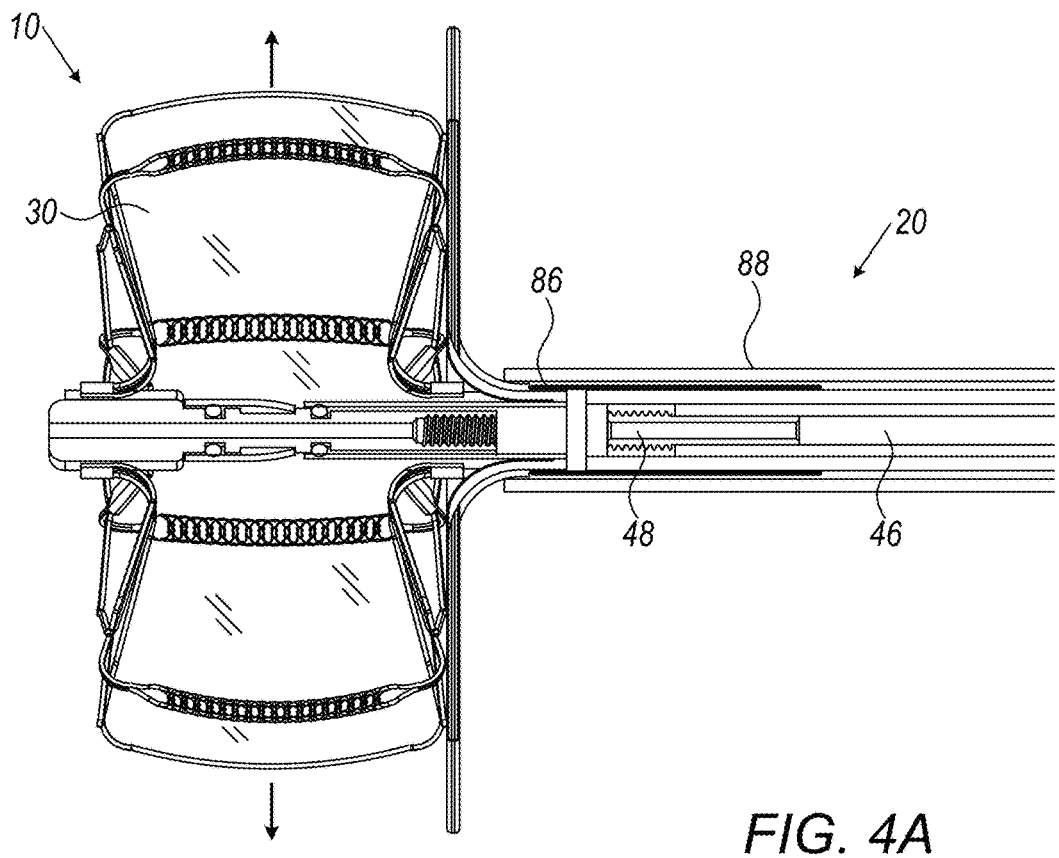
FIGS. 4A-C are schematic cross-sectional views of a portion of the steps of the method shown in FIGS. 3A-F, in accordance with an application of the present invention.
Figure 4B:
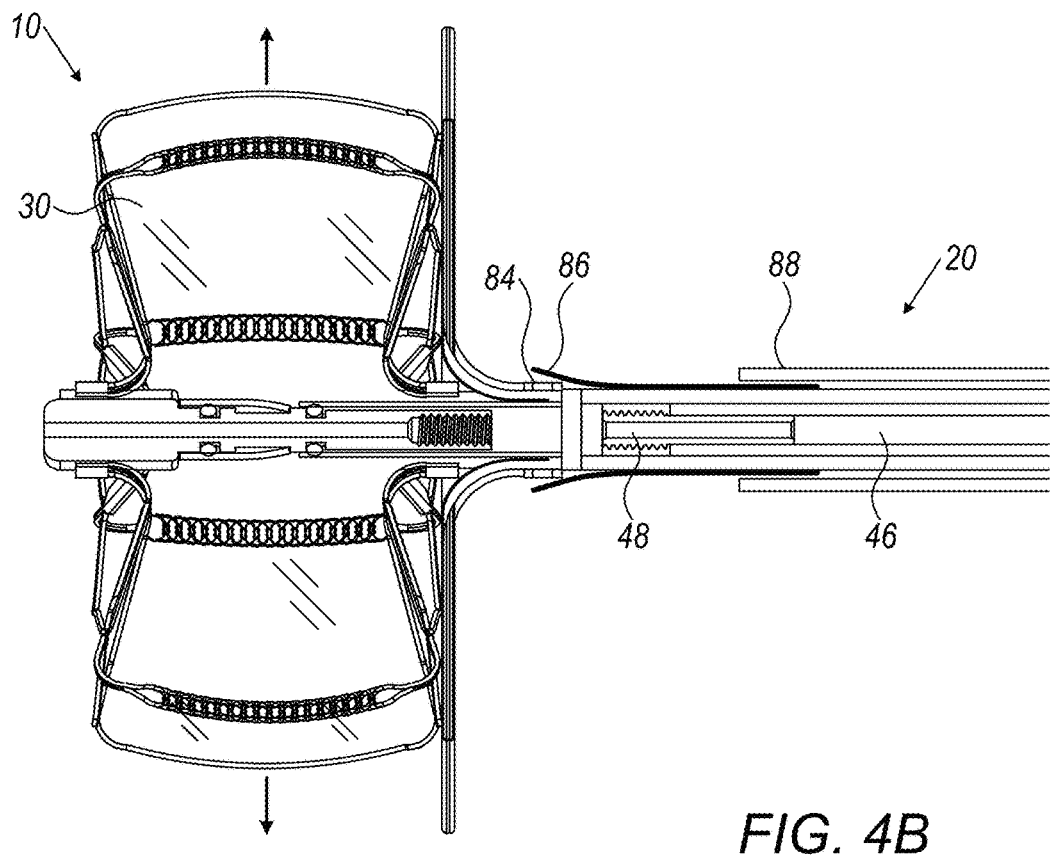
Figure 4C:
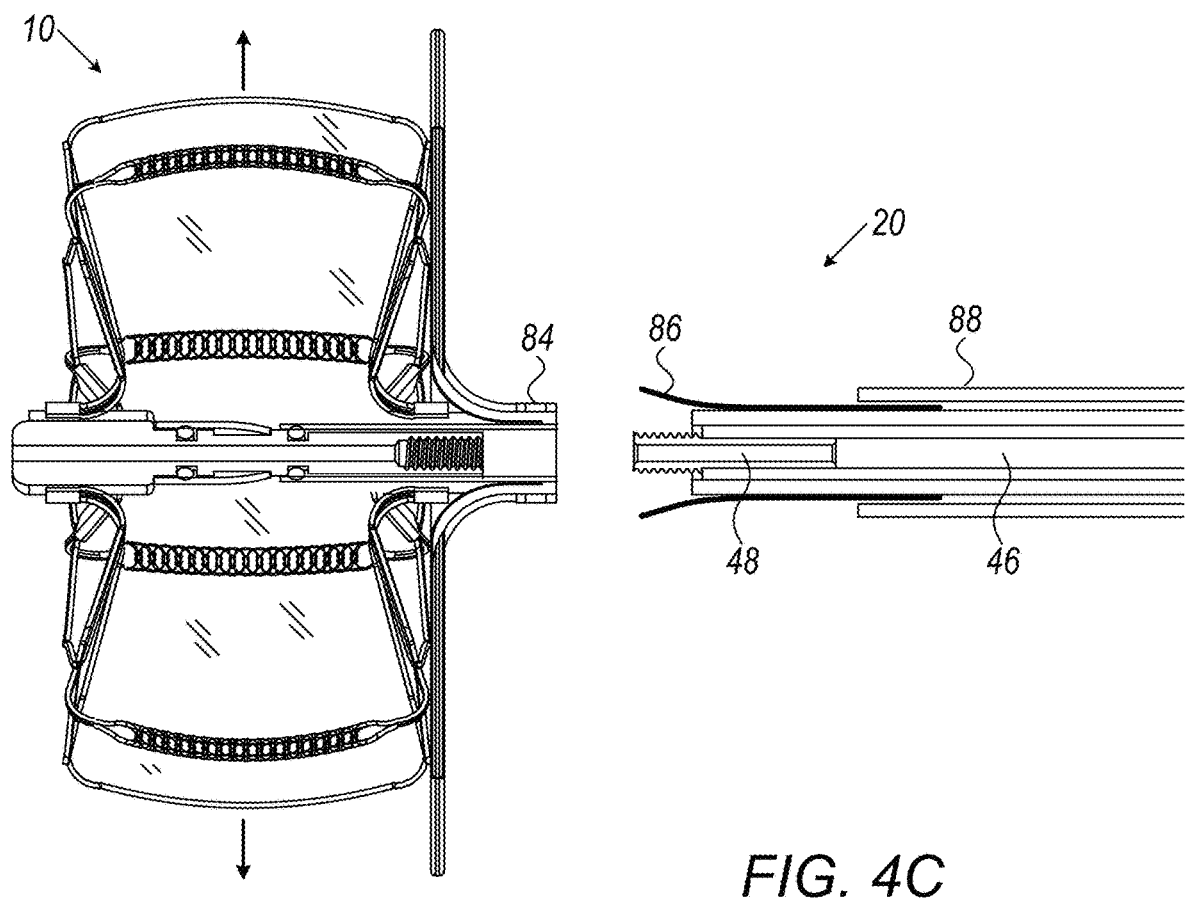

Reference is also made to FIGS. 4A-C, which are schematic cross-sectional views of a portion of the steps of the method shown in FIGS. 3A-F, in accordance with an application of the present invention.

FIG. 3A schematically shows occlusion device 10 releasably disposed in a radially-compressed state within a sheath 82 of delivery system 20. Typically, a greatest distance between proximal end portion 38 of balloon 30 and distal end portion 36 of balloon 30 is at least 8 mm (e.g., at least 15 mm), no more than 80 mm (e.g. no more than 60 mm), and/or between 8 and 80 mm (e.g., between 15 and 60 mm), when occlusion device 10 is in this radially-compressed state.

For some applications, occlusion device 10 comprises a proximal connector 84 that is configured to releasably connect occlusion device 10 to a correspondingly configured distal connector 86 of delivery system 20.

For some applications, distal connector 86 comprises one or more legs that engage one or more respective coupling sites (e.g., slots) of proximal connector 84, such as perhaps best seen in FIGS. 4A-C. For example, the legs may be configured to biased radially outward when in an unconstrained, resting state, and may be held radially inward engaging the coupling sites of proximal connector 84, such as by implant catheter 88, as shown in FIG. 4A. Proximal withdrawal of implant catheter 88 with respect to occlusion device 10 release the legs, as shown in FIG. 4B.

Alternatively, proximal connector 84 is shaped so as to define a thread (configuration not shown).

For some applications, delivery system 20 comprises an implant catheter 88 that is connected to an operating handle (not shown). Implant catheter 88 comprises (a) a longitudinal passageway for a guidewire, (b) distal connector 86 for releasably connecting implant catheter 88 to correspondingly configured proximal connector 84 of occlusion device 10, and (c) an inflation tube channel releasably connectable to fluid flow path 44 of occlusion device 10. The longitudinal passageway may alternatively or additionally be used to inject contrast media from the handle to a distal opening of the inflation tube channel distally to the balloon.

FIG. 3B shows occlusion device 10 after sheath 82 has been proximally withdrawn, thereby releasing occlusion device 10. FIG. 3B also shows proximal LAA-orifice cover 70 in its radially-expanded state. Typically, frame 72 of proximal LAA-orifice cover 70 comprises a shape-memory memory, e.g., a super-elastic metal, which causes cover 70 to automatically transition to the radially-expanded state upon release from sheath 82. Balloon 30 remains in a non-inflated, elongate configuration at this stage of deployment.

Typically, a healthcare worker places the distal end of occlusion device 10 into the LAA, using delivery system navigation.

As shown in FIGS. 3C-D, the healthcare worker inflates balloon chamber 32. FIG. 3C shows occlusion device 10 upon partial inflation of balloon chamber 32, while FIG. 3D shows occlusion device 10 upon complete inflation of balloon chamber 32. Balloon 30 may be inflated by filling balloon chamber 32 with any fluid, including but not limited to saline solution (optionally comprising a contrast medium), blood (e.g., autologous blood), foam, and/or a glue (e.g., a gel, a liquid polymer that can change its proprieties to become rigid, or a hydrogel that remains a gel or self-cures at body temperature).

For some applications, struts 80 are shaped so as to define a plurality of spikes 89 that are initially generally axially oriented, as shown in FIG. 3C, and are configured to extend more radially upon expansion of balloon 30 to serve as tissue-engaging barbs, as shown in FIG. 3D.

FIGS. 3E and 4A show occlusion device 10 after (a) valve 42 has transitioned from the open state to the closed state, (b) actuating shaft 34 has been proximally longitudinally moved to expand balloon 30 in a radial or a lateral direction by shortening the distance between distal and proximal end portions 36 and 38 of balloon 30 to a desired distance, and (c) locking mechanism 40 has transitioned from the unlocked state to the locked state, as described hereinabove with reference to FIGS. 2A-B. Typically, after balloon 30 has been finally filled, actuating shaft 34 is proximally longitudinally moved to expand balloon 30 in a radial or a lateral direction by shortening the distance between distal and proximal end portions 36 and 38 of balloon 30 to a desired distance. Proximal connector 84 of occlusion device 10 is still releasably connected to correspondingly configured distal connector 86 of delivery system 20.

FIGS. 3F and 4B-C show occlusion device 10 after proximal connector 84 of occlusion device 10 has been released from distal connector 86 of delivery system 20.

FIG. 4C also shows occlusion device 10 after pull shaft 46 has been decoupled from the proximal end portion of actuating shaft 34, such as by rotating pull shaft 46 to unscrew it, as described hereinabove.

Figure 5:
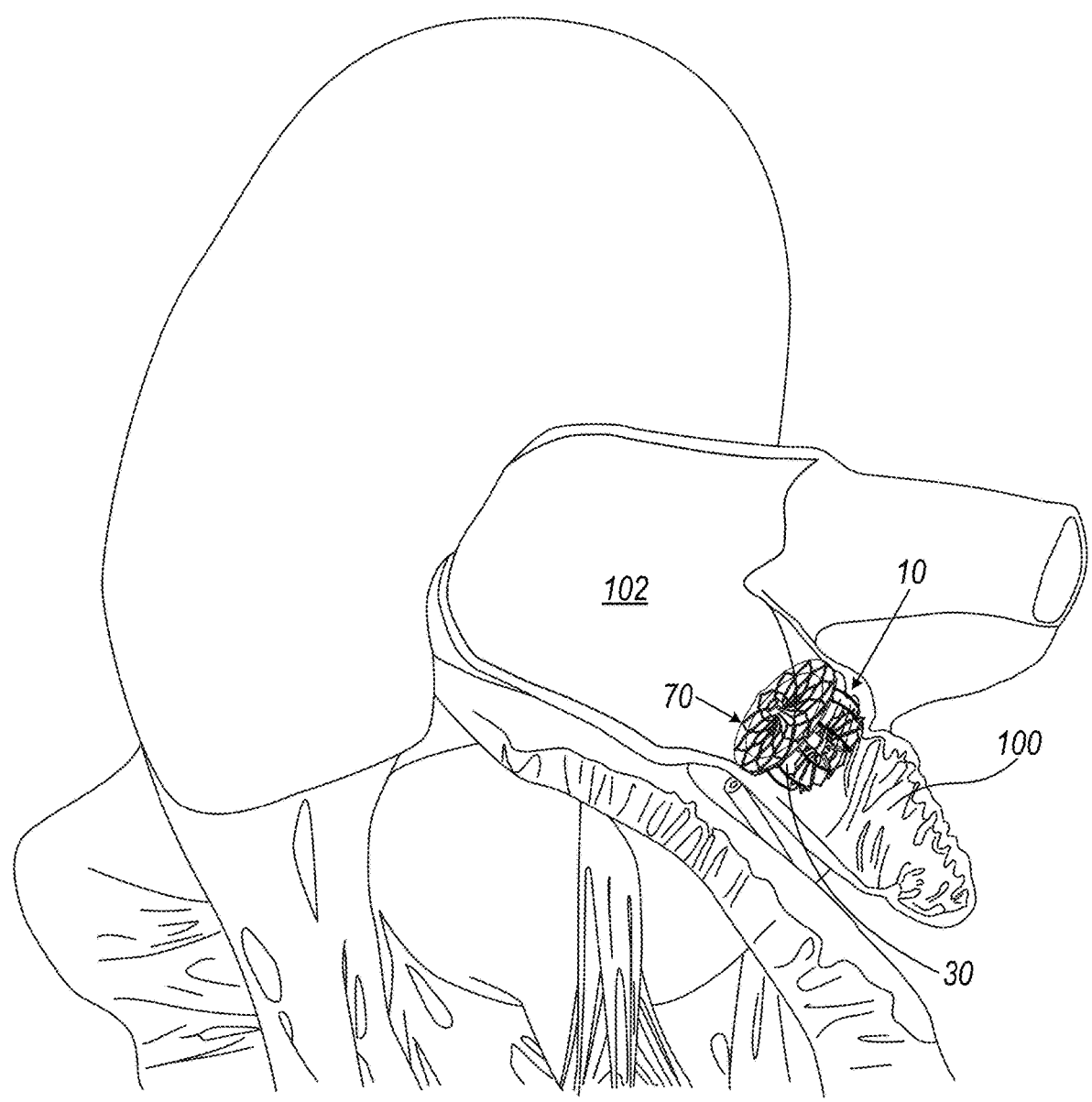
FIG. 5 is a schematic illustration of the occlusion device of FIG. 1 implanted to occlude an LAA, in accordance with an application of the present invention.

Reference is now made to FIG. 5, which is a schematic illustration of occlusion device 10 implanted to occlude an LAA 100, in accordance with an application of the present invention. As can be seen, balloon 30 is disposed within LAA 100, and proximal LAA-orifice cover 70 is disposed in a left atrium 102 outside LAA 100, against the atrial wall surrounding the orifice of LAA 100, thereby creating a continuum with the atrium at the LAA level. Typically, proximal LAA-orifice cover 70 protrudes only minimally because of its relatively flat shape, so as not to interfere with blood flow and not to cause thrombosis. Typically, struts 80 provide most of the anchoring of occlusion device 10, and balloon 30 provides most of the sealing of the LAA. In addition, in configurations in which covering 74 of proximal LAA-orifice cover 70 is blood-impermeable, proximal LAA-orifice cover 70 provides additional sealing of the LAA, primarily to inhibit creation of thrombi on the balloon surface at the orifice level.

For some applications, proximal LAA-orifice cover 70 is asymmetric about proximal tube 52, e.g., elliptical or with a radius greater in one direction than in the perpendicular direction.

For some applications, proximal LAA-orifice cover 70 is configured to have an adjustable greatest dimension measured perpendicular to proximal tube 52. For example, rotation of a proximal LAA-orifice cover 70 adjustment mechanism may adjust the greatest dimension.

For some applications, covering 74 of proximal LAA-orifice cover 70 is blood-permeable, so as to serve as filter for the passage of blood in and out of the LAA. For other applications, covering 74 is not blood-permeable, so as to create a secondary sealing of the LAA in addition to the sealing provided by balloon 30.

For some applications, proximal LAA-orifice cover 70 is bioresorbable and/or drug-eluting.

Figure 6:
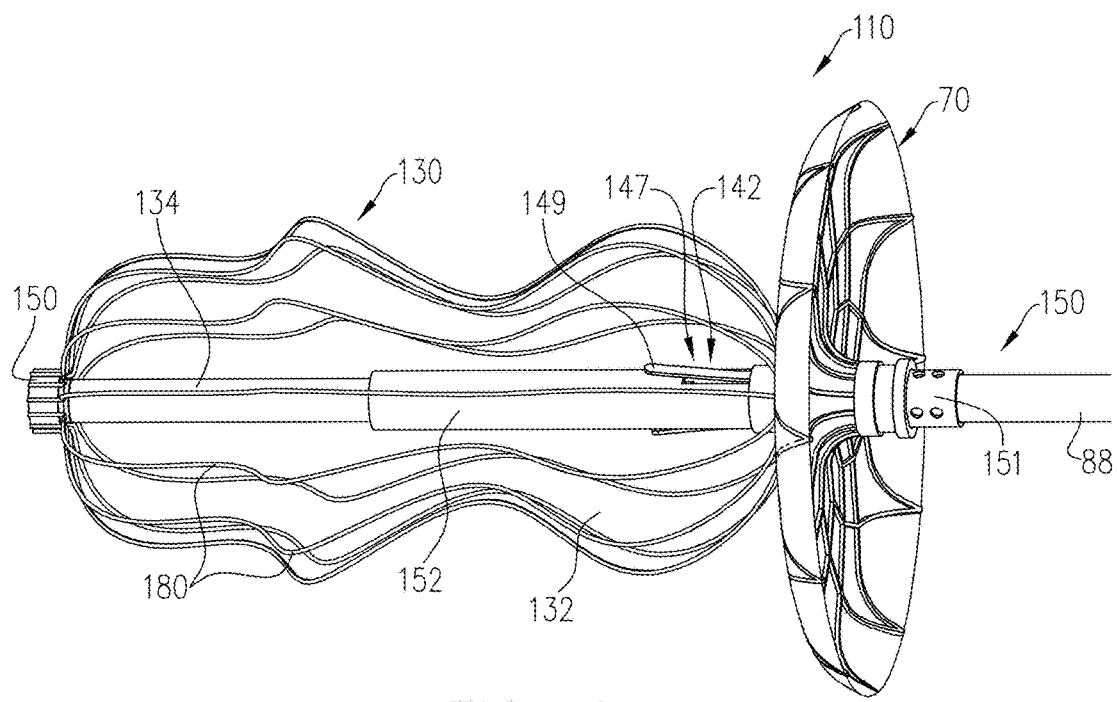
FIG. 6 is a schematic illustration of another occlusion device for occluding an LAA, in accordance with an application of the present invention.

Reference is now made to FIG. 6, which is a schematic illustration of an occlusion device 110 for occluding an LAA, in accordance with an application of the present invention. Occlusion device 110 is for use with a delivery system 120. Other than as described hereinbelow, occlusion device 110 is similar to occlusion device 10, described hereinabove with reference to FIGS. 1-5, and may implement any of the features thereof, mutatis mutandis. Similarly, other than as described hereinbelow, delivery system 120 is similar to delivery system 20, described hereinabove with reference to FIGS. 1-5, and may implement any of the features thereof, mutatis mutandis. Like reference numerals refer to like parts.

Figure 7A:
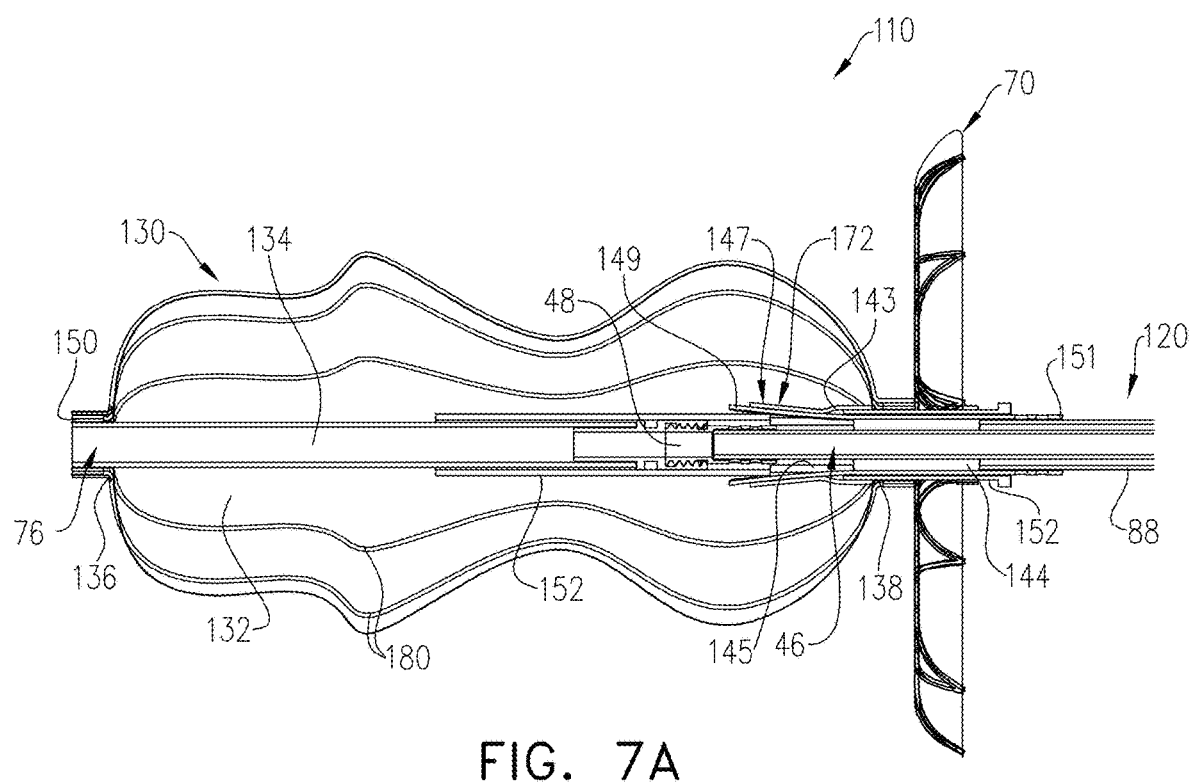
FIGS. 7A-C are schematic cross-sectional illustrations of the occlusion device of FIG. 6 and a distal portion of a delivery system, in accordance with an application of the present invention.
Figure 7B:
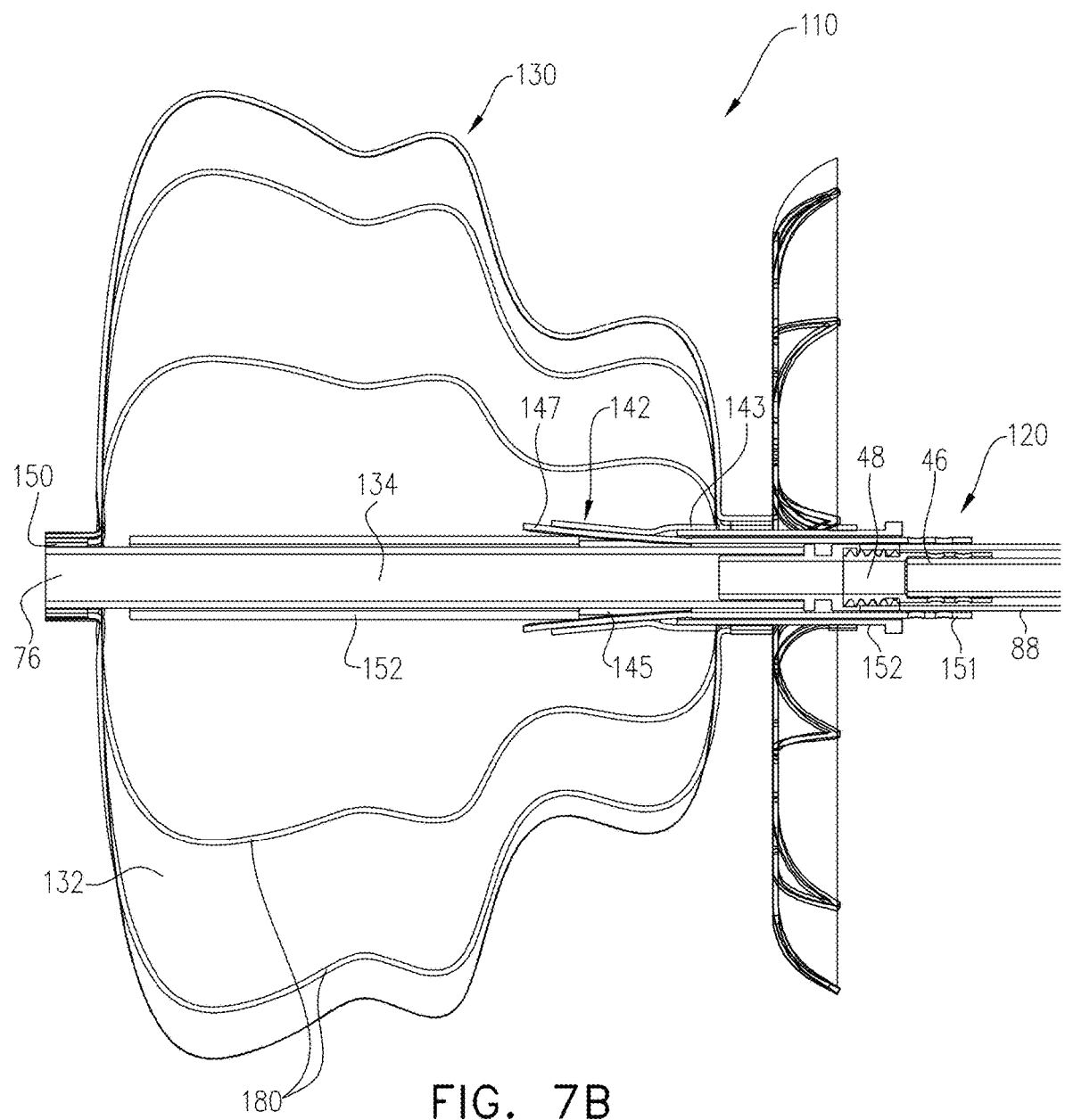
Figure 7C:
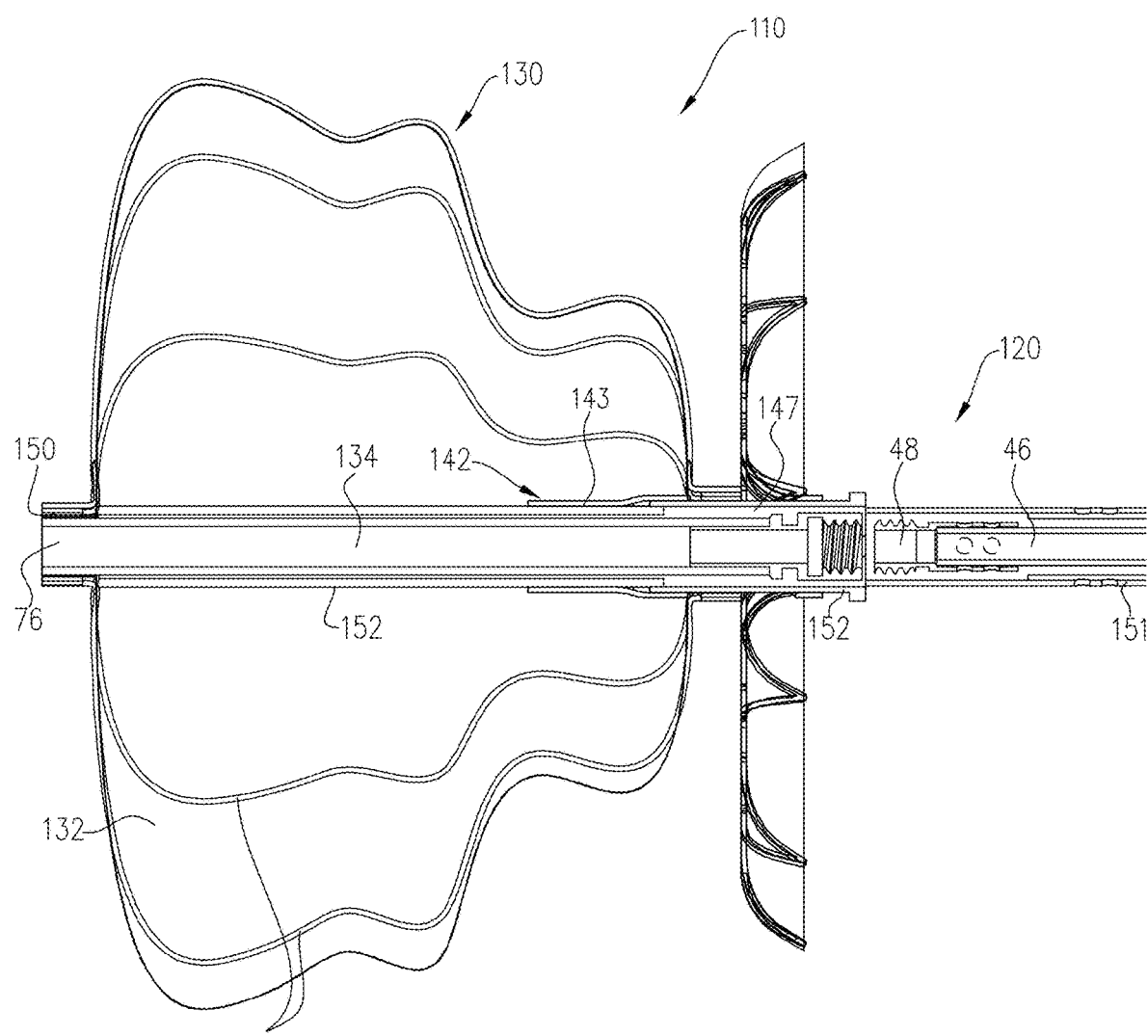

Reference is also made to FIGS. 7A-C, which are schematic cross-sectional illustrations of occlusion device 110 and a distal portion of delivery system 120, in accordance with an application of the present invention. FIGS. 7A-B show occlusion device 110 connected to delivery system 120, with valve 142 of occlusion device 110 in an open state, as described hereinbelow. FIG. 7A shows occlusion device 110 with balloon 130 thereof in an elongated state, and FIGS. 7B-C show occlusion device 110 with balloon 130 in a shortened state. FIG. 7C shows occlusion device 110 connected to delivery system 120, with valve 142 in a closed state.

For some applications, occlusion device 110 comprises:
a compliant balloon 130 defining a fluid-tight balloon chamber 132; balloon 130 may have any of the properties of balloon 30, described hereinabove with reference to FIGS. 1-5;
an actuating shaft 134, which is (a) disposed at least partially within balloon chamber 132, (b) connected to a distal end portion 136 of balloon 130, and (c) longitudinally moveable with respect to a proximal end portion 138 of balloon 130 so as to set a distance between distal and proximal end portions 136 and 138 of balloon 130; and
a valve 142, comprising an elastomer sleeve 143 that surrounds a portion of actuating shaft 134.

Occlusion device 110 is shaped so as to define a fluid flow path 144 having one or more fluid-flow-path openings 145 to balloon chamber 132. Typically, occlusion device 110 is configured such that fluid flow path 144 is coupled in fluid communication with delivery system 120 when occlusion device 110 is releasably connected to delivery system 120.

For example, elastomer sleeve 143 may comprise silicone.

Elastomer sleeve 143 is configured to have a resting state in which the sleeve covers and seals the one or more fluid-flow-path openings 145, such that valve 142 is in a closed state, as shown in FIG. 7C.

Delivery system 120 is configured to be releasably connected to occlusion device 110. Delivery system 120 comprises a valve-opening prop 147, which is configured:
when in a propping position, such as shown in FIGS. 6 and 7A-B, to prop open and deform elastomer sleeve 143 such that elastomer sleeve 143 does not seal the one or more fluid-flow-path openings 145 and valve 142 is in an open state, and
when in a non-propping position, such as shown in FIG. 7C, not to prop open elastomer sleeve 143, such that elastomer sleeve assumes the resting state and valve 142 is in the closed state.

This configuration enables separate control of shortening of balloon 130 and closing of valve 142. Alternatively, valve-opening prop 147 (e.g., tubular portion 151 thereof, described below) is fixed to pull shaft 46.

For some applications, valve-opening prop 147 comprises one or more tabs 149 that extend radially outward from an axis of elastomer sleeve 143, so as to prop open elastomer sleeve 143.

For some applications, valve-opening prop 147 is configured such that axial sliding thereof with respect to elastomer sleeve 143 (e.g., in a proximal direction) transitions valve-opening prop 147 from the propping position to the non-propping position, as shown in the transition between FIG. 7B and FIG. 7C.

For some applications, occlusion device 110 further comprises a proximal tube 152, which is axially fixed with respect to proximal end portion 138 of balloon 130. For some applications, actuating shaft 134 is slidably disposed partially within proximal tube 152.

For some applications, a seal, such as an O-ring (as shown), is provided, and friction between the seal and the inner surface of a proximal tube 152 increases structural stability. Alternatively or additionally, the O-ring, upon completion of the shortening of the balloon, is disposed proximal to the one or more fluid-flow-path openings 145 and blocks additional fluid from passing through the one or more fluid-flow-path openings 145 and elastomer sleeve 143.

For some applications, valve-opening prop 147 comprises a tubular portion 151, which is disposed at least partially within proximal tube 152. For some of these applications, valve-opening prop 147 comprises the one or more tabs 149, which extend (a) axially away from tubular portion 151 (e.g., in a distal direction) and (b) radially outward from proximal tube 152, so as to prop open elastomer sleeve 143. For some applications, the one or more tabs 149 pass through at least a portion of the one or more fluid-flow-path openings 145 when valve-opening prop 147 is in the propping position, such as shown in FIGS. 6 and 7A-B. Alternatively, for some applications, proximal tube 152 is shaped so as to define one or more access openings through a wall of proximal tube 152, and the one or more tabs 149 pass through the one or more access openings at least when valve-opening prop 147 is in the propping position (configuration not shown).

For some applications, occlusion device 110 further comprises proximal LAA-orifice cover 70, which is fixed to proximal tube 152 radially surrounding proximal tube 152. Proximal LAA-orifice cover 70 may implement any of the techniques described hereinabove and/or hereinbelow. For some of these applications, occlusion device 110 further comprises an orifice-support stent 290, described hereinbelow with reference to FIGS. 8 and 9A-B.

For some applications, occlusion device 110 further comprises a locking mechanism, which is configured to assume locked and unlocked states, and which is configured, when in the locked state, to maintain, between distal end portion 136 of balloon 130 and proximal end portion 138 of balloon 130, the distance set using actuating shaft 134. The locking mechanism may implement any of the locking mechanisms described herein, mutatis mutandis.

For some applications, actuating shaft 134 is shaped so as to define, at least in part, a distal tip 150 disposed at distal end portion 136 of balloon 130.

For some applications, occlusion device 110 further comprises connecting struts 180 fixed to distal end portion 136 of balloon 130 and to proximal end portion 138 of balloon 130. Typically, occlusion device 110 is configured such that inflation of balloon chamber 132 plastically deforms connecting struts 180. For some applications, occlusion device 110 is configured such that shortening of balloon 130 plastically deforms connecting struts 180.

For some applications, delivery system 120 further comprising implant catheter 88, such as described hereinabove with reference to FIGS. 1-5.

Figure 7D:
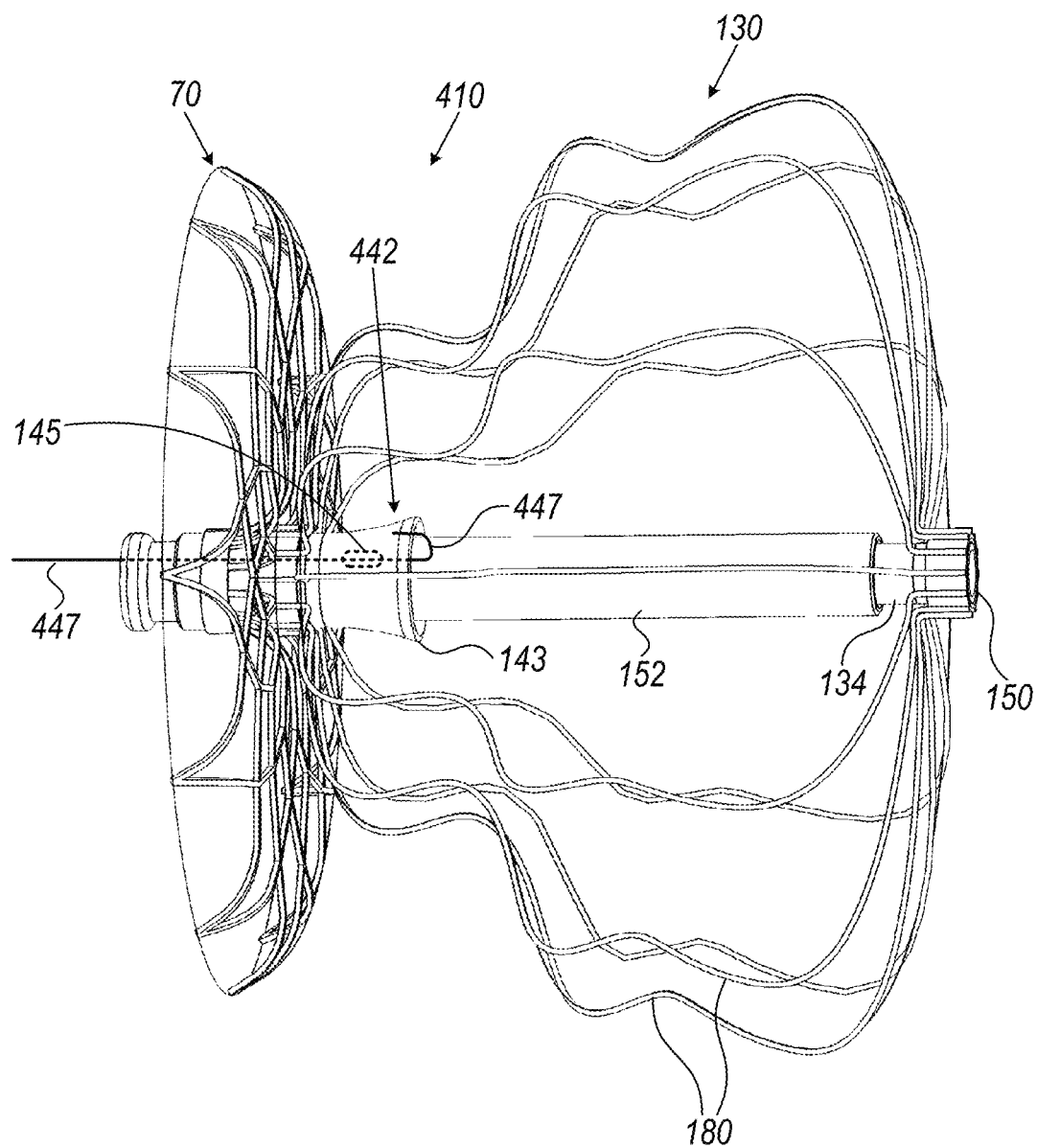
FIG. 7D is a schematic illustration of another occlusion device for occluding an LAA, in accordance with an application of the present invention.

Reference is now made to FIG. 7D, which is a schematic illustration of an occlusion device 410 for occluding an LAA, in accordance with an application of the present invention. For clarity of illustration, a balloon is not shown connected to struts 180 in FIG. 7D, even though it is an actual element of the occlusion device. Occlusion device 410 is for use with a delivery system. Other than as described hereinbelow, occlusion device 410 is similar to occlusion device 110, described hereinabove with reference to FIGS. 6 and 7A-C, and may implement any of the features thereof, mutatis mutandis. Like reference numerals refer to like parts. Similarly, other than as described hereinbelow, the delivery system is similar to delivery system 20, described hereinabove with reference to FIGS. 1-5, and may implement any of the features thereof, mutatis mutandis.

Occlusion device 410 comprises a valve 442, comprising elastomer sleeve 143 that surrounds a portion of actuating shaft 134. Elastomer sleeve 143 is configured to have a resting state in which the sleeve covers and seals the one or more fluid-flow-path openings 145, such that the valve is in a closed state (not shown in FIG. 7D, but similar to the state shown in FIG. 7C for occlusion device 110).

Unlike delivery system 120 of occlusion device 110, the delivery system of the present configuration does not comprise valve-opening prop 147. Instead, the delivery system comprises one or more guidewires 447, which:
- when in a propping position, such as shown in FIG. 7D, prop open and deform elastomer sleeve 143 such that elastomer sleeve 143 does not seal the one or more fluid-flow-path openings 145 and valve 442 is in an open state, and
- when in a non-propping position (not shown in FIG. 7D, but similar to the state shown in FIG. 7C for occlusion device 110), do not prop open elastomer sleeve 143, such that elastomer sleeve assumes the resting state and valve 442 is in the closed state.

For some applications, the one or more guidewires 447 pass through at least a portion of the one or more fluid-flow-path openings 145 when the one or more guidewires are in the propping position.

Figure 8:
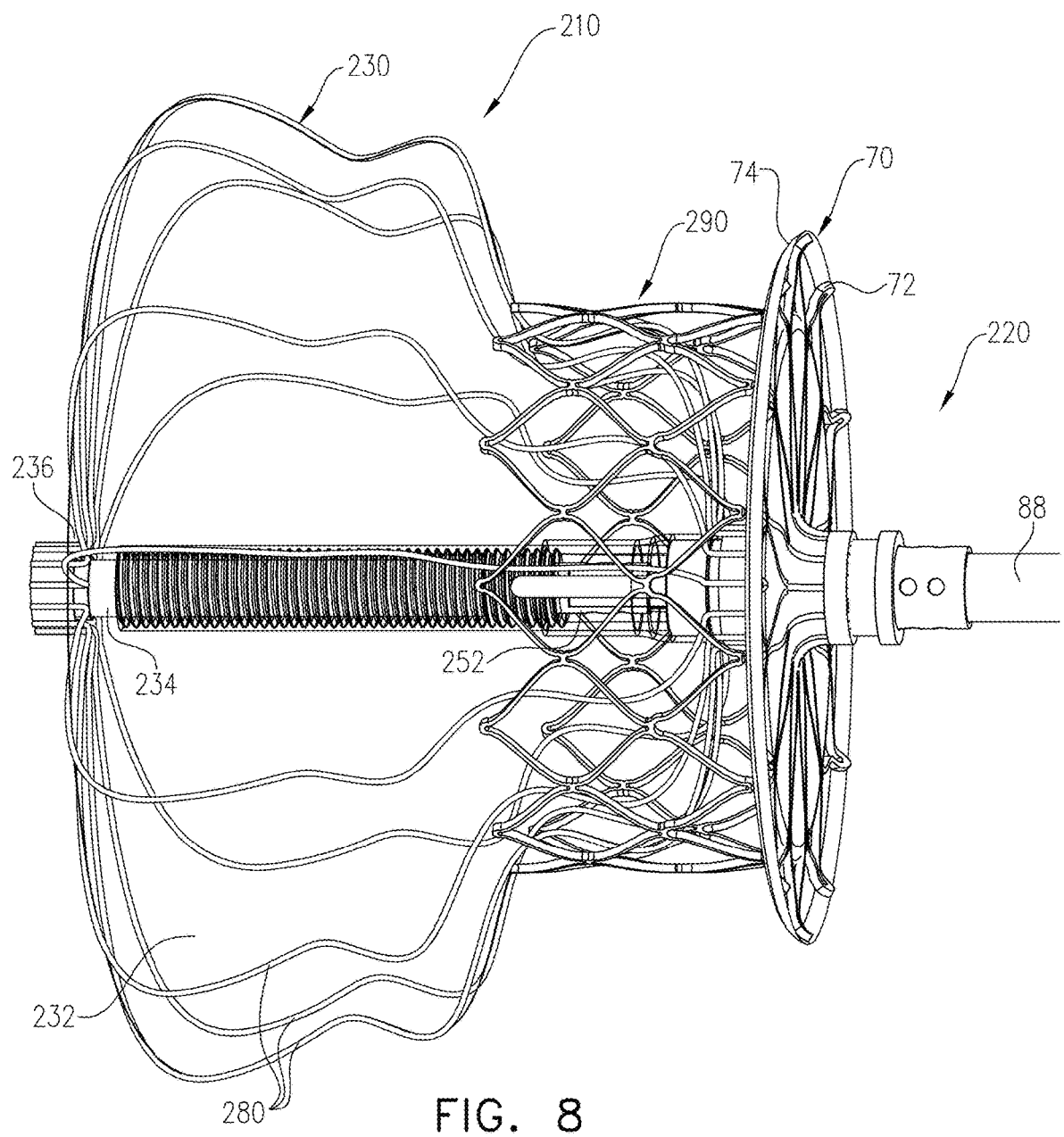
FIG. 8 is a schematic illustration of yet another occlusion device for occluding an LAA, in accordance with an application of the present invention.

Reference is now made to FIG. 8, which is a schematic illustration of an occlusion device 210 for occluding an LAA, in accordance with an application of the present invention. Occlusion device 210 is for use with a delivery system 220. Occlusion device 210 may be implemented in combination with any of the other occlusion devices described herein, mutatis mutandis, including, but not limited to, any of the valves and/or locking mechanisms described herein, mutatis mutandis. Similarly, other than as described hereinbelow, delivery system 220 is similar to the other delivery systems described herein, and may implement any of the features thereof, mutatis mutandis. Like reference numerals refer to like parts.

Reference is also made to FIGS. 9A-B, which are schematic cross-sectional illustrations of occlusion device 210 and a distal portion of delivery system 220, in accordance with an application of the present invention. FIG. 9A-B show occlusion device 210 connected to delivery system 220. FIG. 9A shows occlusion device 210 with balloon 230 thereof in an elongated state, and FIG. 9B shows occlusion device 210 with balloon 230 in a shortened state.

Occlusion device 210 comprises:
- a compliant balloon 230 defining a fluid-tight balloon chamber 232; balloon 230 may have any of the properties of balloon 30, described hereinabove with reference to FIGS. 1-5;
- an actuating shaft 234, which is (a) disposed at least partially within balloon chamber 232, (b) connected to a distal end portion 236 of balloon 230, and (c) longitudinally moveable with respect to a proximal end portion 238 of balloon 230 so as to set a distance between distal and proximal end portions 236 and 238 of balloon 230; and
- a valve 242, which, as mentioned above, may implement any of the features of the valves described herein.

Occlusion device 210 further comprises proximal LAA-orifice cover 70, which (a) is configured to assume a radially-compressed state and a radially-expanded state, (b) comprises frame 72 and covering 74 fixed to frame 72, and (c) when in the radially-expanded state, is generally orthogonal to actuating shaft 234 and has a greatest dimension, measured perpendicular to actuating shaft 234, of at least 10 mm (e.g., at least 20 mm), no more than 50 mm (e.g., no more than 30 mm), and/or between 10 and 50 mm (e.g., between 20 and 30 mm).

Occlusion device 210 still further comprises an orifice-support stent 290, which is configured to enhance support at the orifice of the LAA. Orifice-support stent 290 is configured to be positioned at least partially within the LAA, such as entirely within the LAA. Orifice-support stent 290 is:
- fixed to and extends distally from proximal LAA-orifice cover 70,
- configured to assume a radially-compressed state (not shown) and a radially-expanded state (as shown in FIGS. 8 and 9A-B), and
- generally cylindrical when in the radially-expanded state.

As used in the present application, including in the claims and the Inventive Concepts, the phrase "generally cylindrical" is not limited to generally circularly cylindrical, and also includes within its scope other generally cylindrical shapes, such as generally elliptically cylindrical.

For some applications, orifice-support stent 290, when in the radially-expanded state, has (i) a greatest dimension, measured perpendicular to actuating shaft 234, of at least 8 mm, no more than 50 mm, and/or between 8 and 50 mm, and/or (ii) an axial length of at least 4 mm (e.g. at least 5 mm), no more than 30 mm, and/or between 4 and 30 mm.

For some applications, orifice-support stent 290 is not fixed to balloon 230, such that a shape of balloon 230 can change independently of a shape of orifice-support stent 290. Alternatively or additionally, lack of direct physical contact between orifice-support stent 290 and connecting struts 280 of occlusion device 210 prevents an anodic reaction between the typically super-elastic (e.g., Nitinol) material of struts 280 and the typically plastically deformable (e.g., stainless steel) material of orifice-support stent 290. Such a reaction might have occurred if the two elements were instead welded or otherwise bonded together in contact with each other. (Connection of the elements via an independent and passive element, such as an internal tube or shaft, also does not cause such a reaction.)

For some applications, orifice-support stent 290 comprises a super-elastic or plastically-deformable metal.

Typically, occlusion device 210 is configured such that inflation of balloon chamber 232 transitions orifice-support stent 290 from its radially-compressed state to its radially-expanded state. For some applications, because orifice-support stent 290 comprises a super-elastic metal, such as Nitinol, the stent, when crimped, will have a minimum diameter given by the thickness of its wall struts. When released, the stent tends to transition to its released diameter, which is higher than the crimped diameter. In configurations in which balloon 230 is inflated within the stent, the stent will over-stretch, and its diameter will be greater than its released diameter, to an extent that depends upon the design and ability of over-dilatation of the stent struts.

For some applications, occlusion device 210 further comprises a proximal tube 252, which is axially fixed with respect to proximal end portion 238 of balloon 230. For these applications, proximal LAA-orifice cover 70 is fixed to proximal tube 252 radially surrounding proximal tube 252, and is indirectly connected to balloon 230 via proximal tube 252 and is not directly connected to balloon 230.

Reference is now made to FIG. 10, which is a schematic illustration of an occlusion device 310 for occluding an LAA, in accordance with an application of the present invention. Occlusion device 310 is for use with a delivery system 320. Other than as described hereinbelow, occlusion device 310 is similar to occlusion device 10, described hereinabove with reference to FIGS. 1-5, and may implement any of the features thereof, mutatis mutandis. Similarly, other than as described hereinbelow, delivery system 320 is similar to delivery system 20, described hereinabove with reference to FIGS. 1-5, and may implement any of the features thereof, mutatis mutandis. Like reference numerals refer to like parts.

Reference is also made to FIG. 11, which is a schematic cross-sectional illustration of occlusion device 310 and a distal portion of delivery system 320, in accordance with an application of the present invention. Both FIG. 10 and FIG. 11 show occlusion device 310 connected to delivery system 320. FIG. 10 shows occlusion device 310 with balloon 330 thereof in an elongated state, and FIG. 11 shows occlusion device 310 with balloon 330 in a shortened state, as described hereinbelow.

Occlusion device 310 comprises:
- a compliant balloon 330 defining a fluid-tight balloon chamber 332; balloon 330 may have any of the properties of balloon 30, described hereinabove with reference to FIGS. 1-5;
- a proximal tube 352, which is axially fixed with respect to a proximal end portion 338 of balloon 330;
- a spring 353; and
- a valve 342, which may implement any of the features of the valves described herein.

Spring 353 is (a) disposed at least partially within balloon chamber 232, (b) connected (directly or indirectly, such as via a tube) to a distal end portion 336 of balloon 330 and proximal tube 352, and (c) has a relaxed length, as shown in FIG. 11. When spring 353 has the relaxed length, distal end portion 336 of balloon 330 is at a relaxed distance from proximal end portion 338 of balloon 330, as shown in FIG. 11.

Delivery system 320 is configured to be releasably connected to occlusion device 310. Delivery system 320 comprises a stylet 355, which is removably disposed through proximal tube 352 and within spring 353. Occlusion device 310 is configured such that a degree of distal advancement of stylet 355 within spring 353 sets a tensed length of spring 353, which in turn sets a tensed distance between distal and proximal end portions 336 and 338 of balloon 330, the tensed distance greater than the relaxed distance. One possible tensed distance is shown in FIG. 10.

Typically, during deployment of occlusion device 310 in the LAA, occlusion device 310 is advanced into the LAA with spring 353 in the elongated tensed state. Balloon chamber 332 is typically inflated while spring 353 is in the elongated tensed state, such as shown in FIG. 10, and valve 342 is transitioned to the closed state, such as using techniques described herein. Thereafter, stylet 355 is partially proximally withdrawn, allowing spring 353 to shorten to its resting state, as shown in FIG. 11.

For some applications, a distal end portion of stylet 355 is releasably connected to an occlusion-device connector 357 of occlusion device 310, which is connected to distal end portion 336 of balloon 330. (Even though stylet 355 would generally remain in place even if not connected to occlusion device 310, if not thus connected stylet 355 might become disengaged from the center of spring 353 and become entangled with spring 353 during maneuvering of occlusion device 310 and inflation of balloon 330 during deployment.) For these applications, stylet 355 is disconnected from occlusion-device connector 357 after spring 353 has been allowed to shorten. For example, the end portion of stylet 355 and occlusion-device connector 357 may define respective threads.

Optionally, stylet 355 is flexible, e.g., highly flexible, to accommodate variations in LAA anatomy, including curvature of the LAA.

Reference is now made to FIGS. 12A-B, 13A-B, and 14A-B, which are schematic illustrations of an occlusion device 510 for occluding an LAA, in accordance with an application of the present invention. Occlusion device 510 is for use with a delivery system, such as delivery system 20, described hereinabove with reference to FIGS. 1-4C; delivery system 120, described hereinabove with reference to FIGS. 6-7C; delivery system 220, described hereinabove with reference to FIGS. 8-9B; or delivery system 320, described hereinabove with reference to FIGS. 10-11, mutatis mutandis. Other than as described hereinbelow, occlusion device 510 is similar to occlusion device 10, described hereinabove with reference to FIGS. 1-5, and may implement any of the features thereof, mutatis mutandis. Like reference numerals refer to like parts. Alternatively or additionally, occlusion device 510 may optionally implement any of the features of occlusion device 110, described hereinabove with reference to FIGS. 6 and 7A-C; occlusion device 210, described hereinabove with reference to FIGS. 8 and 9A-B; occlusion device 310, described hereinabove with reference to FIGS. 10 and 11; and/or occlusion device 410, described hereinabove with reference to FIG. 7D, mutatis mutandis. By way of example and not limitation, occlusion device 510 may optionally comprise proximal LAA-orifice cover 70, such as shown in the figures. Similarly, these other occlusion devices described herein may optionally implement any of the features of occlusion device 510, mutatis mutandis.

Figure 12A:
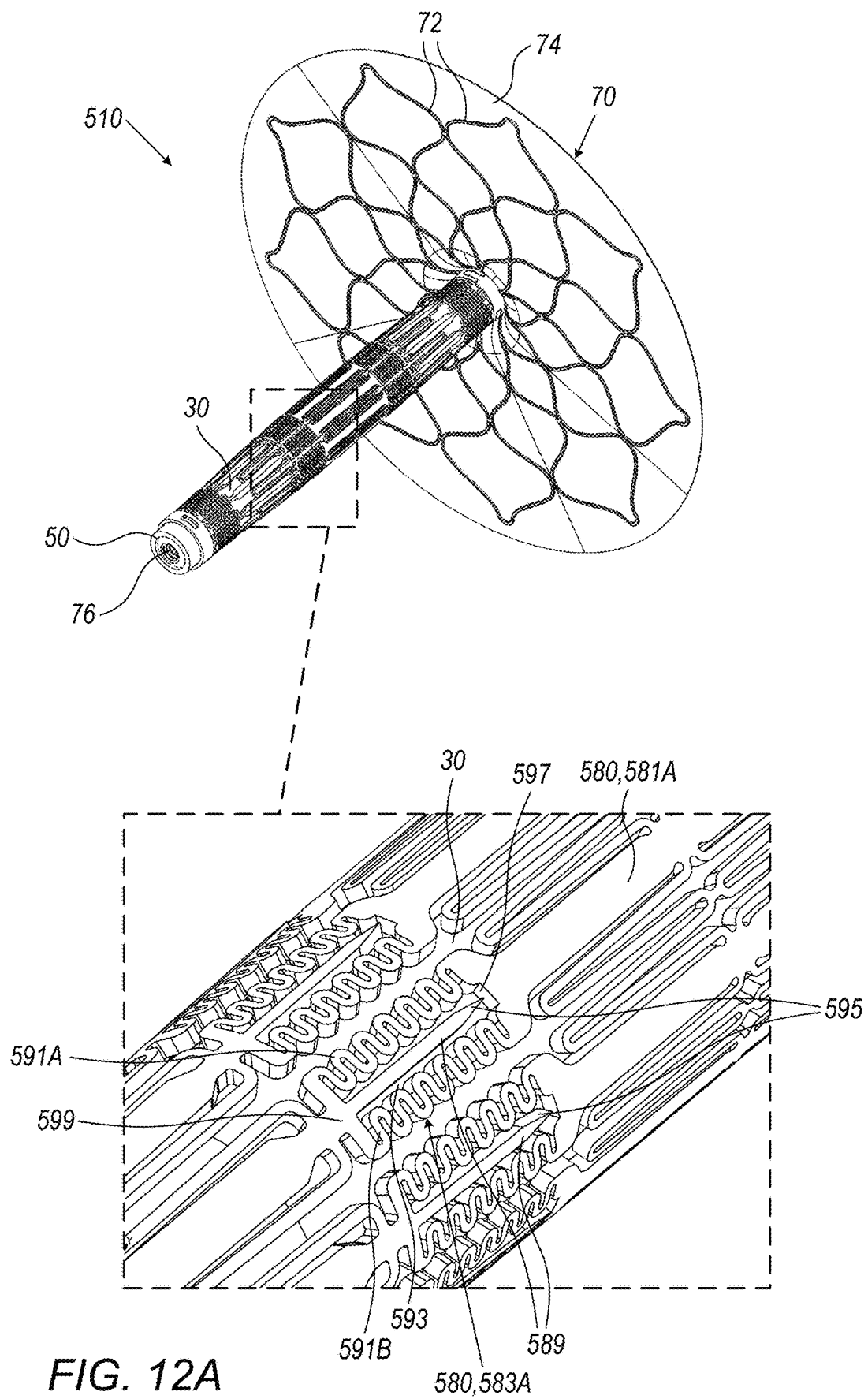
FIGS. 12A-B are schematic illustrations of another occlusion device for occluding an LAA, partially deployed, in accordance with an application of the present invention.
Figure 12B:
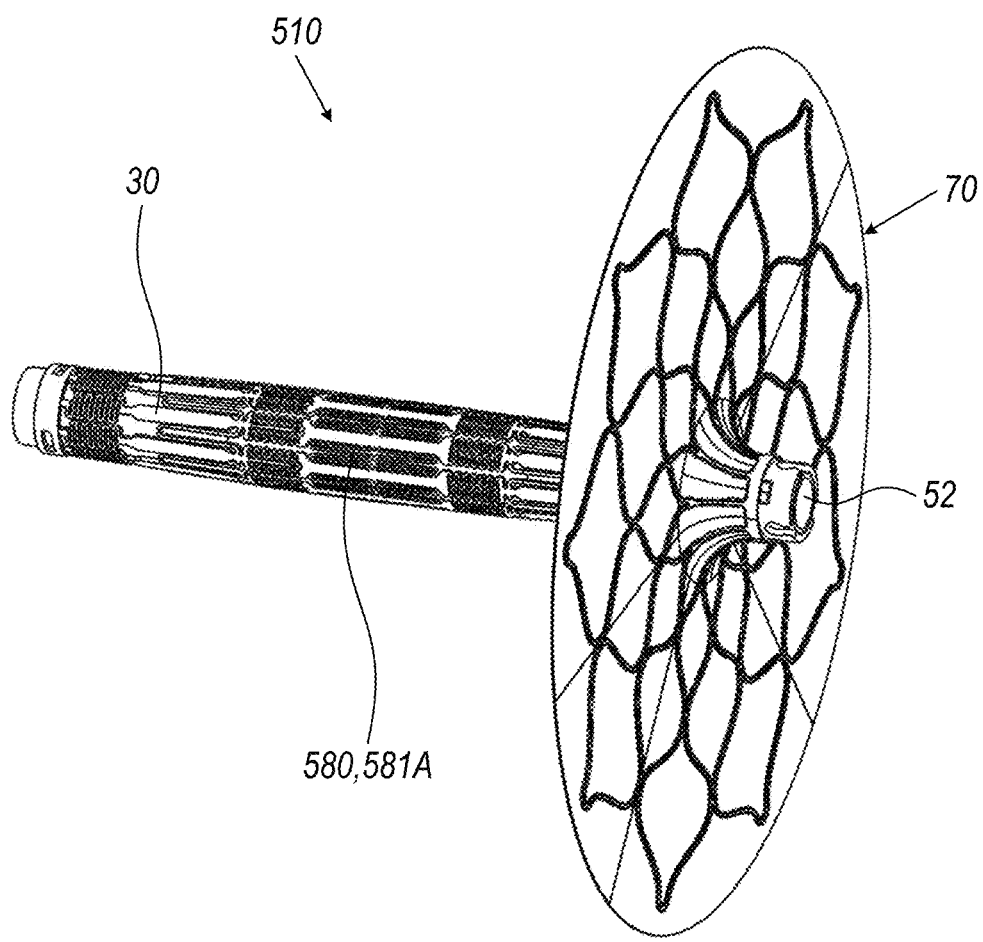

FIGS. 12A-B show occlusion device 510 after sheath 82, shown in FIG. 3A, has been proximally withdraw, thereby releasing occlusion device 510, and allowing proximal LAA-orifice cover 70 to transition to its radially-expanded state. This is similar to the state of deployment of occlusion device 10 shown in FIG. 3B. Balloon 30 remains in a non-inflated, elongate configuration at this stage of deployment.

Figure 13A:
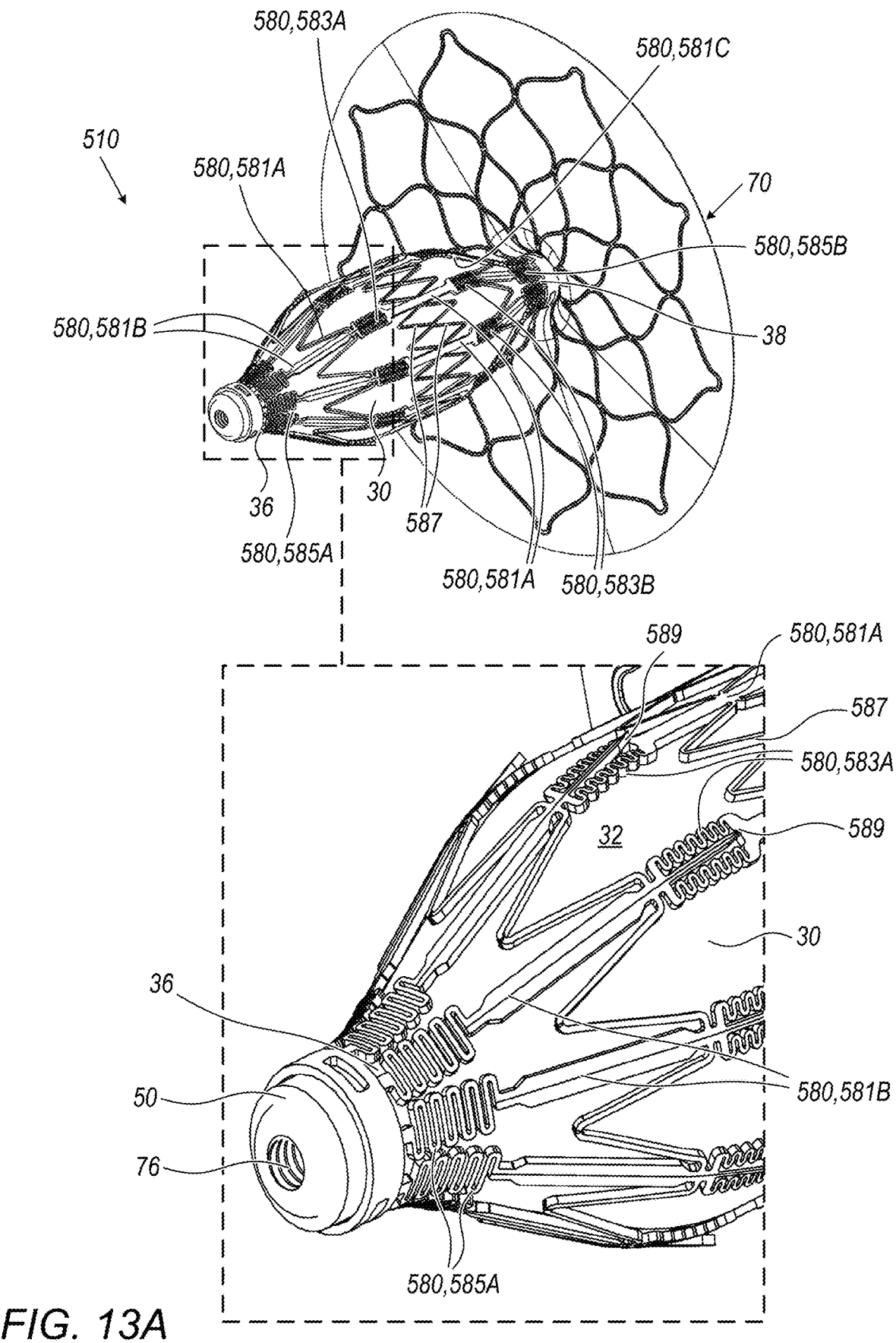
FIGS. 13A-B are schematic illustrations of the occlusion device of FIGS. 12A-B upon partial inflation of a balloon chamber thereof, in accordance with an application of the present invention.
Figure 13B:
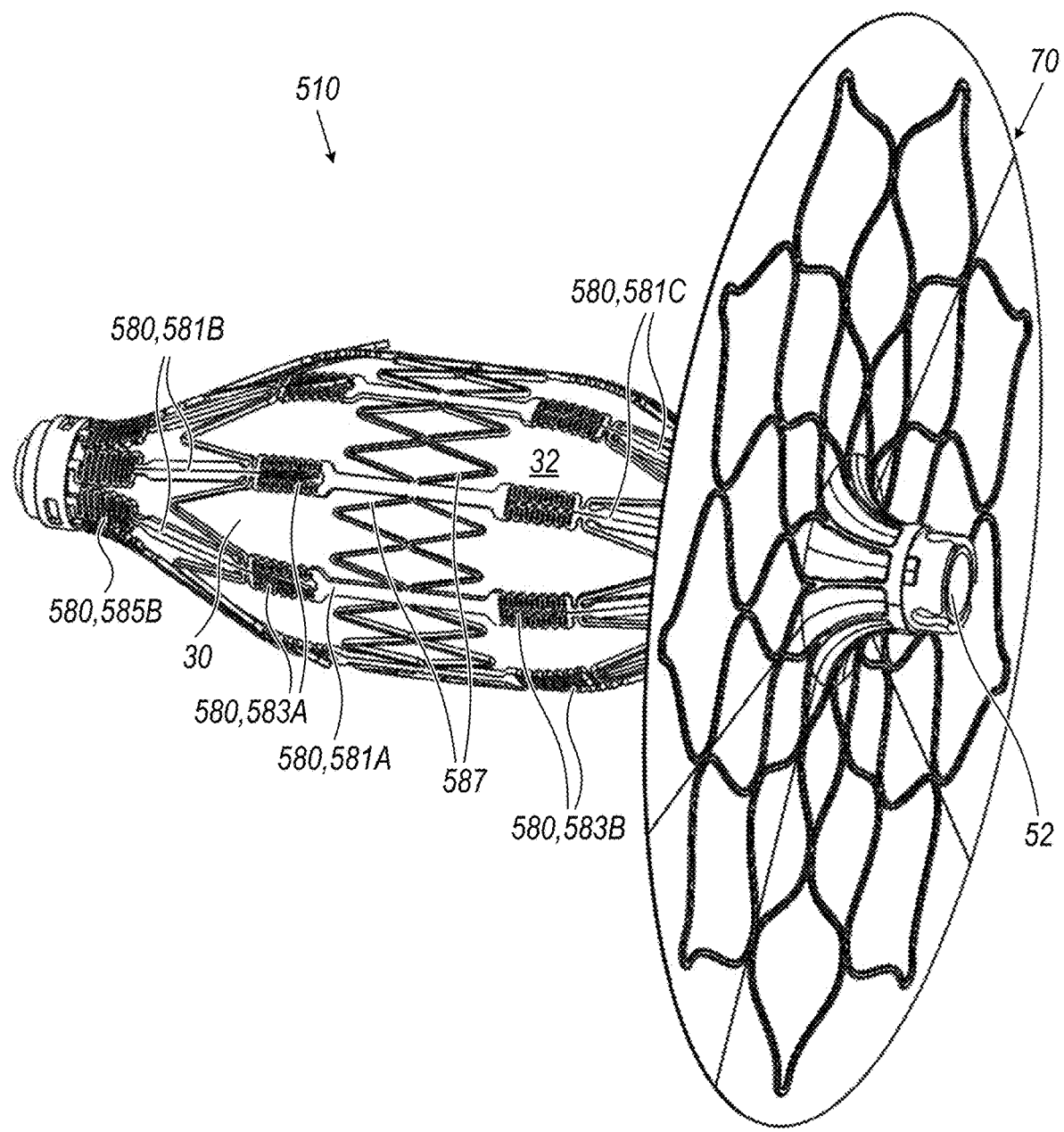

FIGS. 13A-B show occlusion device 510 upon partial inflation of balloon chamber 32.

Figure 14A:
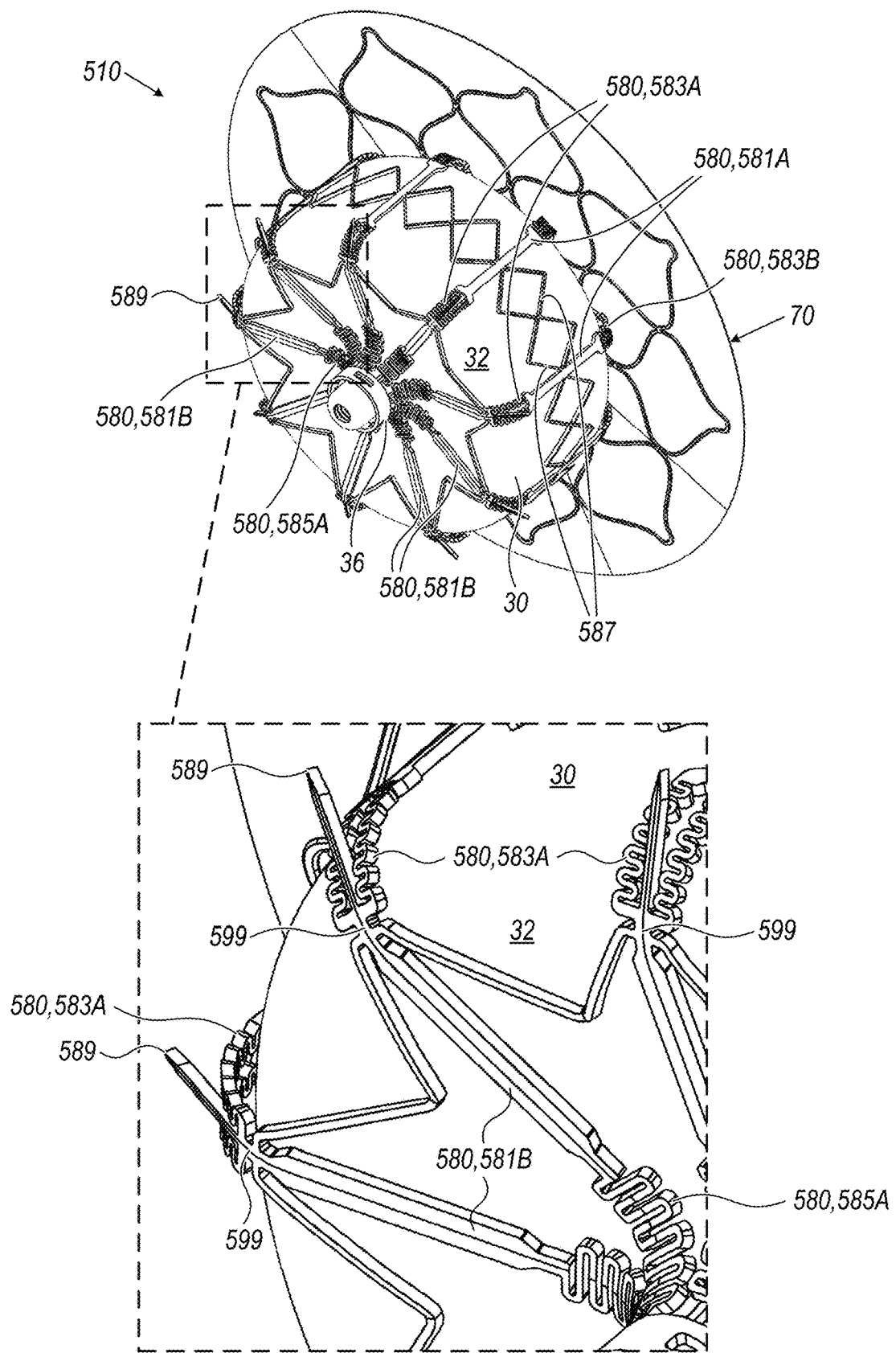
FIGS. 14A-B are schematic illustrations of the occlusion device of FIGS. 12A-B upon final inflation of a balloon chamber thereof, in accordance with an application of the present invention.
Figure 14B:
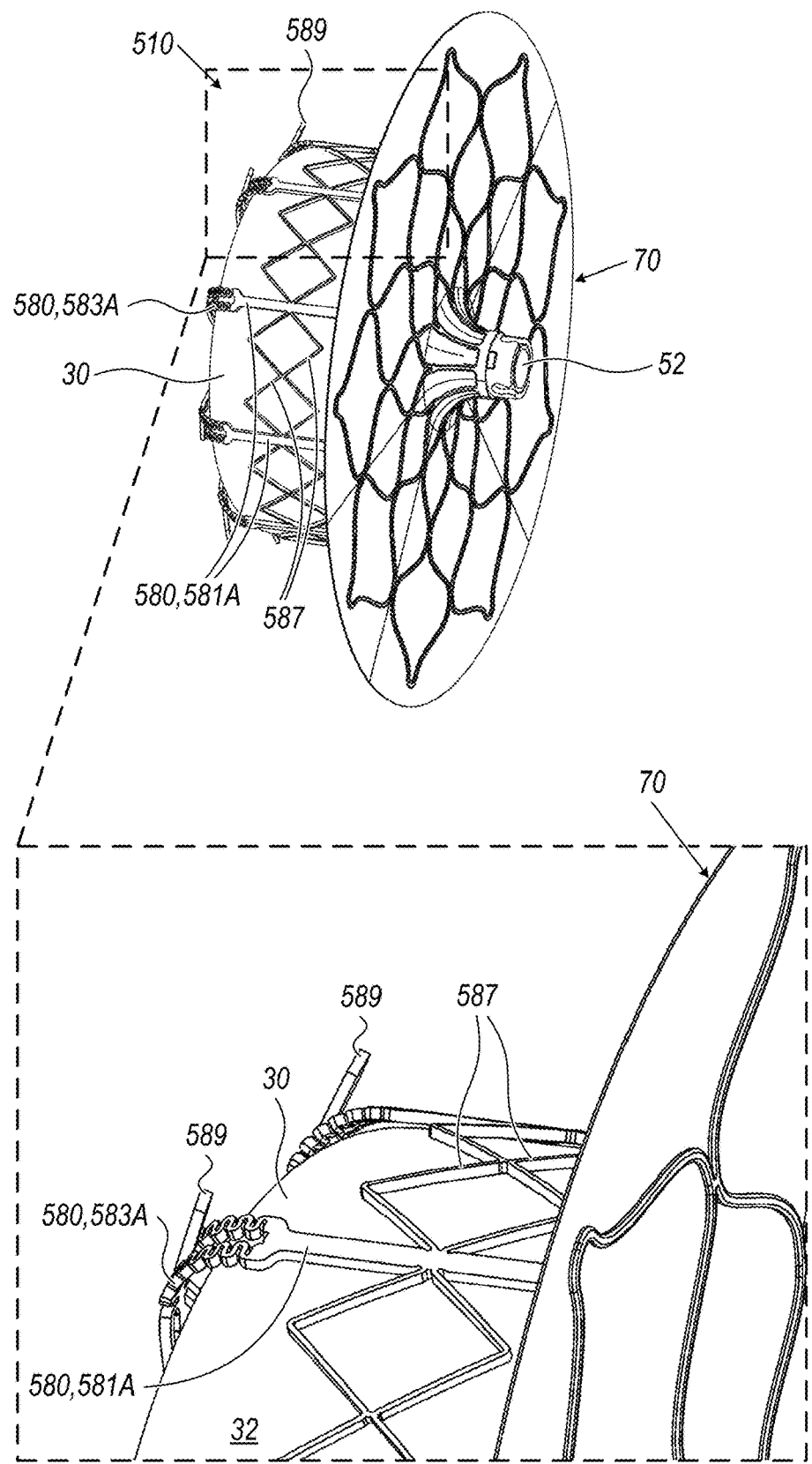

FIGS. 14A-B show occlusion device 510 upon final inflation of balloon chamber 32. Balloon chamber 32 can be inflated at different final inflation levels, depending on the extent of radial expansion necessary for the particular anatomy of the LAA. Typically, occlusion device 510 is configured to be radially expandable to a diameter of between 15 and 40 mm, e.g., between 20 and 35 mm, such as between 15 and 35 mm.

Occlusion device 510 comprises connecting struts 580 fixed to distal end portion 36 of balloon 30 and to proximal end portion 38 of balloon 30. Struts 580 may implement any of the features of struts 80, described hereinabove, mutatis mutandis. First lateral portions 581A of struts 580 are arranged along a lateral surface of balloon 30. Second distal-end portions 581B of struts 580 are arranged on a distal surface of balloon 30. Third proximal-end portions 581C of struts 580 are arranged on a proximal surface of balloon 30. Typically, second distal-end portions 581B and third proximal-end portions 581C are generally straight. Typically, first lateral portions 581A are oriented parallel to a central longitudinal axis of occlusion device 510.

For some applications, distal interface portions 583A of struts 580 join first lateral portions 581A and second distal-end portions 581B, respectively, and/or proximal interface portions 583B join first lateral portions 581A and third proximal-end portions 581C, respectively. Occlusion device 510 is configured such that upon inflation of balloon chamber 32, distal interface portions 583A and proximal interface portions 583B are curved, such as shown in FIGS. 13A-B and 14A-B. (FIGS. 12A-B shown balloon chamber 32 uninflated, FIGS. 13A-B show balloon chamber 32 partially inflated, and FIGS. 14A-B show balloon chamber 32 finally inflated.) For some of these applications, distal interface portions 583A and/or proximal interface portions 583B have a serpentine (e.g., sinusoidal) shape, as shown. This serpentine shape causes distal interface portions 583A and/or proximal interface portions 583B to be more compliant than first lateral portions 581A, second distal-end portions 581B, and/or third proximal-end portions 581C. As a result, occlusion device 510, upon inflation and shortening of balloon 30, assumes a more cylindrical shape that it otherwise would. Optionally, first lateral portions 581A of struts 580 are generally straight, which also contributes to the cylindrical shape of occlusion device 510.

For some applications, distal end portions 585A of struts 580 join second distal-end portions 581B of struts 580 to distal end portion 36 of balloon 30, respectively, and/or proximal end portions 585B of struts 580 join third proximal-end portions 581C of struts 580 to proximal end portion 38 of balloon 30, respectively. Occlusion device 510 is configured such that upon inflation of balloon chamber 32, distal end portions 585A and proximal end portions 585B are curved. (FIGS. 12A-B shown balloon chamber 32 uninflated, FIGS. 13A-B show balloon chamber 32 partially inflated, and FIGS. 14A-B show balloon chamber 32 finally inflated.) For some of these applications, distal end portions 585A and/or proximal end portions 585B have a serpentine (e.g., sinusoidal) shape, as shown. This serpentine shape allows distal end portions 585A and/or proximal end portions 585B to elongate, thereby allowing occlusion device 510 to radially expand, such as to a diameter, for example, of between 15 and 40 mm, e.g., between 20 and 35 mm, such as between 15 and 35 mm. This serpentine shape also allows distal end portions 585A and/or proximal end portions 585B to selectively elongate, thereby accommodating expansion of balloon 30 to different extents in different radial directions.

For some applications, struts 580 are shaped so as to define a plurality of spikes 589 that extend from outer ends 599 (labeled in FIGS. 12A and 14A) of second distal-end portions 581B, respectively, and/or third proximal-end portions 581C, respectively. Spikes 589 are initially generally axially oriented, when balloon 30 is in a non-inflated, elongate configuration, as shown in FIGS. 12A-B. Spikes 589 are configured to extend more radially upon inflation of balloon chamber 32 to serve as tissue-engaging barbs, as shown in FIGS. 14A-B. The respective axes of spikes 589 may be parallel with or slightly angled with respect to axes of second distal-end portions 581B and third proximal-end portions 581C.

For some applications, distal interface portions 583A are shaped so as to define respective pairs of parallel serpentine (e.g., sinusoidal) struts 591A and 591B that define respective narrow elongate gaps 593 therebetween. When spikes 589 are initially generally axially oriented, as shown in FIGS. 12A-B, the spikes are disposed in respective gaps 593. Respective tips 595 of spikes 589 are disposed near respective end surfaces 597 of gaps 593 at respective junctions between the parallel serpentine struts 591A and 591B, such that the respective tips 595 of spikes 589 are protected by respective end surfaces 597 until the spikes are radially deployed. Alternatively or additionally, proximal interface portions 583B and their corresponding spikes 589 may implement this feature.

For some applications, connecting struts 580 further include closed stent cells 587 that connect adjacent pairs of first lateral portions 581A. Optionally, two or more closed stent cells 587 arranged in series connect the adjacent pairs of first lateral portions 581A (in the figures, exactly two closed stent cells 587 arranged in series are shown connecting the adjacent pairs of first lateral portions 581A); typically, no more than four closed stent cells 587 arranged in series, such as exactly two or three closed stent cells 587 arranged in series. These connections by closed stent cells 587 may help laterally stabilize first lateral portions 581A upon inflation of balloon chamber 32, and may help constrain the shape of balloon 30 upon inflation of balloon chamber 32, by helping limit radial expansion of the balloon out of the stent struts. These connections by closed stent cells 587 may alternatively or additionally stabilize the implantation of occlusion device 510 by friction, by providing a sufficiently large contract surface with the walls of the LAA. Optionally, a single series of two or more closed stent cells 587 connect adjacent pairs of first lateral portions 581A, as shown; alternatively, two or more series (e.g., exactly two series) of two or more closed stent cells 587 connect adjacent pairs of first lateral portions 581A (configuration not shown).

Typically, an average width of the struts of first lateral portions 581A equals at least 200% of an average width of the struts of closed stent cells 587, such as at least 250%, 300%, or 400%. As mentioned above, typically first lateral portions 581A are oriented parallel to a central longitudinal axis of occlusion device 510. The struts of closed stent cells 587 may have these thinner widths in order to allow expansion of the closed stent cells with the expansion of the balloon.

For some applications, closed stent cells 587 are shaped as respective rhombuses. Rhombuses can be radially compressed for delivery such that they predictably expand symmetrically, unlike many other stent shapes that tend to expand asymmetrically, such as S-shapes and serpentine shapes. Rhombuses also generally return to their original shape when plastically expanded for implantation after being plastically radially compressed for delivery. For some applications, the rhombuses may be shaped as squares and/or diamonds at certain levels of radial compression and expansion.

In an embodiment, the techniques and apparatus described herein are combined with techniques and apparatus described in one or more of the following patent applications, which are assigned to the assignee of the present application and are incorporated herein by reference:

European Patent Application Publication EP 3 459 469 A1 to Maisano et al.;
PCT Publication WO 2019/057950 to Maisano et al.;
PCT Publication WO 2020/060587 to Maisano et al.; and/or
U.S. Provisional Application 62/906,393, filed Sep. 26, 2019.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An occlusion device for occluding a left atrial appendage (LAA), the occlusion device for use with a delivery system, the occlusion device comprising:
a compliant balloon defining a fluid-tight balloon chamber;
an actuating shaft, which is (a) disposed at least partially within the balloon chamber, (b) connected to a distal end portion of the balloon, and (c) longitudinally moveable with respect to a proximal end portion of the balloon so as to set a distance between the distal and the proximal end portions of the balloon;
a locking mechanism, which is configured to assume locked and unlocked states, and which is configured, when in the locked state, to maintain, between the distal end portion of the balloon and the proximal end portion of the balloon, the distance set using the actuating shaft; and
a valve,
wherein the occlusion device is shaped so as to define a fluid flow path along a portion of the actuating shaft,
wherein the valve is configured to selectively allow or block fluid flow between the fluid flow path and the balloon chamber when the valve is in open and closed states, respectively, and
wherein the occlusion device is configured such that reduction of the distance, by proximal longitudinal movement of the actuating shaft:
(a) to a first predetermined distance between the distal and the proximal end portions of the balloon automatically transitions the valve from the open state to the closed state, and
(b) to a second predetermined distance between the distal and the proximal end portions of the balloon automatically transitions the locking mechanism from the unlocked state to the locked state.

2. The occlusion device according to claim 1, wherein the first predetermined distance does not equal the second predetermined distance.

3. The occlusion device according to claim 2, wherein the first predetermined distance is less than the second predetermined distance.

4. The occlusion device according to claim 1, wherein the first predetermined distance equals the second predetermined distance.

5. The occlusion device according to claim 1, wherein the occlusion device is configured to be releasably connected to the delivery system, and wherein the occlusion device is configured such that the fluid flow path is coupled in fluid communication with the delivery system when the occlusion device is releasably connected to the delivery system.

6. The occlusion device according to claim 1, wherein the occlusion device further comprises a distal tip disposed at the distal end portion of the balloon, wherein the actuating shaft is connected to the distal tip.

7. The occlusion device according to claim 1, wherein the actuating shaft is shaped so as to define, at least in part, a distal tip disposed at the distal end portion of the balloon.

8. The occlusion device according to claim 1, wherein the occlusion device further comprises a proximal base disposed at the proximal end portion of the balloon, wherein the actuating shaft is moveable with respect to the proximal base.

9. The occlusion device according to claim 1, for use with a guidewire, wherein the actuating shaft is shaped so as to define a guidewire lumen for slidingly receiving therein the guidewire.

10. The occlusion device according to claim 1, wherein the occlusion device is shaped so as to define the fluid flow path alongside the portion of the actuating shaft.

11. The occlusion device according to claim 1, wherein the valve is disposed along the actuating shaft.

12. The occlusion device according to claim 1, wherein the occlusion device further comprises a proximal tube, which is axially fixed with respect to the proximal end portion of the balloon, wherein the actuating shaft is slidably disposed partially within the proximal tube.

13. The occlusion device according to claim 12, wherein the occlusion device is shaped so as to define the fluid flow path along the portion of the actuating shaft radially between an external surface of the actuating shaft and an internal surface of the proximal tube.

14. The occlusion device according to claim 13, wherein the valve is disposed along the actuating shaft.

15. The occlusion device according to claim 14, wherein the valve comprises a seal around at least a portion of the external surface of the actuating shaft, and wherein the valve is configured to assume the open state when the seal is disposed at one or more first axial positions with respect to the proximal tube, and the closed state when the seal is disposed at one or more second axial positions with respect to the proximal tube, the one or more second axial positions proximal to the one or more first axial positions.

16. The occlusion device according to claim 15, wherein the seal, the actuating shaft, and the proximal tube are arranged such that the seal blocks fluid flow out of a distal end of the proximal tube at least when the seal is disposed at the one or more first axial positions with respect to the proximal tube.

17. The occlusion device according to claim 13, wherein a wall of the proximal tube is shaped so as to define one or more tabs through the wall, wherein the one or more tabs are biased to flex radially inward, and wherein, when the valve is in the open state, the fluid flow path passes through the wall between respective proximal ends of the one or more tabs and a non-tabbed portion of the wall axially adjacent the one or more tabs.

18. The occlusion device according to claim 17, wherein the non-tabbed portion of the wall is disposed proximal to the one or more tabs.

19. The occlusion device according to claim 17, wherein the external surface of the actuating shaft is shaped so as to define one or more protrusions around at least a portion of the actuating shaft, and wherein the proximal ends of the one or more tabs are shaped so as to prevent distal movement of the one or more protrusions when the one or more protrusions are disposed proximal to the proximal ends of the one or more tabs, thereby causing the locking mechanism to assume the locked state.

20. The occlusion device according to claim 1, wherein the occlusion device further comprises a proximal connector that is configured to releasably connect the occlusion device to a correspondingly configured distal connector of the delivery system.

21. An occlusion system comprising the occlusion device according to claim 1, the occlusion system for use with a guidewire and further comprising the delivery system cooperating therewith, the delivery system comprising an implant catheter connected to an operating handle, the implant catheter comprising a longitudinal passageway for the guidewire, a distal connector for releasably connecting the implant catheter to the correspondingly configured proximal connector of the occlusion device, and an inflation tube channel releasably connectable to the fluid flow path of the occlusion device.

* * * * *